(12) United States Patent
Matos

(10) Patent No.: US 8,706,225 B2
(45) Date of Patent: Apr. 22, 2014

(54) CONTROL OF A DEFIBRILLATOR AND/OR PACEMAKER

(71) Applicant: Jeffrey A. Matos, New Rochelle, NY (US)

(72) Inventor: Jeffrey A. Matos, New Rochelle, NY (US)

(*) Notice: Subject to any disclaimer, the term of this patent is extended or adjusted under 35 U.S.C. 154(b) by 0 days.

(21) Appl. No.: 13/840,021

(22) Filed: Mar. 15, 2013

(65) Prior Publication Data

US 2013/0282071 A1     Oct. 24, 2013

Related U.S. Application Data

(63) Continuation-in-part of application No. 13/537,318, filed on Jun. 29, 2012, now Pat. No. 8,565,882, which is a continuation of application No. 11/895,934, filed on Aug. 28, 2007, now Pat. No. 8,214,043.

(60) Provisional application No. 60/840,772, filed on Aug. 29, 2006, provisional application No. 60/930,525, filed on May 17, 2007, provisional application No. 60/928,567, filed on May 10, 2007.

(51) Int. Cl.
    *A61N 1/372*      (2006.01)

(52) U.S. Cl.
    USPC .................................. 607/30; 607/60; 607/5

(58) Field of Classification Search
    USPC .............................. 607/32, 60, 5, 2
    See application file for complete search history.

*Primary Examiner* — Carl H Layno
*Assistant Examiner* — Paula J Stice
(74) *Attorney, Agent, or Firm* — Karl F. Milde, Jr.; Eckert Seamans Cherin & Mellott, LLC

(57) ABSTRACT

An electronic medical person access to a medical professional (MP) who can monitor, diagnose and treat the person from a remote site. The apparatus includes a plurality of medical treatment devices coupled to an electronic adapter designed to communicate with (A) each treatment device and (B) a local, first transmitting/receiving device which, in turn, is adapted to electronically communicate with a remote, second transmitting/receiving device used by the MP. Signals representing physiologic information of the person via the adapter to the MP and, in response, the MP may transmit a control signal to one or more treatment devices. The treatment devices may communicate via the adapter.

39 Claims, 39 Drawing Sheets

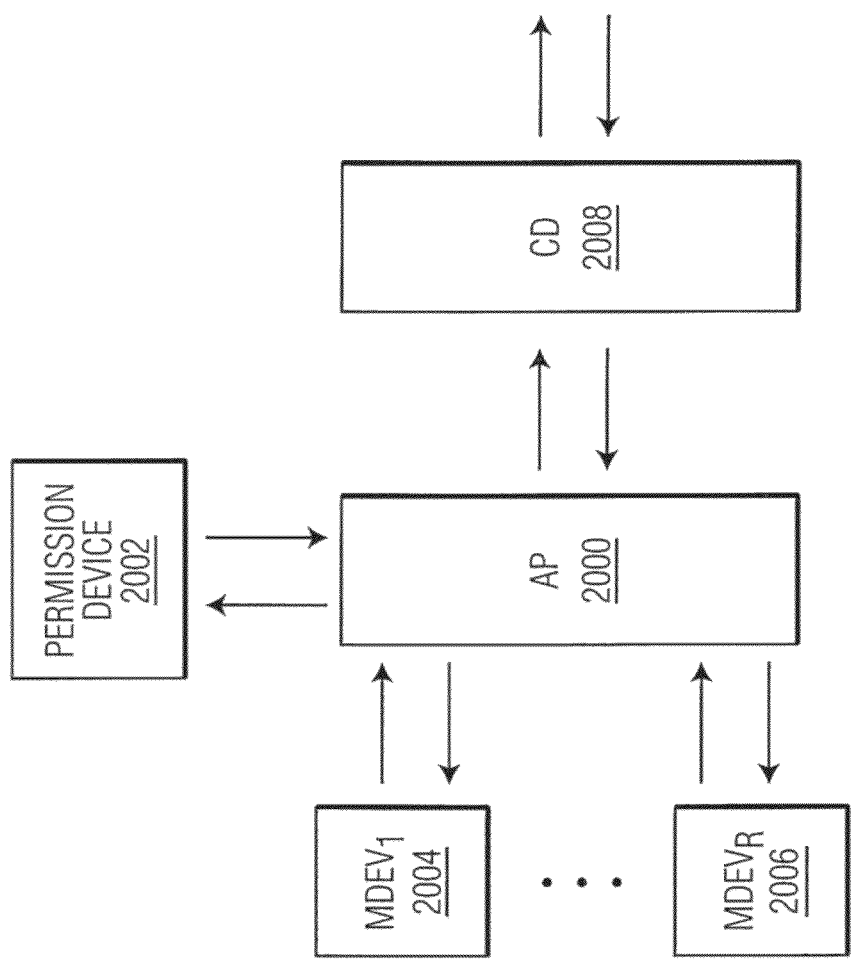

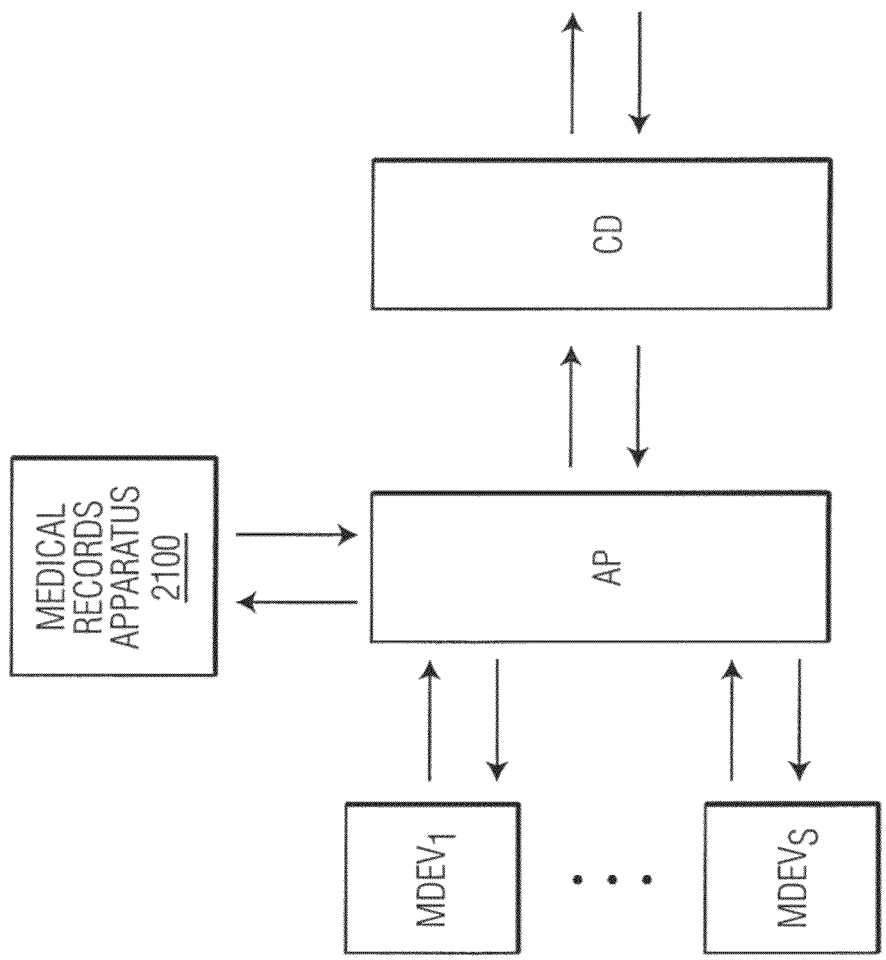

CONTROL OF A DEFIBRILLATOR AND/OR PACEMAKER

CROSS-REFERENCE TO RELATED APPLICATIONS

This application claims priority from the following provisional and utility patent applications:
1) U.S. Provisional Application Ser. No. 60/840,772, filed Aug. 29, 2006;
2) U.S. Provisional Application Ser. No. 60/928,567, filed May 10, 2007;
3) U.S. Provisional Application Ser. No. 60/930,525L filed May 17, 2007;
4) U.S. patent application Ser. No. 11/895,934, filed Aug. 24, 2007 (now U.S. Pat. No. 8,214,043); and
5) U.S. patent application Ser. No. 13/537,318, filed Jun. 29, 2012 (now U.S. Pat. No. 8,565,882, from which this application is a continuation-in-part.

The subject matter of this application is a related to that of the following U.S. patents and patent publications:
U.S. Pat. No. 7,277,752
U.S. Pat. No. 7,769,465
U.S. Pat. No. 7,840,277
U.S. Pat. No. 8,180,457
U.S. Pat. No. 8,214,043
U.S. Pat. No. 8,473,065
U.S. Pat. No. 8,565,882
US 2007/0043585 A1
US 2010/0268304 A1
US 2011/0172740 A1
US 2012/0314048 A1

The aforementioned patents and patent publications are incorporated herein by reference.

BACKGROUND OF THE INVENTION

Cardiac arrest outside of the hospital is nearly always fatal. Despite the fact that for decades, defibrillator technology—which has the potential to restore a survivable heart rhythm when a lethal one has caused the arrest—has been available, the rate of sudden death due to cardiac arrest remains very high.

The crux of the problem is that a defibrillator shock must be administered within a very short time after the onset of the arrest-causing heart rhythm—generally ventricular tachycardia (VT) or ventricular fibrillation (VF). It is estimated that the mortality increases by approximately 10% for each minute after the onset of an arrest. Calling 9-1-1 or the equivalent results in response times that are far too long.

Industry's response has been the development of the automatic external defibrillator (AED). The electrodes of this device are applied to a victim or possible victim by a bystander, the device then analyzes the heart rhythm, and makes a shock/no-shock decision.

Drawbacks of AEDs Include:
1) They may malfunction. Numerous examples of such malfunctions have been reported. Some malfunctions are those that can occur with any electronic device, i.e. due to component failure. Other malfunctions may be related to inadequate maintenance of the device by the owner.

Still other problems are due to "pseudo-malfunctions." One type of pseudo-malfunction is that the algorithm for ECG analysis may fail to properly diagnose the rhythm abnormality. There is no algorithm which is 100% accurate. Thus an AED which fails to shock because it's algorithm is not 100% sensitive (i.e. does not correctly detect 100% of actual VT or VF) may be operating according to specification even at the time of a failure to make a correct diagnosis; If an identical rhythm were presented to another AED with the same algorithm, that AED would also fail to properly diagnose. Another common type of pseudo-malfunction is the user failing to properly use the device.

The current invention addresses the aforementioned issues by providing real-time supervision and management by a remotely located medical professional (MP) operating a remotely controlled defibrillator (RCD), from the moment that defibrillator use begins. The MP analyzes the rhythm—either as the primary means of arriving at a rhythm diagnosis, or by over-reading (and, if necessary, over-ruling) the analysis of the on-scene defibrillator device. The MP has means and methods available to him for use in the event that the rhythm diagnosis is uncertain. The MP makes sure that an untrained or minimally trained user is using the defibrillator device properly. The MP or his associates may assure that the defibrillator device is maintained properly.

2) A second AED drawback: For some victims of an arrest, an older methodologic paradigm entailing the delivery of a shock as soon as possible, seems now to be a sub-optimal approach. Instead, a period of cardiopulmonary resuscitation (CPR) preceding a shock seems—for some, but not all victims—to be a better plan. Despite decades of effort by various workers to teach CPR to a broad fraction of the general population, most people do not know how to do it, and do not want to learn how. Furthermore, there is very good evidence that trained physicians and emergency medical technicians often perform CPR sub-optimally.

The current invention addresses these issues by allowing the MP to supervise CPR-related matters. These matters include:
whether to begin CPR first, or whether to shock first instead;
how long CPR should be performed;
when and for how long is it permissible to interrupt CPR;
rate of chest compression;
depth of chest compression;
position of the resuscitating person's hands during CPR;
decision about whether chest ventilation should accompany chest compression;
decision—if ventilation is to be performed—about the admixture of chest compression and ventilation;
assessment of the adequacy of ventilation (i.e. rate and volume of ventilation); and
use of ventilation assistance devices, as are known in the art.

3) A third AED drawback: For not-hard-to-understand reasons, most people are quite uncomfortable with the notion of presiding over a do-it-yourself cardiac arrest. Voice prompts from an AED do little to allay this anxiety. The anxiety results in limitation of sales and deployment of AEDs and in bystander reluctance to get involved. The aforementioned refers to general anxiety, outside of an actual arrest. During an actual arrest, the anxiety problem increases many-fold. Even experienced physicians and emergency workers are anxious during an actual arrest; As a result their performance suffers. Erratic behavior, and at times chaotic scenes are not entirely uncommon.

The current invention addresses this issue by making the bystander into a "helper" who follows the orders of the MP. The presence of the MP, therefore, removes the single largest source of arrest-related anxiety for the bystander: the enormous responsibility implicit in supervising a "life-and-death" event. Using the invention, the MP can even assist emergency medical technicians who are using a manual defibrillator, if the manual defibrillator is coupled to apparatus described herein, which allows it to be remotely accessed and, if necessary, controlled by a remote medical expert.

4) A fourth AED drawback: legal issues. Although good Samaritan statutes provide protection for some situations, they are not uniform and do not protect the involved bystander or AED owner under all circumstances. Some statues require user training, user AED maintenance and registration with local 9-1-1 authorities. It is not uncommon to see, in public places, an AED cabinet with words similar to: "FOR USE BY TRAINED MEDICAL PERSONNEL ONLY". A difficult, if not impossible to measure parameter is 'How many people do not obtain AEDs because of fear of a potentially burdensome legal entanglement?'

A defibrillator which is remotely controlled by an expert medical professional can address the legal issue, by making user competence and proper performance into non-issues.

Another industry innovation for the management of cardiac arrest in a higher risk population than that intended for AED protection is the implantable cardioverter defibrillator (ICD). This device acts as a miniaturized, implantable AED; Indeed, in the early years of its existence, it was referred to as "AID", an abbreviation of automatic internal defibrillator. It continuously analyzes an internally detected cardiac electrical signal. Upon detection of either VT or VF, it can attempt restoration of a normal rhythm by either shock or overdrive/anti-tachycardia pacing (ATP).

ICD Drawbacks are these:

1) Initial Cost. Currently available devices cost about $20,000. The hospitalization for the implant may cost as much as two or more times the device cost. The total cost to the healthcare system for such devices is large. As the medical indications for ICD implantation have broadened, and the number of implants has significantly increased, total costs to the health care system have gone up very substantially. Although indications for some implants are uniformly agreed upon (e.g. cardiac arrest not due to a myocardial infarction in a young person with a depressed ejection fraction and no clear reversible cause), it has become clear that there is a gray-zone of people with intermediate levels of risk, for whom there is not uniform agreement about implantation. Some highly respected authorities have raised serious concerns about excessive or potentially excessive numbers of ICD implants. Although home AEDs are a possible alternative to ICDs in such gray-zone situations, there has been extraordinarily little enthusiasm for this approach, among physicians and patients.

2) Maintenance cost. ICDs have a finite battery life, and must be replaced—about once every six years, depending on device use. Furthermore, the devices need to be checked by a medical professional intermittently. The schedule for such checks may be as infrequent as once very four months, or much more frequently, if the patient is experiencing difficulties due to frequent rhythm abnormalities.

3) Reliability. Though they seldom fail to shock for an actual VT or VF event, various lower level device malfunctions are not uncommon. All U.S. manufacturers have reported component and software failures from time to time during recent years, some catastrophic, resulting in death. Furthermore, pseudo-malfunctions, i.e. malfunctions due to improper programming are possible and certainly do happen. For example, if the device is programmed to detect VT at rates above 180 beats per minute (b.p.m.), and the ICD owner develops VT as 170, the device will not treat the event. Simply programming the device to a low value of rate cutoff (e.g. 140 b.p.m.) potentially sets the patient up for another type of common pseudo-malfunction: receiving shocks for a rhythm which is not VT or VF. Inappropriate shocks can be a big problem because not infrequently, they occur as clusters of events, sometimes entailing numerous shocks;

the shock, though brief, is painful, and generally heightens the patient's anxiety level for quite some time beyond the actual event.

Remotely controlled defibrillator technology addresses these problems in the following ways:

1) It provides a protection system for low to intermediate risk patients, which is far less costly than an ICD and more attractive than an AED, for the aforementioned reasons.

2) It provides a means of remotely controlling ICDs which would allow a remotely located medical professional to override the decision of an ICD in the event that:

one or more shocks were delivered inappropriately;

a shock was not delivered, and should have been;

a series of shocks was ineffective, and additional ones are appropriate but the device algorithm does not call for them; and if a level of therapy less aggressive than shocks (e.g. ATP) is appropriate.

3) It allows for the detection of device malfunction in real-time, either by the detection of an inappropriate treatment, or by the real-time or nearly real-time detection of a telemetry abnormality concerning device self-testing and self-monitoring. Furthermore, remotely controlled ICD programming would allow for the possibility of a remotely supervised remedy of a malfunction. One of the most notorious ICD failures, which resulted in loss of life, was ultimately patched by a software fix. The interval of time from when the software fix was available until the time that it was fully deployed was a large number of days; The interval of time from first patient death due to the malfunction until curative software deployment was even longer. If the remotely controlled defibrillation technology described herein and in the referenced applications had been available:

a) The problem might have been identified sooner by self-reporting fault detecting telemetry;

b) From the time of problem identification, remote MPs could have performed a watchdog function and possibly overridden any inappropriate ICD action; and c) The software patch would have been disseminated in hours, rather than over a period of days to weeks.

The disclosure herein addresses:

Apparatus and methods by which an AED may be simply modified to operate as a remotely controlled defibrillator by the attachment of a communication device;

Apparatus and methods by which a cellular telephone or other personal communication device may be simply modified, to operate in conjunction with an AED;

An adapter device, which when attached to an AED and to a cellular telephone or other personal communication device, allows the three devices in conjunction to operate as a remotely controlled defibrillator.

Facilitation of the remote control of manually operated external defibrillators and pacemakers using an adapter-based system.

Facilitation of the remote control of implanted pacemakers and defibrillators using an adapter based system.

The disclosure also addresses the use of an adapter to facilitate communication among multiple medical devices;

facilitate communication between (i) multiple medical devices; and (ii) a communications relay unit;

facilitate communication between (i) multiple medical devices; and (ii) a recipient of information produced by one or more of the devices; and facilitate communication between (i) multiple medical devices; and (ii) a source of control for one or more of the devices.

BRIEF DESCRIPTION OF THE DRAWINGS

FIG. 20 shows a block diagram of an adapter system which includes a permission device.

FIG. 21 shows a block diagram of an adapter system which includes a medical records apparatus.

DETAILED DESCRIPTION OF THE PREFERRED EMBODIMENTS

In the disclosure hereinabove and hereinbelow: "Defibrillation" and "defibrillator" are the nouns used to refer to the act of and the device which terminates a rapid heart rhythm with a non-synchronized shock. These two terms are, herein, intended to also refer to "cardioversion" and "cardioverter", respectively, these latter two terms implying a synchronized shock.

The detailed description may be broadly divided into:
1) Overview of device function (FIGS. 1-5)
2) Example: System with unified adapter and communication device (FIGS. 6-9)
3) Example: Detailed Description of a modified external defibrillator system which may have various embodiments (FIG. 10)
4) Example: System with unified adapter and cardiac monitoring and treatment device (FIGS. 11-13)
5) Example: Versions of the system with at least one implantable component (FIGS. 14A, 14B and 14C).

Overview of Device Function

Figure 1:
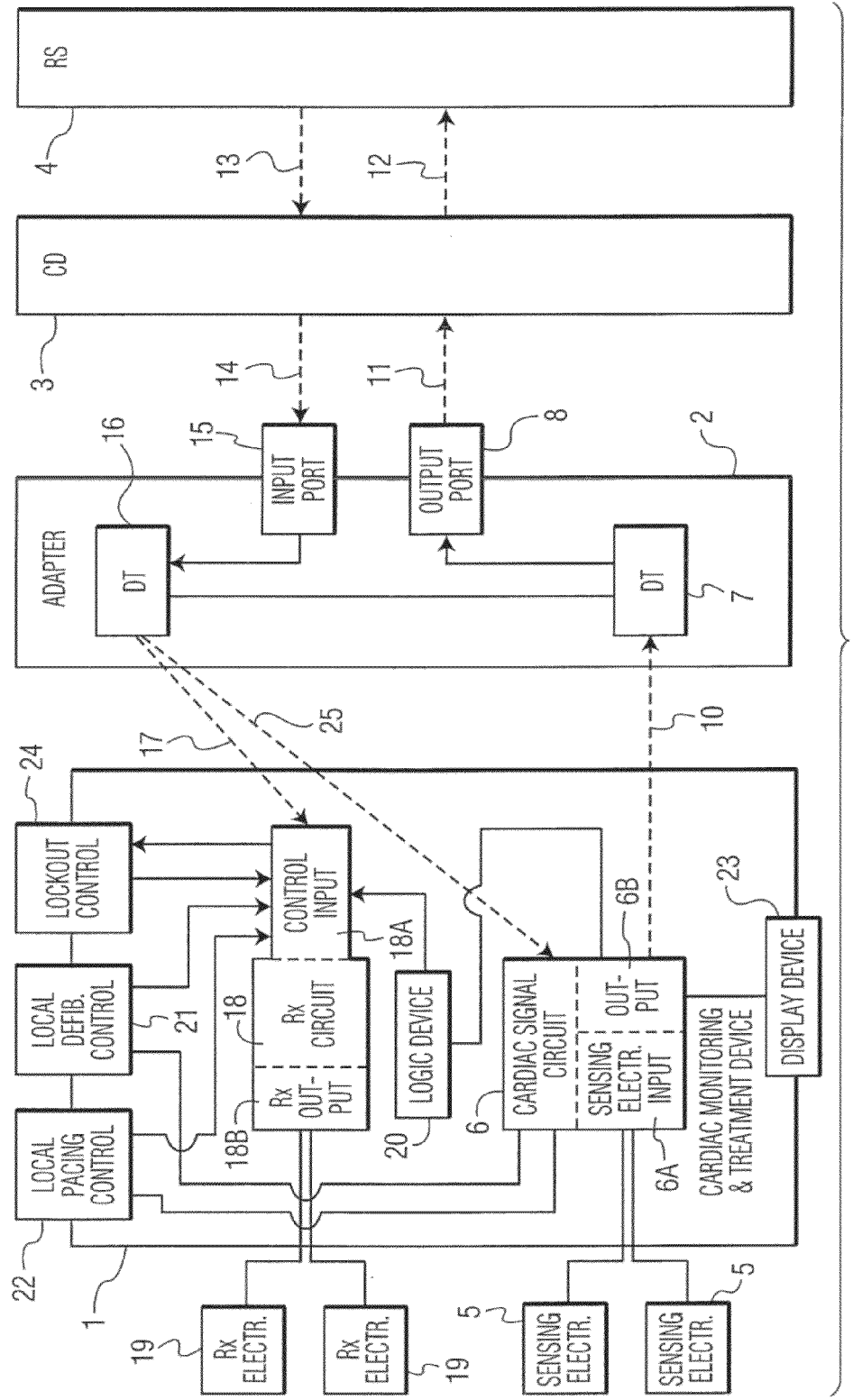
FIG. 1 is a block diagram of the cardiac resuscitation system in overview.

FIG. 1 shows an overview of a generalized version of the invention. The main components are cardiac treatment and monitoring (CMTD) device 1 and adapter (AP) 2.

The broadest overview of the path of informational and command signals between the CMTD and the remotely located MP is as follows:

Electrocardiogram (ECG) signals from a victim of a medical emergency pass from CMTD 1 to AP 2 to communication device (CD) 3 to remote station (RS) 4. A medical professional (MP) at the RS—in a location remote from the victim—receives the ECG signals, views them, and makes a decision about whether cardiac defibrillation or cardiac pacing is necessary. If either one is necessary, the MP sends one or more control signals via the route RS to CD to AP to CMTD.

CMTD 1 is a defibrillating or pacing device which has been modified so that it may communicate with a remotely located MP via an adapter 2 and a communication device 3. The adapter allows the CMTD to be compatible with the CD.

A more detailed overview of the path of informational and command signals between the CMTD and the remotely located MP is as follows:

An ECG signal is derived from two or more sensing electrodes 5. The signal is introduced to cardiac signal circuit 6 via cardiac sensing electrode input 6A. The signal is amplified and may be further processed, as is known in the art.

Second local data signal 10 from cardiac signal circuit output 6B is coupled to data translation device 7 of the adapter. Various means of achieving this coupling are possible including:
1) a hard-wired electrical signal connection: In this case, each of a) circuit output 6B, and b) the input to 7, is externalized, i.e. hardwired to a jack or port at the surface of each of 1 and 2, or to a connector at the end of an external cable; and
2) a wireless connection which may utilize a radiofrequency signal (RF), an optical or infrared signal, Bluetooth, WiFi, or another wireless internet-based connection.

7 provides any further necessary signal conditioning required to render the output of 6B appropriate as an input for communication device 3. Such conditioning may include amplification, filtering, noise reduction, decoding, encoding, decrypting and encrypting. Once accomplished the first local data signal 11 leaves the adapter via output port 8.

Adapter 2 communicates with CD 3 by either a wired or wireless connection. If the connection is wireless it may be RF, optical or infrared signal, Bluetooth, WiFi, or another wireless internet-based connection.

CD and RS, communicate via either a wired or wireless connection or a mixture of the two. If wired, it may utilize the public telephone network or a private carrier. If the connection is wireless it may utilize a public cellular network; RF communication on a medical band, on a cordless telephone frequency, on a satellite phone or a private carrier. There may be a wired or a wireless connection to the internet. Other means of communication will be obvious to those skilled in the art.

Additional description of RS is contained hereinbelow.

Utilizing one or more of the aforementioned signaling means, ECG information moves from 3 to 4 as remote data signal 12. After MP decision making, the signal which reflects that decision, remote data signal 13, is transmitted back to 3 by any one or more of the aforementioned CD-RS signaling means, and, as first local control signal 14 back to the input port 15 of the adapter. The approach to AP-CD information transfer discussed hereinabove applies to the technique of CD-AP information transfer.

The input port feeds information to another data translation device 16, which provides any necessary signal conditioning required to render the output of 3 appropriate as a control input for the CMTD. Such conditioning may include amplification, filtering, noise reduction, decoding, encoding, decrypting and encrypting. Once accomplished the second local control signal 17 exits the adapter and enters 1. Any of the routes and modalities discussed in conjunction with outgoing second local data signal 10 are possible routes and modalities for incoming second local control signal 17, as it traverses the 16 to 18A route.

Control input 18A is the entry point for control signals which determine what treatment circuit 18 does. In one embodiment of the invention, 18A functions only as a conduit for signals which explicitly control defibrillation and/or pacing (e.g. a "DELIVER SHOCK" signal); In another embodiment of the invention (see below), 18A additionally has a switching function, whereby it allows the selection of a source of control, e.g.

MP vs. a local emergency medical person;
MP vs. AED algorithm;
MP vs. AED algorithm vs. a local emergency medical person, or
MP vs. ICD algorithm.

The treatment circuit or circuits 18 controlled by 18A may be:
a defibrillator circuit; and/or
a pacing circuit.

The output of the treatment circuit 18B is applied to two or more defibrillator electrodes 19. (In the case of an implanted pacing or defibrillator device, one of these electrodes may be the "can" of the implanted device.)

When CMTD 1 is an AED which contains both an ECG data output port and a command input port it is referred to hereinbelow as "mAED". The mAED may be initially built with such ports, or suitably modified post initial manufacturing. The mAED will contain logic device 20, for analysis of ECG signals, which reach 20 along the route 5 to 6A to 6 to 6B to 20. If a shock or pacing is appropriate based on the ECG analysis, the output of 20 will be a command (to shock or pace) delivered to treatment circuit control input 18A. From this point, the command which originates in the logic device has an identical route and effect as the remotely originating command described hereinabove.

The CMTD may be a manually controlled defibrillator and/or pacing device, i.e. a device which is used by a medical doctor or emergency medical technician (each of which, hereinbelow, is referred to as "local MP"), and whose use entails the local MP making a shock/no-shock or pace/no-pace decision, and whose use may also involve the selection of shock parameters (e.g. synchronization, energy) or pacing parameters (e.g. pacing rate). In such an embodiment of the invention, the local MP will have a defibrillation control input 21 if the CMTD is a defibrillating device; There will be a pacing control input 22 if the CMTD is a pacing device. Embodiments of the invention in which 1 performs both functions are possible. The local MP will also require a display device 23, for displaying the ECG signals, allowing him to make his management decision(s).

In a device such as that described herein with more than one source of a control, it is advantageous to have a design feature which allows for the selection of a single control source. In such an embodiment of the invention, for example, if the local MP wishes to take control, he would wish to prevent or lock out control by either (a) the remote MP or (b) the logic device within the AED. This may be accomplished, as shown in FIG. 1, by having a lockout control 24 which may be inputted by the local MP. In this instance, following local MP input to 24, a signal is sent to 18A which causes it to ignore control signals from logic device 20 (if any) or signals 17 from a remote MP (if sent).

In an alternative embodiment of the invention, the remote MP may be allowed to be the source of a lockout command, giving him control priority over either a local MP or the logic device. The remote MP may send such a lockout signal 17 which arrives at control input 18A and either a) signals the control input directly, or b) signals lockout control 24, or c) both a) and b).

In one embodiment of the invention, (a) the local MP may lockout the logic device, but may not lockout the remote MP, and (b) the remote MP may lockout either or both the local MP and the logic device.

In another embodiment of the invention, (a) the remote MP may lockout the logic device, but may not lockout the local MP, and (b) the local MP may lockout either or both the remote MP and the logic device.

Besides controlling the parameters of pacing and/or defibrillation via signal (17), in yet another embodiment of the invention, a remote MP may also control the choice of pacing and/or defibrillation electrodes 19, if more than two electrodes are available. Such control signals 17 traverse the route 16 to 18A to 18 to 18B where, in this embodiment, they determine the choice of output electrodes.

In yet another embodiment of the invention, a remote MP may also control the choice of sensing electrodes 5, if more than two electrodes are available. Such control signals 25 traverse the route 16 to 6 (or 16 to 6A) where, in this embodiment, they determine the choice of sensing electrodes.

Embodiments of the invention, described hereinbelow, are possible in which the CMTD is a pacing or pacing/defibrillating device which is implanted in a patient. In this case, adapter 2, which may be either inside the body or outside the body, allows the implanted pacemaker or pacemaker-defibrillator to use a CD (such as a cellular telephone) which is external to the body to communicate with a remotely located MP. Embodiments of the invention are also possible in which all three of the CMTD, the AP and the CD are implanted in the body.

In order to assure that an unauthorized person does not communicate with the system, data translation device 16 may contain means for confirming the identification of the putative MP, in a preferred embodiment of the invention. One approach is to assign a unique identification (ID) number to each authorized MP user and store the ID numbers in 16. The remote MP could then be required to present his identification number at the start of a remote session, or with each command that he sends. If the ID number presented by the MP does not match one of the stored ID numbers, access to the system is denied. In one embodiment of the invention, the MP would be notified if access is denied; the connection in FIG. 1 from 16 to 7 indicates that such denial information would be routed from 16 to 7 to 8 to 3 and then to 4. In another embodiment, the MP could also be notified of acceptance of the ID number, by a signal sent along the aforementioned route—from 16 to 7 ... and on to 4.

Additional security could be achieved by requiring additional electronic identification. For example, the MP could also be required to submit a password; the allowable passwords would be stored in 16. Either an incorrect password or an incorrect ID number would result in rejection of access. In one embodiment of the invention, the password would be required for the MP to first gain access, and the correct ID number would need to accompany each MP command.

ID numbers and passwords (if used) could be stored in:
a) a conventional computer memory;
b) one of a number of types of memory of a "write-once-only-variety," i.e. EPROMs, EEPROMs, etc. From time to time, these units could be replaced by an on-site maintenance person, who services the adapter, or by having the entire adapter replaced from time to time, the new adapter containing the updated list of ID numbers (and, if used, passwords) in 16. In yet another embodiment, the ID number and password list could be maintained in a memory that could only be over-written by an on-scene maintenance person. Other variations in such memory access restriction methods will be obvious to those skilled in the art.

Other systems of user identification are possible. ID numbers could be changed very frequently—even during the course of a transmission; an ID number master source could supply these on a very frequent basis to known MPs and known adapter owners. Alternatively, the frequency (for transmission between CD and RS) could be shifted on a frequent basis, even during the course of a transmission, following a pattern that would be known only to authorized users. Still other user identification methods will be obvious to those skilled in the art.

Embodiments of the invention in which access denial hardware and/or software is located in the CD (instead of, or in addition to its being located in the adapter), are possible. Embodiments of the invention in which access denial hardware and/or software is located in the CMTD (instead of, or in addition to its being located in the adapter), are also possible.

An embodiment of the invention is possible in which access denial hardware and/or software is located in each of the CMTD, the AP and the CD.

In order to assure proper functioning in a system with multiple attachable and detachable components, it is desirable to have a system which assures that all components are properly attached, and, in the event of a detachment, allows for one or more of: a) notifying one or more users, who may remedy a detachment, and/or b) causing the CMTD to revert to autonomous functioning. Signaling methodology which accomplishes these tasks is discussed generally in conjunction with FIG. 2. Apparatus for one version of signaling is discussed in conjunction with FIG. 3, and further discussed in conjunction with a) the mAED, hereinbelow and b) a unit in which the CMTD and the AP are combined, also hereinbelow.

Figure 2:
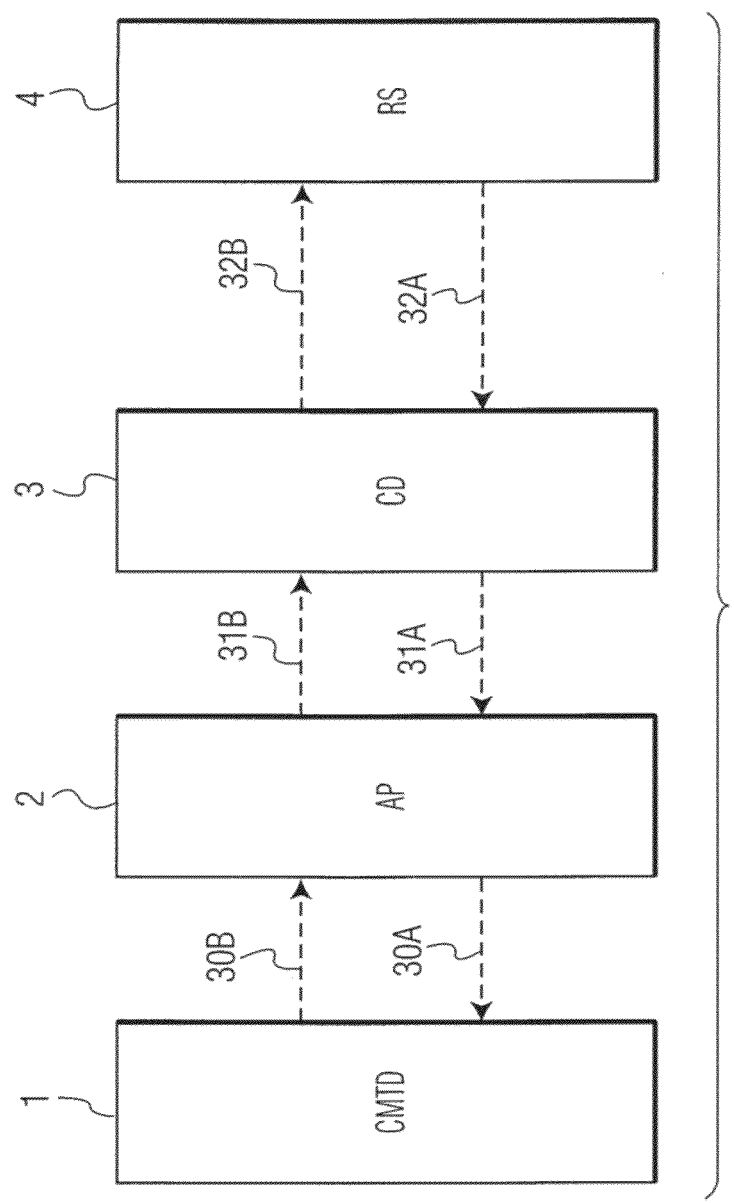
FIG. 2 is a block diagram showing some possible pairs of system components between which a handshake or communication confirmation may occur.

Referring to FIG. 2, each of elements 1, 2, 3 and 4 function as described hereinabove. The broken lines in the figure indicate attachment signals, each of which let the downstream hardware "know"—based on receipt of that signal—that the upstream signal source is properly attached. (Hereinbelow, "downstream" refers to the 4 to 3 to 2 to 1 direction, i.e. 3 is downstream from 4. "Upstream" refers to the opposite direction, so that 4 is considered to be upstream from 3.) Thus the receipt of signal 30A lets the CMTD know that the AP is properly attached to it, while receipt of signal 30B lets the AP know that the CMTD is properly attached.

If the system uses the detection of a failure of attachment as a trigger for reversion of a CMTD to automatic functioning (e.g. defibrillation management by logic device 20), it requires a means by which a 2-3 detachment (i.e. a detachment of 2 from 3) or a 3-4 detachment (i.e. a detachment of 3 from 4) is communicated to 1. Various approaches to this will be clear to those skilled in the art. One approach is to detect a detachment upstream (e.g. at the 2-3 link [the link between 2 and 3]), and communicate it downstream (e.g. from 2 to 1). A second approach is to consider complete attachment as requiring all three links (1-2, 2-3 and 3-4) to be intact, and therefore design the system so that signals pass from 4 to 3 to 2 to 1; In this case, failure to receive a signal at 1 implies an upstream detachment and triggers the automatic functioning of 1, perhaps until signals from 4 are restored. Specifically the aforementioned approach would entail:

1) signal 32A sent from 4 to 3;
2) receipt of 32A by 3 triggers 3 to send 31A to 2;
3) receipt of 31A by 2 triggers 2 to send 30A to 1.

In this case, the arrival of 30A at 1 indicates an intact connection between each of 1-2, 2-3 and 3-4. Embodiments of the invention in which a signal repeatedly is sent from 4, intended to signal CMTD 1, are possible, so that the failure to receive 30A indicates that disconnection occurred somewhere upstream in the interval since the previously received signal. Embodiments of the invention with more complex downstream signaling are possible, e.g. one in which if 3 (or 2) failed to receive a timely signal from 4 (or 3), it would send a downstream signal indicating the failure, thereby localizing the source of the failure. This information could be useful to a person using the CMTD.

It could also be useful to convey attachment information in the upstream direction. All of the same concepts and means for downstream notification of an attachment failure, apply to upstream notification. In short, the sequence would be:

1) signal 30B sent from 1 to 2;
2) receipt of 30B by 2 triggers 2 to send 31B to 3;
3) receipt of 31B by 3 triggers 3 to send 32B to 4.

Notification of the remote MP of an attachment failure could trigger one or more of:

a) dispatching local 9-1-1 to the scene of the CMTD;
b) attempts at troubleshooting electronically, from the remote site;
c) use of backup communication means, if available, at the remote MP end; and
d) use of backup communication means, if available, at the CMTD end, which may be activated by either the local user, or electronically by the remote MP.

Still more complex signaling arrangements are possible. For example, a continuously or semi-continuously circulating signal may traverse the route 4 to 3 to 2 to 1 to 2 to 3 to 4 to 3 to . . . . In this embodiment, An initial signal may be sent from 4 which, if it reaches 1 triggers a return signal. If the return signal reaches 4, it triggers another signal from 4 to 1. The process continues repeatedly until either the session ends, or a break in communications occurs. Because of the circulating feature of the signals, when such a break occurs, both the remote MP and the CMTD (and/or the CMTD operator) will be informed of its occurrence. (The initial signal could also be sent from the CMTD.)

Still other signaling arrangements would let either 4 (or the 4 operator) and/or 1 (or the 1 operator) localize the point of detachment:

a) Each of 4, 3 and 2 send their own downstream signals which are coded so that the downstream recipient can identify the signal source. In this arrangement, if 1 receives signals from 2, and not from 3 and 4, it indicates a 2-3 detachment.

b) Each of 1, 2 and 3 send their own upstream signals which are coded so that the upstream recipient can identify the signal source. In this arrangement, if 4 receives signals from 2, and not from 1, it indicates a 1-2 detachment.

c) Arrangements with a continuously circulating signal in which, in addition to the circulating signal, either the MP or the CMTD may cause either the AP or the CD to echo an incoming signal; This would let the MP or the CMTD identify the point of detachment. For example, if the remote MP failed to receive the circulating signal, and then sent out an echo signal which successfully traverses the route 4 to 3 to 4, and then sent out another echo signal which did not successfully traverse the intended route 4 to 3 to 2 to 2 to 4, it would be clear to the remote MP that the site of the detachment was 2-3.

For hardwired connections involving multi-pin connectors, it would be possible to have a communication failure involving some pins, which would not be apparent if the pins carrying the attachment signals were properly connected. Methods for detecting such situations include:

having multiple connectors between adjacent components (e.g. 2 and 3) at different geometric locations, each carrying an attachment signal; and having an attachment signal routing routine where the attachment-signal-carrying pins are continuously varied, so that ultimately, any inadequately connected pair of pins would be detected.

Still other connection confirmation methodologies and routines will be obvious to those skilled in the art.

Figure 3:
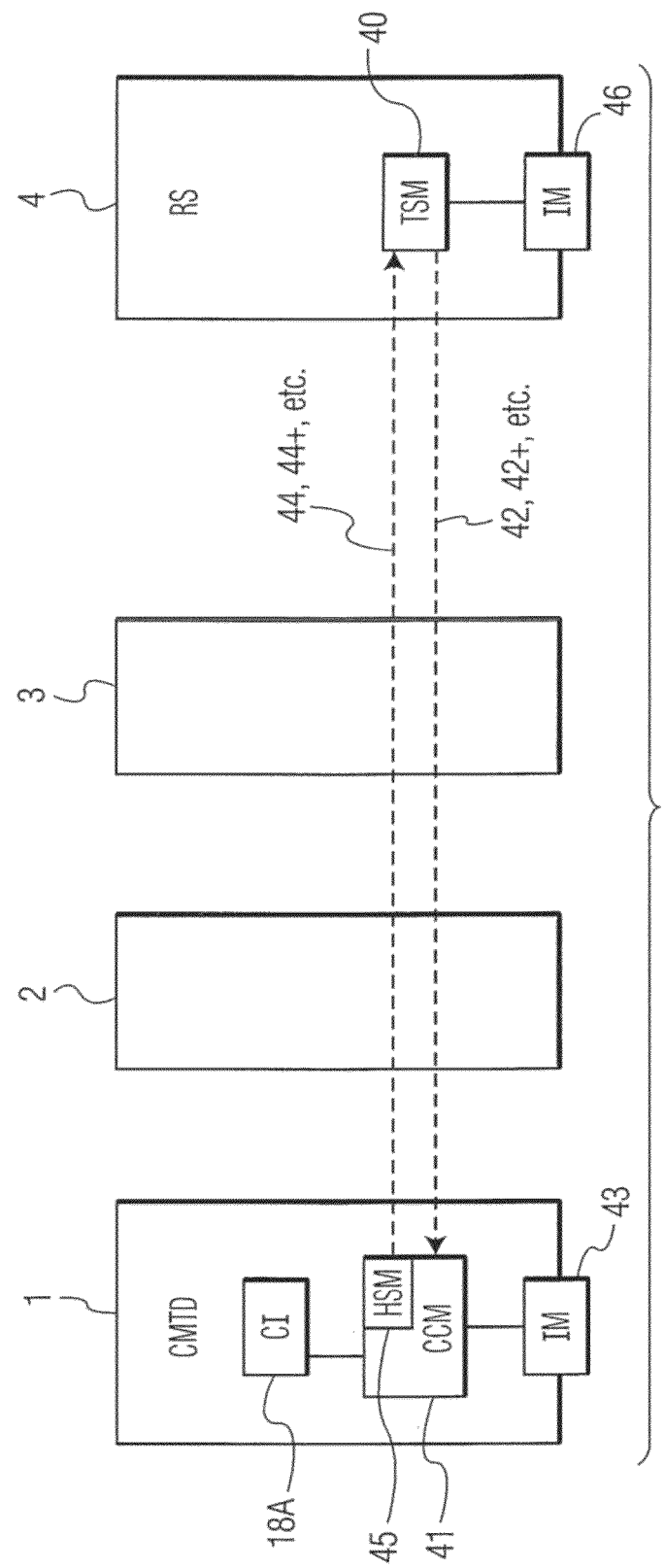
FIG. 3 is a block diagram showing a handshake or communication confirmation between a cardiac monitoring and treatment device and a remotely located transmitter/receiver device.

FIG. 3 shows an example of communication confirmation signaling arrangement. Test signal means 40 generates a test signal 42 which, in the presence of proper attachment between RS 4 and CD 3, is communicated to 3, and, in the presence of proper attachment between CD 3 and AP 2, is communicated to 2, and in the presence of proper attachment between AP 2 and CMTD 1 is communicated to communication confirmation means 41 in 1. In the absence of 42, 41 signals control input 18A which transfers control from the remote MP to either the logic device in the CMTD or to a local MP, if present. Variations of this embodiment include:

a) one in which the test signal is repeatedly generated and in which 41 indicates a communication failure if a test signal is not received at the expected interval after the last received test signal;

b) one in which a break in communication is indicated by CMTD indication means 43. 43 may be a display screen, a tone generating apparatus, an alarm, etc. 41 and the display screen may also be configured to indicate adequate communication status; and c) one in which 45 emits signals on a fixed schedule (i.e. not based on whether it receives any signals). With this arrangement, in the presence of intact attachments of each upstream pair of components, there would be a repetitive receipt of such signals by 40; and a break in the received signals would indicate a detachment; This approach could be used in addition to sending test signals 42 downstream;

d) one in which:

(i) the receipt of 42 by 41 results in the generation of a handshake signal 44 by handshake generating means 45. The handshake signal traverses the system in the upstream direction. In the presence of proper attachment between each of 1 and 2, 2 and 3, and 3 and 4, the signal arrives at 40 in RS 4. Non-arrival of an expected return signal 44 (such expectation based on 40 having sent out signal 42) triggers a message from 46 at the remote station 4. Optionally, arrival of 44 at 4 triggers a status message on RS indication means 46 (tone or screen message, etc.); and (ii) at fixed intervals of time thereafter, 40 generates additional test signals, for repeatedly evaluating the integrity of each attachment;

e) one in which:

(i) the receipt of 42 by 41 results in the generation of a handshake signal 44 by handshake generating means 45. The handshake signal traverses the system in the upstream direction. In the presence of proper attachment between each of 1 and 2, 2 and 3, and 3 and 4, the signal arrives at 40 in RS 4. Non-arrival of an expected return signal 44 (such expectation based on 40 having sent out signal 42) triggers a message from 46 at the remote station 4. Optionally, arrival of 44 at 4 triggers a status message on RS indication means 46 (tone or screen message, etc.);

(ii) the receipt of 44 by 40 triggers the next test signal, 42+ [as opposed to the method of (d) above, where the next test signal is not triggered by the arrival of 44, but instead occurs a fixed interval after the previous test signal was emitted];

(iii) the receipt of 42+ by 41 triggers the next handshake signal, 44+;

(iv) the receipt of 44+ by 40 triggers still another test signal, 42++;

(v) the process of nth test signal generating the nth handshake signal, and the nth handshake signal generating the (n+1)th test signal continues until the event for which communication is required has ended, or until there is a break in communication.

Figure 4:
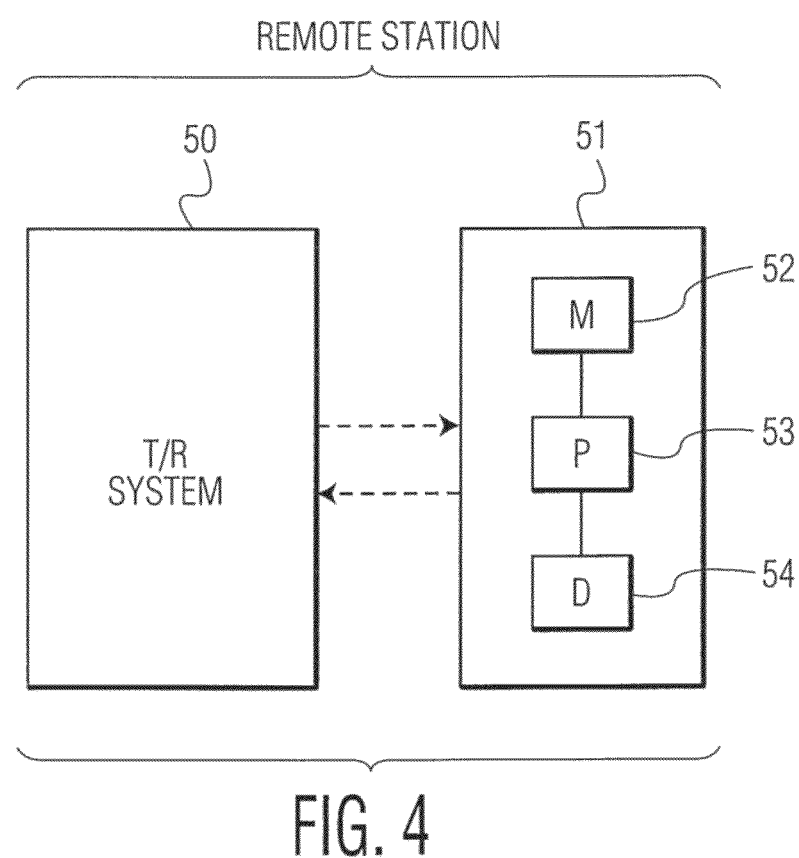
FIG. 4 is a block diagram of one embodiment of the remote station.

FIG. 4 shows one possible embodiment of a remote station 4. It consists of a) transmitting and receiving apparatus 50; and b) a computer 51 linked to 50.

50 communicates with CD 3, as shown in FIG. 1 (not shown in FIG. 4). The communication between 50 and 51 may be 'hard-wired,' radiofrequency, Bluetooth, WiFi and infrared/optical signals, through the Internet (via a wired or wireless connection) or through the public telephone system (wired or wireless).

51 contains a processor 53 linked to a) memory 52 and b) a display device 54. Not shown in the figure are one or more input devices, a power supply and other items commonly found in a computer, as is well known in the art.

The computer 51 allows the MP to input commands, and to store information about:

the current event, this victim's prior events [if any] entailing use of the remotely controlled apparatus, this victim's medical history, medical practice in general, legal aspects of arrest and emergency management, in general advanced legal directives that pertain to this victim, the CMTD which is downstream [including prior malfunctions (if any) of the model of CMTD, and of the particular CMTD in current use], the AP which is downstream, the CD which is downstream, the competence of a particular local MP who is using 1, 2 and 3, the availability of emergency services in the vicinity of the victim, and the availability of other remote MPs, should he find himself needing to handle a larger number of simultaneous tasks than is practical.

The computer also allows the MP to more carefully analyze a complex or difficult to diagnose electrocardiogram, either by enlarging it, making on-screen measurements, filtering it in different ways, or comparing it to a database.

The computer allows the MP to select from a menu of commands to be inputted into the CMTD. These may be as simple as shock vs. no shock, or complex packages of commands (e.g. perform anti-tachycardia pacing with a cycle length which is 84% of the tachycardia cycle length, burst duration 8 beats, total attempts=3, inter-burst 10 msec. cycle length decrement, minimum paced cycle length=230 msec.).

The computer also allows the MP to select voice prompts, if necessary (e.g. if available bandwidth for communication with the CMTD is very narrow) which may be stored in the CMTD.

The computer also allows the MP to select a video prompt, e.g. for the delivery of CPR instructions to a bystander at the arrest scene; The video prompt may be stored in 52, in the CMTD, or at another location with which 51 can communicate.

Acknowledgment is made of the concept that, as cellular telephones and personal communication devices become progressively more sophisticated, the distinction between a communication device and a communication device plus computer becomes somewhat arbitrary. We are already at a point where essentially all commercially available communication devices have each of the items in 51, as well as a power supply and one or more input devices. Thus, the combination of 50 and 51 may be a cellular telephone, a Blackberry device, etc.

The combination of the 3 components:

CMTD,

AP, and

Figure 5A:
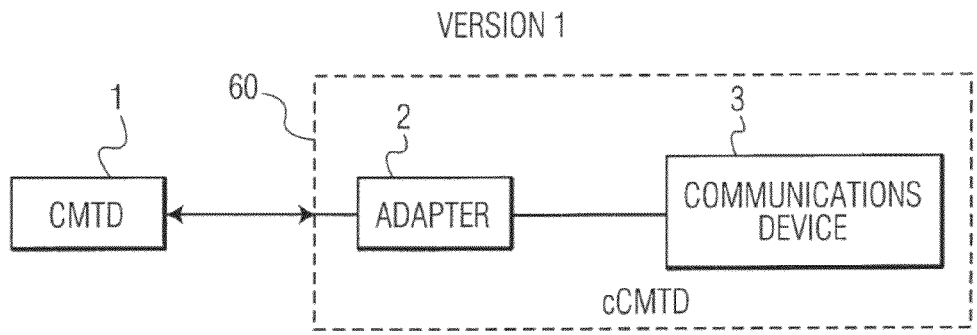
FIG. 5A is a block diagram of the system showing how the combination of an adapter device and a communication device may be linked.
Figure 5B:
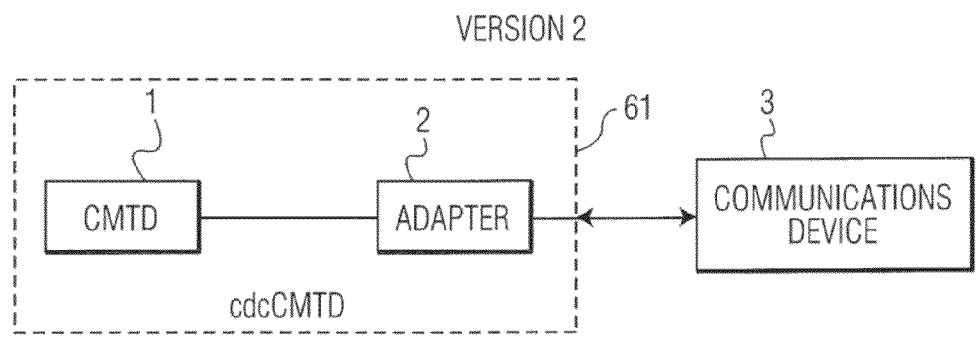
FIG. 5B is a block diagram of the system showing how the combination of an adapter device and cardiac monitoring and treatment device may be linked.
Figure 5C:
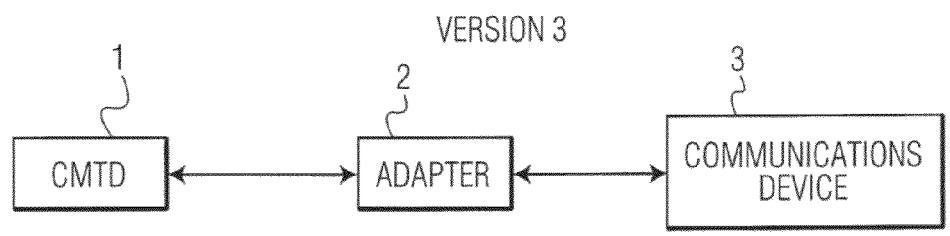
FIG. 5C is a block diagram of the system showing how the cardiac monitoring and treatment device, an adapter and a communication device may each be physically separated.

CD, form a complete remotely controlled monitoring and treatment device (RCMTD). Only the addition of a remote station is necessary to assemble the complete system. FIGS. 5A, 5B and 5C show three ways in which the three aforementioned components may (or may not) be assembled.

FIG. 5A, version 1, shows the linkage of AP 2 and CD 3 within housing 60. The combined AP and CD is referred to as the cCMTD—indicating communication and control unit of a cardiac monitoring and treatment device.

Symbolic representations of the aforementioned functional relationships shown in FIG. 5A, in which the components of the cCMTD include the adapter and the communications device, are:

*AP*+CD=*c*CMTD, and

*c*CMTD+CMTD=RCMTD.

In the case where an AED is being upgraded to a remotely controllable defibrillator, the above symbolic statements would be written as:

AP+CD=cRCD, and cRCD+mAED=RCD, where cRCD refers to the communication and control unit of a remotely controlled defibrillator, the other terms having been defined hereinabove.

FIG. 5B shows another way, version 2, of distributing the components of the RCMTD. It shows the incorporation of a CMTD 1 and an adapter 2, each with functionality similar to that described hereinabove, combined within one housing to form a communications device compatible CMTD 61, "cdc-CMTD." A communications device 3 such as a cell phone may be attached to the cdcCMTD to form the complete RCMTD.

Symbolic representations of the aforementioned functional relationships shown in FIG. 5B, in which the components of the cdcCMTfD include the CMTD and the AP, are:

CMTD+AP=cdcCMTD, and cdcCMTD+CD=RCMTD.

In the case where an AED is being upgraded to a remotely controllable defibrillator, the above symbolic statements would be written as:

mAED+AP=cdcAED, and cdcAED+CD=RCD, where cdcAED refers a communication device compatible AED, the other terms having been defined hereinabove. FIG. 5C shows another way, version 3, of distributing the components of the complete RCMTD. It shows each of the three components of the RCMTD,
a) the CMTD 1,
b) the AP 2, and
c) the CD 3
as "stand-alone" units.

A symbolic representation of the aforementioned functional relationships shown in FIG. 5C, in which each of the three components of the RCMTD is separate, is:

CMTD+AP+CD=RCMTD.

In the case where an AED is being upgraded to a remotely controllable defibrillator, the above symbolic statement would be written as:

mAED+AP+CD=RCD.

Example

System with Unified Adapter and Communication Device

Figure 6:
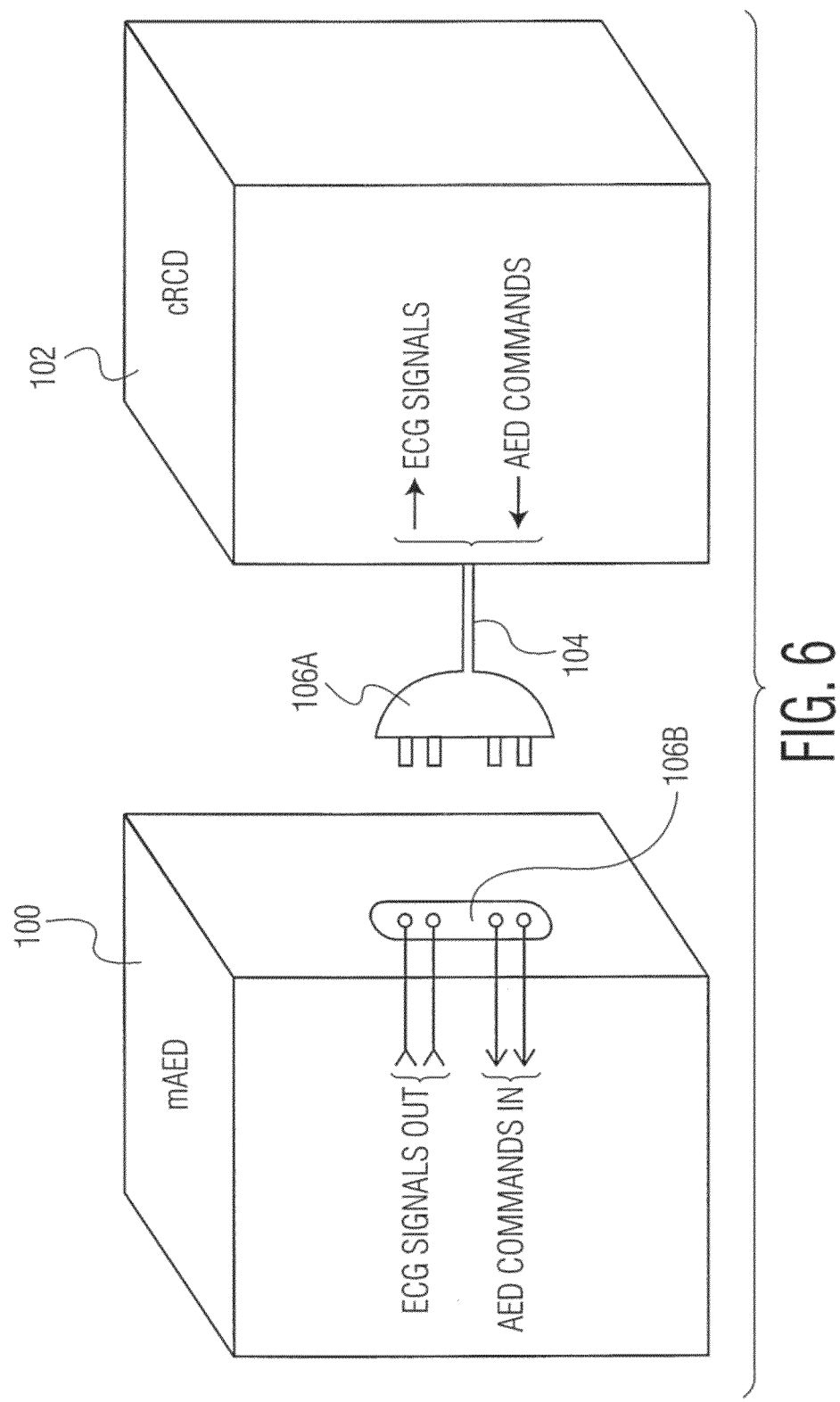
FIG. 6 is a block diagram showing a modified AED which may be directly connected to a communication device.

FIG. 6 shows a specific example of version one, referred to in FIG. 5A, in which the CMTD is a modified AED. It illustrates a schematized view of a method and apparatus for adapting automatic external defibrillators so that they may be remotely controlled with minimal modification. The requirements for constructing such a system are:

1) An AED design modification which "externalizes" (i) AED ECG signals and (ii) defibrillation control signal circuit and/or command access points, so that they become (i) AED telemetry output and (ii) AED control input; Units with such modifications are referred to as modified AEDs (mAEDs).

2) Coupling the mAED outputs and inputs to a device or devices which allow for electronically extending these inputs and outputs to a remote MP, via a communication system. This may be accomplished by coupling the mAED inputs and outputs to either:
a stand-alone AP which is coupled to a stand-alone CD, or to
a single device, a cRCD (as defined hereinabove) which combines the components and functionality of each of the AP and the CD.

Referring again to FIG. 6, 100 is a modified automatic external defibrillator. The modification consists of the addition of external access to:
1) ECG signals from a victim attached to the mAED; and
2) control inputs which allow control of the defibrillator (and pacing) circuitry within the mAED.

As shown in the figure, the ECG and control signals may be coupled to a cRCD 102 by cable 104 and schematically shown connector 106A and 106B.

Following the coupling of connectors 106A and 106B, remote control of the mAED is achieved according to the sequence:
1) victim ECG signals from mAED 100 to cRCD 102 (via the sequence 100→106B→106A→104→102);
2) ECG signals from cRCD to remotely located medical professional (MP);
3) MP analyzes the ECG signals, and decides on the need for defibrillation, pacing (in the case of a 100 unit with capability to pace as well as defibrillate) or neither;
4) if appropriate, MP sends defibrillation or pacing control signals;
5) control signals, if any, traverse the route from cRCD 102 to mAED 100 (via the sequence 102→104→106A→106B→100); and
6) depending on whether a defibrillation or pacing signal has been sent, the victim may receive defibrillation or pacing stimulation.

Although the connectors 106A and 106B show one pair of wires and one pair of pins for each of two signals, formats involving a greater or lesser number of channels and a greater or lesser number of pins are possible, as is known in the art.

Figure 7:
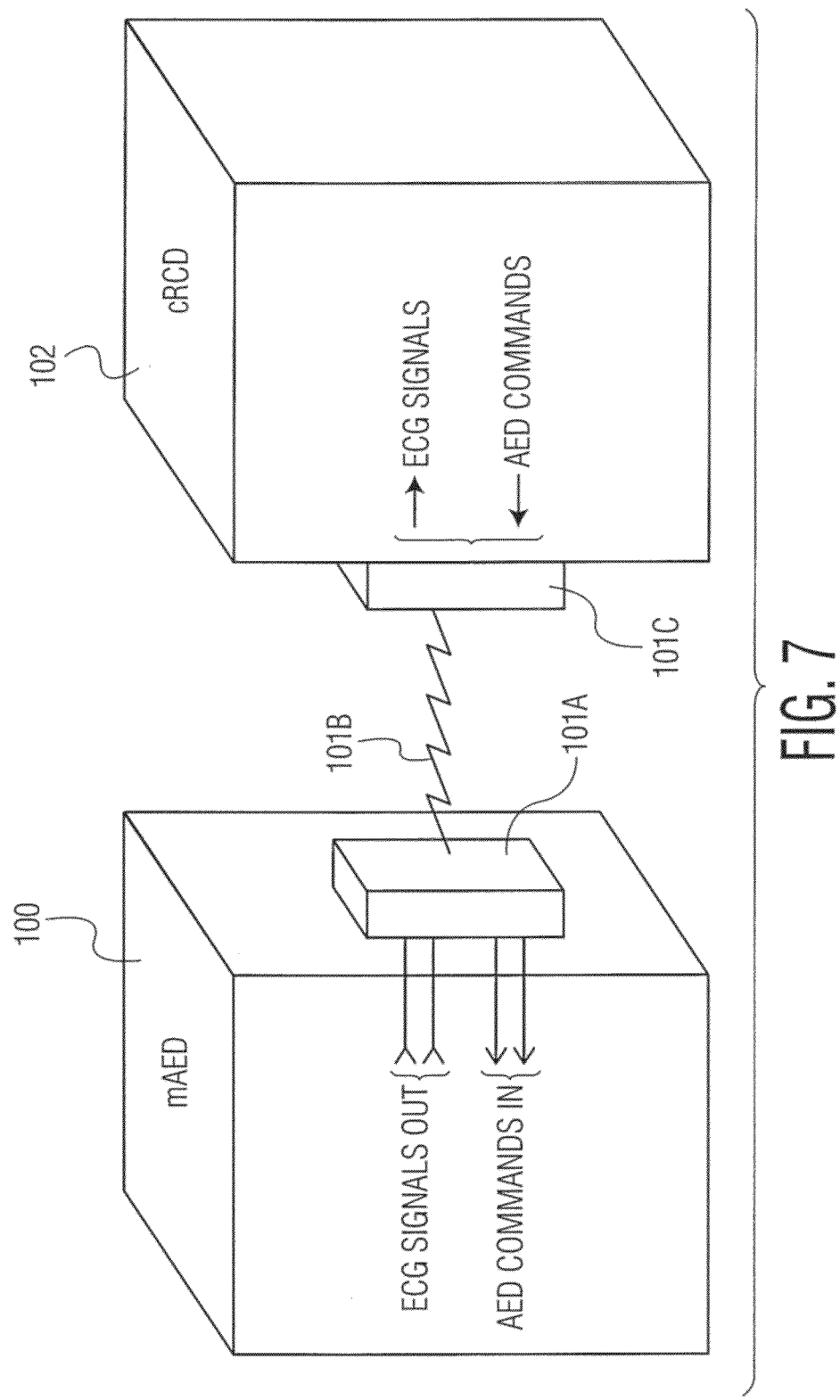
FIG. 7 is a block diagram showing a modified AED which may be connected to a communication device using wireless means.

As shown in the example in FIG. 7, the connection between the mAED and the cRCD need not be hard-wired. Electromagnetic signals such as radiofrequency, Bluetooth, WiFi and infrared/optical signals may link the mAED and the cRCD. As shown in the figure, mAED 100 may use associated signaling unit 101A to send signal 101B which may be RF, microwave, infrared, etc. to the cRCD signaling unit 101C. 101C is coupled to cRCD 102. Signaling in the opposite direction proceeds along the path 102→101C→101B→101A→100.

Two types of mAEDS are:
1) mAED type I, wherein the modification (which allows electrical coupling to takes place) is made post-AED production; and
2) mAED type II, wherein the modification is built in at the time of production.

Figure 8:
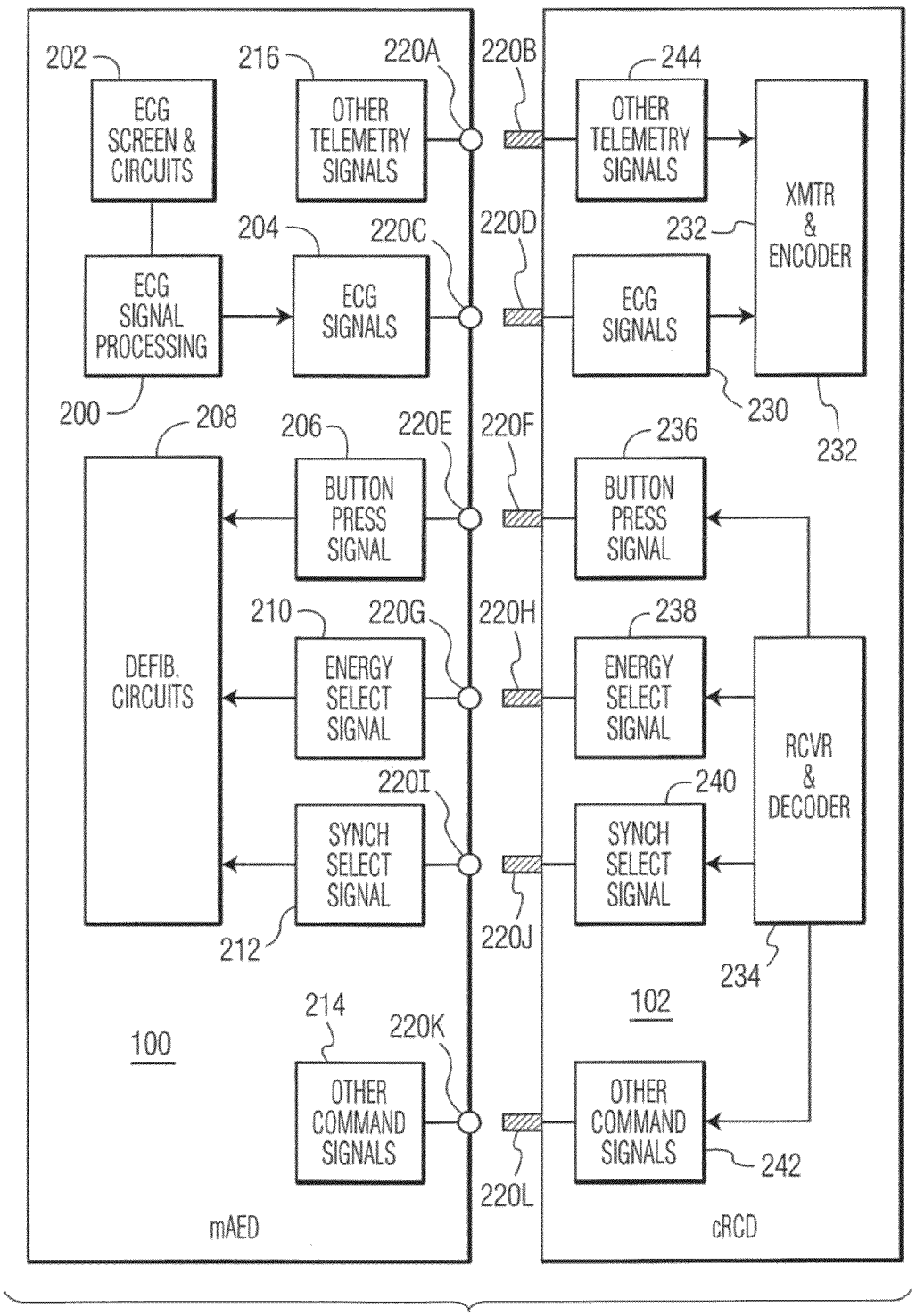
FIG. 8 is a block diagram showing the components of a modified AED and a companion communication device.

FIG. 8 shows a more detailed view of the components of an embodiment of the mAED 100 and their interaction with those of an embodiment of the cRCD 102. Victim ECG signals are processed at 200 (electrode inputs not shown in the figure), and formatted and optionally displayed at 202. Signals from 200 are also made available for coupling to the cRCD at 204. In the coupling arrangement shown, the ECG signal gets to the cRCD via female/male pin arrangement 220C/220D. Many other possible connector arrangements will be familiar to those skilled in the art. The ECG signals are optionally further processed at 230 within the cRCD. From 230, they pass to 232 where they are encoded, possibly encrypted and transmitted to a MP.

If the MP determines that the victim's heart rhythm is ventricular fibrillation, or a ventricular tachycardia which requires a shock (There are non-shock-requiring VTs.), he may send a command signal ("a button press signal") which causes the AED to shock the victim. The button press signal path would be: from MP to receiver and decoder 234 (decryption here, if necessary), to optional further signal processing within the cRCD at 236, to the mAED via connectors 220F and thence 220E (other connector arrangements possible), to optional further signal processing within the mAED at 206, to defibrillator circuits 208. In a preferred embodiment of the invention, the MP would also be able to override a defibrillation command signal which originates in the AED logic device, as discussed hereinabove in conjunction with FIG. 1.

In embodiments of the invention in which the MP also controls the energy of the defibrillator pulse, the MP may send a pulse energy selection signal which traverses the path: 234→238→220H→220G→210→208. In embodiments of the invention in which the MP also controls the shock synchronization, the MP may send a synchronization selection signal which traverses the path: 234→240→220J→220I→212→208.

The MP may send a variety of other commands and signals. These may include:

1) additional parameters of defibrillation pulse, such as:
   a) pulse peak and/or leading edge voltage;
   b) pulse mean voltage;
   c) pulse shape, as defined by voltage vs. time;
   d) pulse width;
   e) tilt (as is known in the art); and
   f) the number of phases within the defibrillator pulse; and
2) commands to a pacing circuit, such as:
   a) pacing rate:
   b) pacing voltage;
   c) pacing pulse width;
   d) pacing pulse shape;
   e) pacing mode;
   f) pacing sensitivity; and
   g) anti-tachycardia pacing signals, to attempt termination of a VT.

In embodiments in which the MP controls pacing and defibrillation, pacing control would be achieved with a system whose design is analogous to elements 208+206/210/212, which control defibrillation.

3) commands to control a chest compression device (as discussed in Ser. No. 10/460,458; and in Ser. No. 11/502,484);
4) voice-carrying signals;
5) signals which control the audio output from (e.g. volume control) and/or audio input to (e.g. microphone gain) the mAED;
6) signals which control voice prompt selection;
7) signals which contain text messages;
8) signals which control video prompt (i.e. video images stored within the mAED or cRCD) selection;
9) video carrying signals, such as:
   a) images of the MP; and
   b) images (either stored or live) intended for teaching purposes;
10) signals which control the mAED video display (e.g. brightness on mAED video screen) and/or video input to the mAED (e.g. input to a mAED videocamera);
11) signals which download new software into the mAED;
12) signals which are intended for test purposes—i.e. MP (or other non-medical personnel) testing of:
   a) the mAED; and
   b) the connections between the mAED and the cRCD; and
13) signals which are intended for teaching purposes during a non-emergency event, which may include:
   a) cRCD and mAED setup information; and
   b) teaching information related to the management of medical emergencies.

The path of the aforementioned commands are indicated in the figure as traversing the route 234→242→220L→220K→214. From 214, the command signal would pass to the appropriate target, e.g. to defibrillator circuits 208 in the case of defibrillator controlling commands, and to audio signal processing and amplification circuitry (not shown in the figure) in the case of a voice message to the either the victim, or an "enabler" who uses the apparatus to aid a victim.

Signals in addition to ECG signals, i.e. other telemetry signals, which may be sent from mAED to cRCD and thence to the remotely located MP may include:

1) confirmation signals indicating:
   a) defibrillator charging;
   b) defibrillator shock delivery; and
   c) mAED receipt of MP commands;
2) audio signals from either the victim, or an enabler;
3) video signals showing either the victim, or the performance of an enabler;
4) battery voltage for one or more mAED batteries;
5) signals indicating the results of testing done to evaluate the integrity/proper function of mAED circuitry;
6) signals, if available, indicating victim physiologic parameters which may include:
   a) blood pressure;
   b) blood oxygen saturation;
   c) end-tidal expired carbon dioxide;
   d) respiratory rate, as assessed by chest wall impedance measurements;
   e) body temperature; and
   f) electroencephalogram signals; and
7) chest wall impedance, which may be measured:
   a) prior to a defibrillation shock; and
   b) during a defibrillation shock.

The path of the aforementioned other telemetry signals are indicated in the figure as traversing the route 216→220A→220B→244→232. The telemetry signal reaches 216, from the appropriate source, e.g. from defibrillator circuits 208 in the case of defibrillator charging and, possibly, shock delivery confirmation signals, and from audio signal processing and amplification circuitry (not shown in the figure) in the case of a voice message from the victim or enabler.

In one embodiment of the invention, proper linkage and communication between the mAED and the cRCD may be confirmed on an intermittent or continuous basis by a series of handshake signals. In the event of an interrupted connection, indicated by an interruption in handshake signals, non-mutually exclusive options would include:

1) notifying the enabler and/or victim;
2) notifying the MP;
3) returning control of the defibrillator circuits to the AED logic device (i.e. the AED then functions as a conventional [v.i.z. autonomous] AED, with the AED logic circuits controlling all aspects of AED function); and
4) continuing to try to re-establish a proper handshake.

Figure 9:
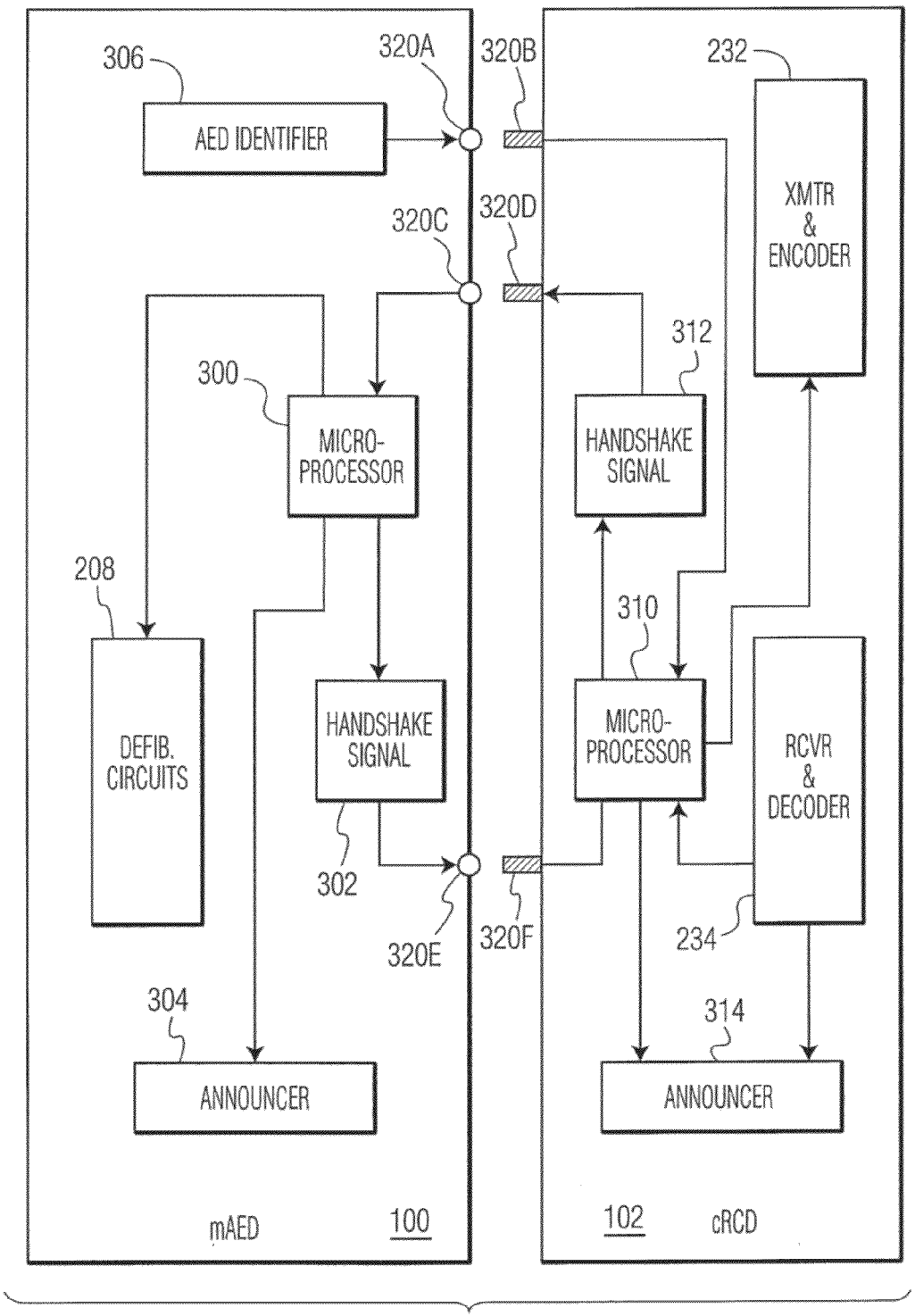
FIG. 9 is a block diagram showing the components of a modified AED and a companion communication device, with specific attention to the process of communication confirmation between these sub-units.

Referring to FIG. 9, mAED microprocessor 300 generates a handshake signal 302/(a) [the "(a)" of "302/(a)" is intended to indicate the first of a sequence of signals collectively referred to as 302, with the next one after 302/(a) referred to as "302/(b)", etc.] which, if connection 320E→320F is intact, is passed to cRCD microprocessor 310. Receipt of first handshake signal 302/(a) by 310, causes 310 to generate handshake signal 312/(a) [the 312 terminology is the same as the aforementioned 310 terminology] which, if connection 320D→320C is intact, is passed to mAED microprocessor 300. The handshake cycle continuously repeats, as long as the aforementioned mAED-cRCD connections are intact.

In the event that cRCD microprocessor 310 does not receive an expected handshake signal, it may:

1) notify the enabler and/or victim by causing a signal to be sent to announcement components 314. These components may include audio circuitry and a speaker, or a text message associated with an alarm signal;

2) notify the MP by causing a signal to be sent to transmitter 232 via an encoder; and 3) attempt to send a signal 312/(b*) to the mAED microprocessor indicating that the cRCD microprocessor did not receive the previous/expected handshake signal from the mAED. This 312/(b*) signal may cause the mAED to (i) attempt/make a repeat handshake transmission to the cRCD; and/or (ii) send a signal to defibrillator circuits 208 to switch to conventional AED function (i.e. no MP control).

In the event that mAED microprocessor 300 does not receive an expected handshake signal, it may:

1) notify the enabler and/or victim by causing a signal to be sent to announcement components 304. These components may include audio circuitry and a speaker, or a text message associated with an alarm signal;

2) send a signal to defibrillator circuits 208 to switch to conventional AED function (i.e. no MP control); and 3) attempt to send a signal 302/(b*) to the cRCD microprocessor indicating that the mAED microprocessor did not receive the previous/expected handshake signal from the cRCD. This 302/(b*) signal may cause the cRCD to (i) attempt/make a repeat handshake transmission to the mAED; and/or (ii) notify the MP by causing a signal to be sent to transmitter 232 via an encoder.

Handshake signals 312 of FIG. 9 corresponds to signal 30A of FIG. 2; Handshake signals 302 of FIG. 9 corresponds to signal 30B of FIG. 2.

In an embodiment of the invention in which the communication confirmation process extends from the RS to the mAED, the signal path would be RS to 234 (by a signal corresponding to signal 32A of FIG. 2), to 310, giving rise to signal 312, to 320D, to 320C, to 300. In an embodiment of the invention in which the communication confirmation process extends from the mAED to the RS, the signal path would be 300, giving rise to signal 302, to 320E, to 320F, to 310, to 232, and then to the RS (by a signal corresponding to 32B of FIG. 2).

Many additional types of handshake signals and handshake signal formats will be familiar to those skilled in the art.

Referring again to FIG. 9, a preferred embodiment of the invention may include an AED identifier signal generator 306. This would allow the cRCD to identify the brand and model of mAED to which the cRCD has been connected, which would allow the cRCD to accommodate such issues as signaling and control formats, voltages, and even pin arrangements particular to certain mAED brands and models. The AED identifier signal is sent to the cRCD microprocessor along the path: 306→320A→320B→310. AED model identification may also be passed along to the MP.

The transmitter 232 and receiver 234 shown in FIGS. 8 and 9 may be long range (e.g. greater than line-of-sight), short range (e.g. approximately line-of-sight), or very short range (e.g. Bluetooth). Furthermore, the cRCD may (instead of, or in addition to, using a transmitter and receiver) interface:

1) with public telephone carriers (through either a hardwired connection or short range transmitter/receiver combination), with telemetry information and MP commands carried over a public telephone connection; or 2) with the internet, with a connection to the internet (and ultimately, to the MP) via either:
 a) broadband/cable (optical or otherwise);
 b) digital subscriber line or any line which is formed from a combination of individual lines; or
 c) an individual phone line.

In a preferred embodiment of the invention, the cRCD would have its own power supply; In an alternative embodiment of the invention, the cRCD could obtain power from (or supply power to) the mAED, on a continuous basis or on an as-needed basis.

FIGS. 6 to 9 and the associated specification regarding the present example could (as discussed in conjunction with FIG. 1 and the associated specification, hereinabove), besides applying to a modified AED, also apply to:
 a modified manually operated external defibrillator, as discussed in conjunction with FIG. 1, hereinabove; and
 a modified external defibrillator which has both an AED mode and a local MP-controlled (i.e. non-automatic) mode.

Example

Figure 10:
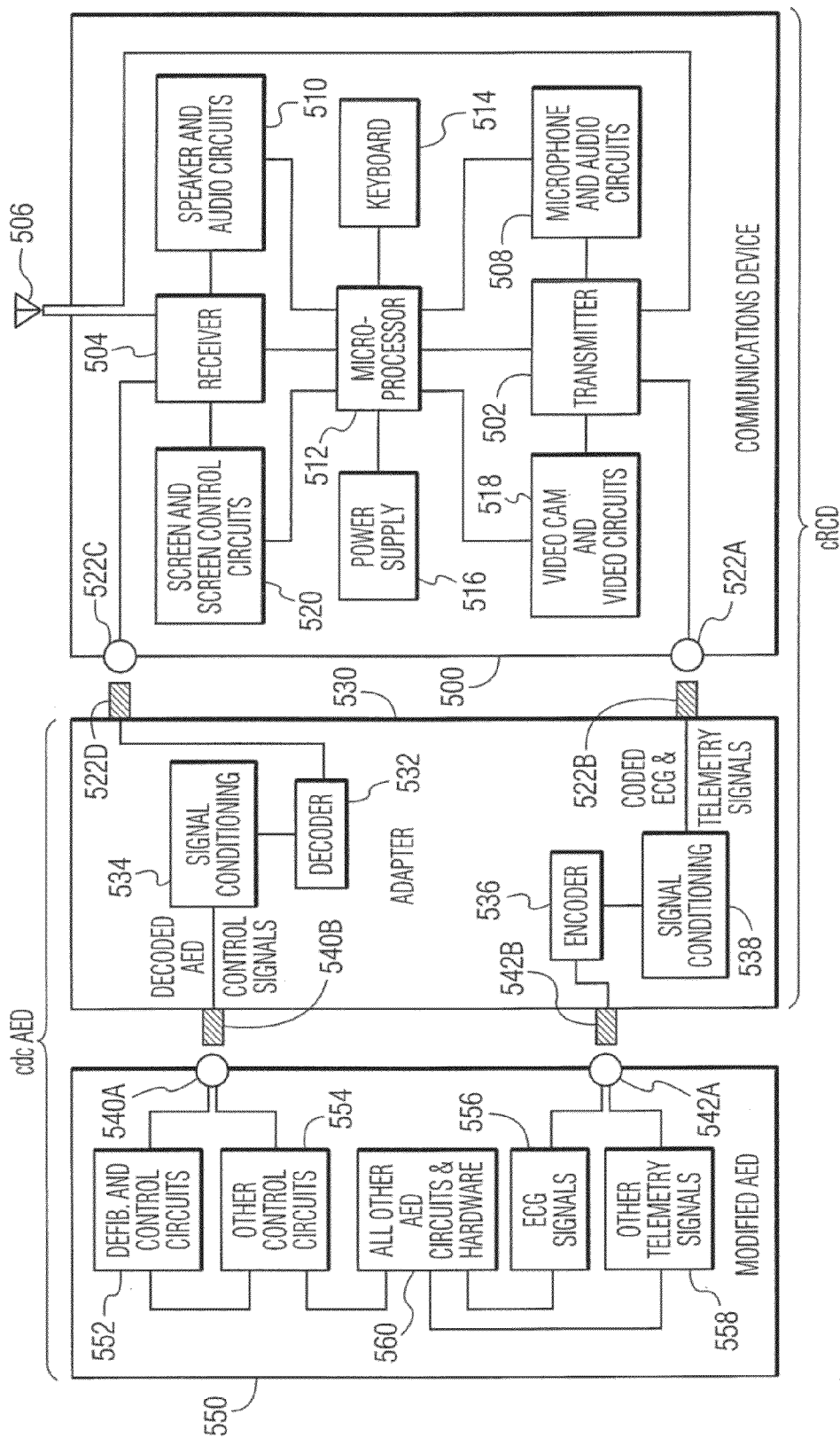
FIG. 10 is a block diagram showing the details of, and relationships among a modified AED, an adapter and a communications device.

Detailed Description of a Modified AED System which May have Various Embodiments FIG. 10 shows a schematic description of each of the components of a remotely controlled defibrillator, or RCD.

Communications device 500 includes each of the functional sub-units found in commonly available cellular telephones and other communication devices such as the Blackberry %. These include:
 a) transmitter 502,
 b) receiver 504,
 c) antenna 506,
 d) microphone and audio input circuits 508,
 e) speaker and audio output circuits 510,
 f) microprocessor 512,
 g) keyboard 514, and
 h) power supply 516.

500 may optionally include video communication equipment. This may include a video camera 518 and camera-associated circuits; and may include a screen 520 and associated screen control circuits, for viewing video images.

506 may be a single antenna which serves both 502 and 504. Alternatively, there may be one antenna for each of 502 and 504. In yet another alternative embodiment, there may be more that one antenna for the transmitter, each optimized for a different frequency. There may also be more that one antenna for the receiver, each optimized for a different frequency. Alternatively, there may be multiple antennae, each serving both 502 and 504, and each optimized for a different frequency.

512 may be a standalone microprocessor, or may consist of multiple microprocessors. Alternatively, data processing may occur in each of 502-510 and 514, 516, 518 (if present), and 520 (if present).

514 may be the standard 12 key arrangement as is known in the art, and as is present on many current-day cellular telephones. Alternatively 514 may consist of a complete alphanumeric arrangement with at least 26 letters and 10 digits. Many other keyboard arrangements and contents will be apparent to those skilled in the art.

516 may be a rechargeable cell as is known in the art. There may optionally be additional access to power from the adapter 530, or from mAED 550 via 530. These outside-the-CD sources of power may:
 a) directly power the CD;
 b) charge the cell(s) in 516; or
 c) perform both of the aforementioned functions.

The power supply is electrically connected to each of the power-requiring sections of 500 (connections not shown in the figure).

Three types of signals arrive at receiver 504 including:
 a) Signals which are intended for the control of 500, which may include:
  1) signals which control the audio output characteristics (e.g. volume control) and/or audio input to (e.g. microphone gain) of 500; and
  2) signals which control the video output characteristics from (e.g. brightness, contrast) and/or video input to (e.g. iris size, zoom) of 500;
 b) Audio, video and text signals for communicating information to the enabler/user of the unit; and
 c) Signals which control the AP or the mAED, discussed hereinbelow.

In the example shown in the figure, 500 is in electrical communication with adapter 530 via female/male pin pairs 522A/522B and 522C/522D. Alternative links between 500 and 530 are possible including:
 a) greater numbers of pins; and
 b) short-range RF or infrared linkage (e.g. as is described in conjunction with FIG. 7, and as is known in the art).

Unit 530 receives signals from 504 in 500. The signals arrive at the decoder via the path 506→504→522C→522D→532. The decoder separates out:
 1) one or more signals which control "button press" (as described in conjunction with FIG. 8 hereinabove, i.e. causing a defibrillator shock); and which may control one or more of
 2) shock synchronization;
 3) shock energy and/or voltage;
 4) shock waveform;
 5) shock electrodes (in a system with more than two electrodes);
 6) commands to pacing circuits (not shown in FIG. 10 but shown and discussed in the aforementioned applications) including:
  a) pacing rate;
  b) pacing voltage;
  c) pacing pulse width;
  d) pacing pulse shape;
  e) pacing mode;
  f) pacing sensitivity; and
  g) anti-tachycardia pacing signals, to attempt termination of a ventricular tachycardia;
 7) commands to control a chest compression device (as discussed in Ser. No. 10/460,458; and in Ser. No. 11/502,484);
 8) signals which control the video display, if any, of mAED 550;
 9) signals which download new software into the mAED;
 10) signals which are intended for test purposes—i.e. MP (or other non-medical personnel) testing of:
  a) the AP;
  b) the mAED;
  c) the connections between the CD and the AP; and
  d) the connections between the mAED and the AP;
 11) signals which are intended for teaching purposes during a non-emergency event, which may include:
  a) setup information for one or more of the mAED, the AP, the CD, the cRCD and/or the cdcAED (as defined in conjunction with FIG. 5B, hereinabove); and
  b) teaching information related to the management of medical emergencies.

The aforementioned signals may be "conditioned" at 534 and then passed to the mAED. The purpose of conditioning is to render the signal format and quality that is outputted at 532 suitable for input to the mAED. Conditioning may include a variety of processing formats including:
 a) amplification;
 b) reduction in amplitude;
 c) filtering;
 d) changing from one digital format to another;
 e) combinations of a)-d); and
 f) other methods as are known in the art.

Alternative embodiments of the invention may include:
 a) one in which there is no signal conditioning post decoder;
 b) one in which there is additional signal conditioning pre-decoder; and
 c) both a) and b).

From 534, signals exit AP and enter the mAED via pin arrangement 540A and 540B. As indicated hereinabove with respect to the electrical linkage of the CD and the AP, the electrical link may consist of:
 a) greater numbers of pins; and
 b) short-range RF or infrared linkage (e.g. as is described in conjunction with FIG. 7, and as is known in the art).

Adapter 530 also serves to transfer ECG and other data signals (both physiologic and equipment-related) from the mAED to the CD. Signals are passed from the mAED to the AP via pin set 542A and 542B. As indicated hereinabove with respect to the electrical linkage of the CD and the AP, the electrical link may consist of:
 a) greater numbers of pins; and
 b) short-range RF or infrared linkage (e.g. as is described in conjunction with FIG. 7, and as is known in the art). Signals from the mAED are encoded by 536 and conditioned at 538.

Signal conditioning in the mAED to AP to CD route serves the analogous purpose as signal conditioning in the CD to AP to mAED route, i.e. to render the signal amplitude and format acceptable to the CD (and ultimately, to the remotely located MP).

Alternative embodiments of the invention may include:
 a) one in which there is no signal conditioning post encoder;
 b) one in which there is additional signal conditioning pre-encoder; and
 c) both a) and b).

The adapter, as indicated above, may:
 a) be within the same housing as the CD, in which case the composite unit is referred to as the cRCD. In this case, at the time of use, assembly of the composite defibrillator device—i.e. the device which is capable of communication with the remote station—entails attaching the cRCD to the mAED;
 b) be within the same housing as the mAED, in which case the composite unit is referred to as the cdcAED. In this case, at the time of use, assembly of the composite device entails attaching the cdcAED to the CD; or
 c) may be a stand-alone unit. In this case, at the time of use, assembly of the composite device entails attaching the AP to the mAED and attaching the CD to the AP.

The mAED 550 contains substantially all of the components of an AED, as is known in the art. ECG signals 556 and other telemetry signals (including physiologic and equipment related telemetry) 558, output unit 550 via 542A/B. The illustration of both outputs going through the same pin is purely schematic; though it may occur as such, the use of multiple pins, and of non-contact signal transfer arrangements, as is discussed hereinabove, are possible.

Also externalized is the control of (i) the defibrillator circuits 552 (defibrillation electrodes and sensing input [if any] which would be attached to 552, not shown in the figure), and (ii) other control circuits (e.g. pacing, screen control [if any], troubleshooting and maintenance, etc.). In a preferred embodiment of the invention, the presence of an electrically intact link of both (i) the mAED to the CD (via the AP) and (ii) an intact communication link with the MP would, at 554, disable the connection of the AED logic 560 to 552. The result would be that a) the MP would have sole control of shocking (and pacing, if the pacing feature was present); and b) the AED logic/shock decision circuits would be disconnected from the defibrillator charging and shock delivery circuits.

The disconnection of the AED logic/shock decision circuits (contained within 560) from the charging and shock delivery circuits 552 could be accomplished by a control signal which either (i) originates within 554 or (ii) is delivered to 554 when the proper connections have been established. The establishment of the proper connections may be confirmed by a handshaking process which is described hereinabove and hereinbelow, or by other methods which will be obvious to those skilled in the art.

Embodiments of the invention without the aforementioned disconnect of AED logic from AED shocking circuits are possible. In this instance, either the mAED or the remotely located MP could decide to deliver a shock. This might be particularly useful if the mAED was operated by a trained person such as a physician or emergency medical technician.

Embodiments of the invention are possible in which the MP can see what decision the AED logic would have made. In such an embodiment, the AED decision would be a signal which traverses the route 560→558→542A→542B→etc.

FIG. 10 and the associated specification regarding the present example could, besides applying to a modified AED, also apply to a modified manually operated external defibrillator, as discussed in conjunction with FIG. 1, hereinabove. In such a circumstance, element 560 and its connections would be absent, replaced by a) a display device for displaying ECG signals for a local medical professional, and b) local MP control input(s) for inputting defibrillation and/or pacing commands—as shown in FIG. 1. Optionally, the remote MP could, by sending a signal to 554, enable/disable local MP access to defibrillator control.

FIG. 10 and the associated specification regarding the present example could also apply to a modified external defibrillator which has both an AED mode and a local MP controlled (i.e. non-automatic) mode, as discussed in conjunction with FIG. 1, hereinabove. In such a circumstance, AED logic device 560 and its connections would be present. In addition (as shown in FIG. 1 and discussed in the associated specification), there would be a) a display device for displaying ECG signals for a local medical professional coupled to 556, b) local MP control input(s) for inputting defibrillation and/or pacing commands coupled to 554, and c) a means for maintaining a hierarchical control structure, i.e. establishing which control source (among remote MP, local MP and AED logic device) takes priority. Such means could be pre-programmed or pre-wired within 554, or could be supplied to 554 by a remote MP.

Example

System with Unified Adapter and Cardiac Monitoring and Treatment Device

Figure 11:
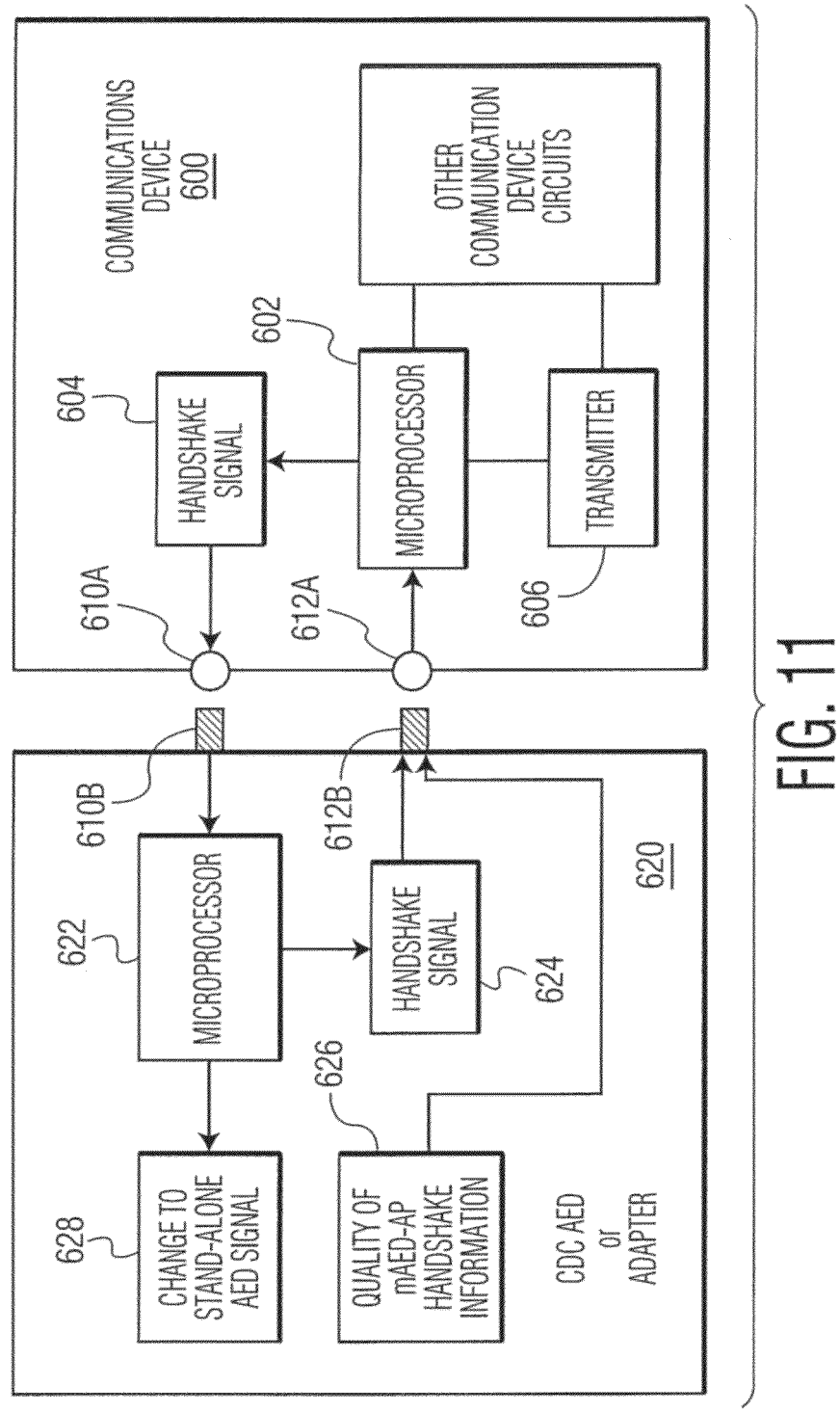
FIG. 11 is a block diagram showing communication confirmation apparatus in a system in which the communications device is a separate entity.

FIG. 11 shows additional units and signals to support a handshaking arrangement which may allow the CD to have information about the adequacy of the hookup of:

a) the AP or the cdcAED to the CD; and/or b) the AP to the mAED.

It may also allow the cdcAED or the AP to have information about the adequacy of the hookup of the mAED.

The purpose of the handshaking is that if the mAED receives a signal indicating inadequate hookup, the signal (arriving at 554 in FIG. 10) would restore conventional (i.e. autonomous) AED function. It might also cause the mAED to attempt to remedy the inadequate connection by electronic means, and/or cause it to notify the enabler of the situation.

If the CD receives a signal indicating inadequate hookup, the signal (arriving at 502 in FIG. 10) would be used to notify the MP of the linkage problem. The MP could a) attempt to remotely repair the problem;

b) notify the enabler of the problem, suggesting a better attempt at linking the units; and/or c) send a signal which attempts to notify the mAED of the failed link, thereby causing a change in mAED function to that of a conventional (autonomous) AED Each of a), b) and c) immediately above may also be performed by the CD itself. To facilitate this, a direct signal connection from the AP to 512 (not shown in the figure) would be beneficial.

Referring again to FIG. 11, the basic handshake loop is from the microprocessor 602 within CD 600, generating handshake signal 604 (corresponding to signal 31A of FIG. 2), transmitted to microprocessor 622 in cdcAED or AP 620 via pins 610A/B (or additional pins, or wireless arrangement), generating handshake signal 624 (corresponding to signal 31B of FIG. 2), transmitted to microprocessor 602 in CD 600 via pins 612A/B (or additional pins, or wireless arrangement). Ser. No. 10/460,458 describes a variety of alternate handshake signals which may be used to signal a non-received handshake and to signal a restored handshake, one or more of which signals may be used in the present invention. The specification hereinabove, in conjunction with FIGS. 2 and 3 gives additional information about approaches to communication confirmation methods and apparatus.

In the case of separate mAED and AP units, the quality of a mAED-AP handshake 626 may be passed along to the CD via 612A/B. The transmission of a signal indicating a failed AP-mAED handshake would have a similar effect as the transmission of a failed AP-CD handshake (or a failed cdcAED-CD handshake): 602 would send a signal via transmitter 606 to the MP; This would be acted on as discussed above. 602 would also cause 606 to send a failed handshake signal (which, in a preferred embodiment of the invention would indicated the point of failure insofar as it may be known), in the event that it did not receive a handshake signal within a preset time after sending one.

In the case of 622 not receiving a handshake signal in a preset time after sending one, it would issue signal 628 indicating a handshake failure, to the mAED. This would initiate, as indicated above, a variety of possible mAED actions. Furthermore, 628 could be issued if 622 receives a signal indicating that 602 failed to receive a handshake signal.

The cdcAED may be manufactured as such at the time of its original build. Alternatively, an AED may be modified, post initial production, to have the functionality and components of a cdcAED. In either of the two aforementioned cases, it would be possible to further configure the cdcAED such that the remote control feature could be an option which must be turned on by either a key, another means of identification, a signal, combinations of the aforementioned, or other means as is obvious to those skilled in the art.

In the case of a 3-unit device, although FIGS. 1, 5C and 10 shows a geometry in which the adapter lies physically between the mAED and the CD, it would be possible, in another embodiment of the invention, to have:

a) the adapter connect to the mAED but not directly to the CD; and b) the CD connect directly to the mAED but not to the adapter.

In yet another embodiment of the invention, it would be possible to have:

a) the adapter connect to the CD but not directly to the mAED; and b) the CD connect directly to the mAED but not to the adapter.

Figure 12A:
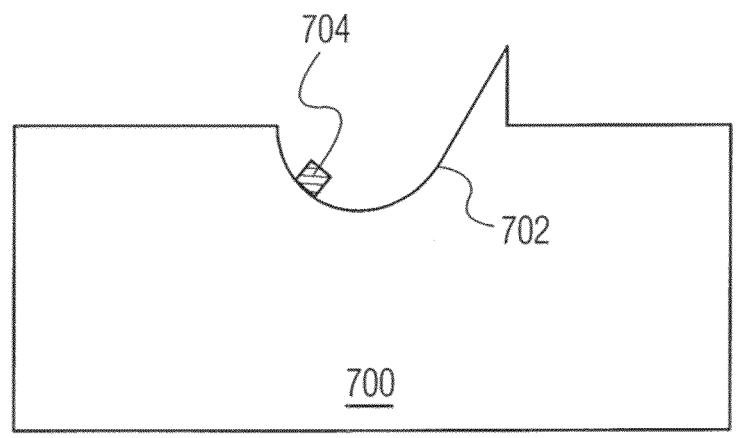
FIG. 12A is a front view of a cardiac monitoring and treatment device which is suitable for coupling to and accommodating a cellular telephone apparatus.
Figure 12B:
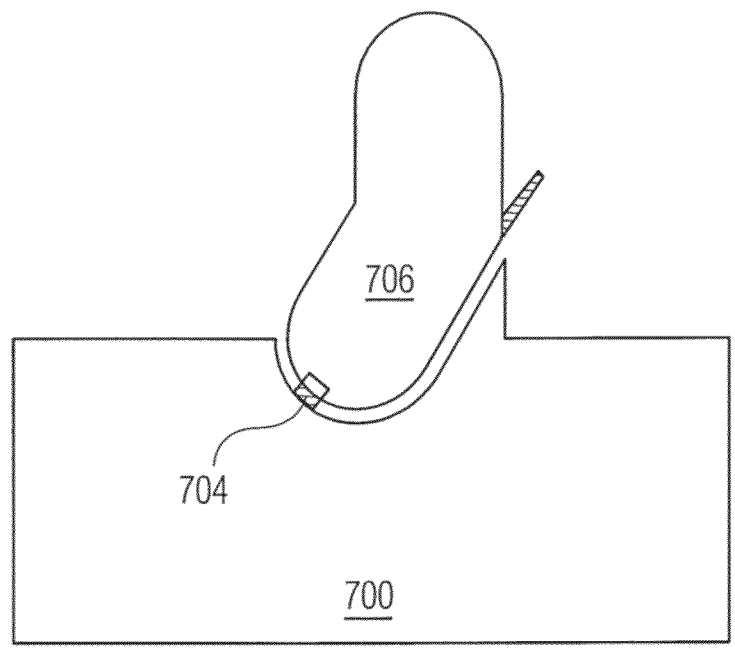
FIG. 12B is a front view of a cardiac monitoring and treatment device which is coupled to a cellular telephone apparatus.

FIG. 12A shows one possible embodiment of the apparatus which may connect a CD to a cdcAED: cdcAED 700 can accommodates a CD (e.g. a cellular telephone) within appropriate shaped cellular telephone receptacle section 702. Within 702 is a multi-pin connector 704 which will functionally perform as 522B and 522D of FIG. 10. FIG. 12B shows the cell phone 706 in place: 704 has been inserted into a slot within 706 which contains components analogous to 522A and 522C of FIG. 10. Additional apparatus to secure the cellular telephone in place may be present.

Figure 13:
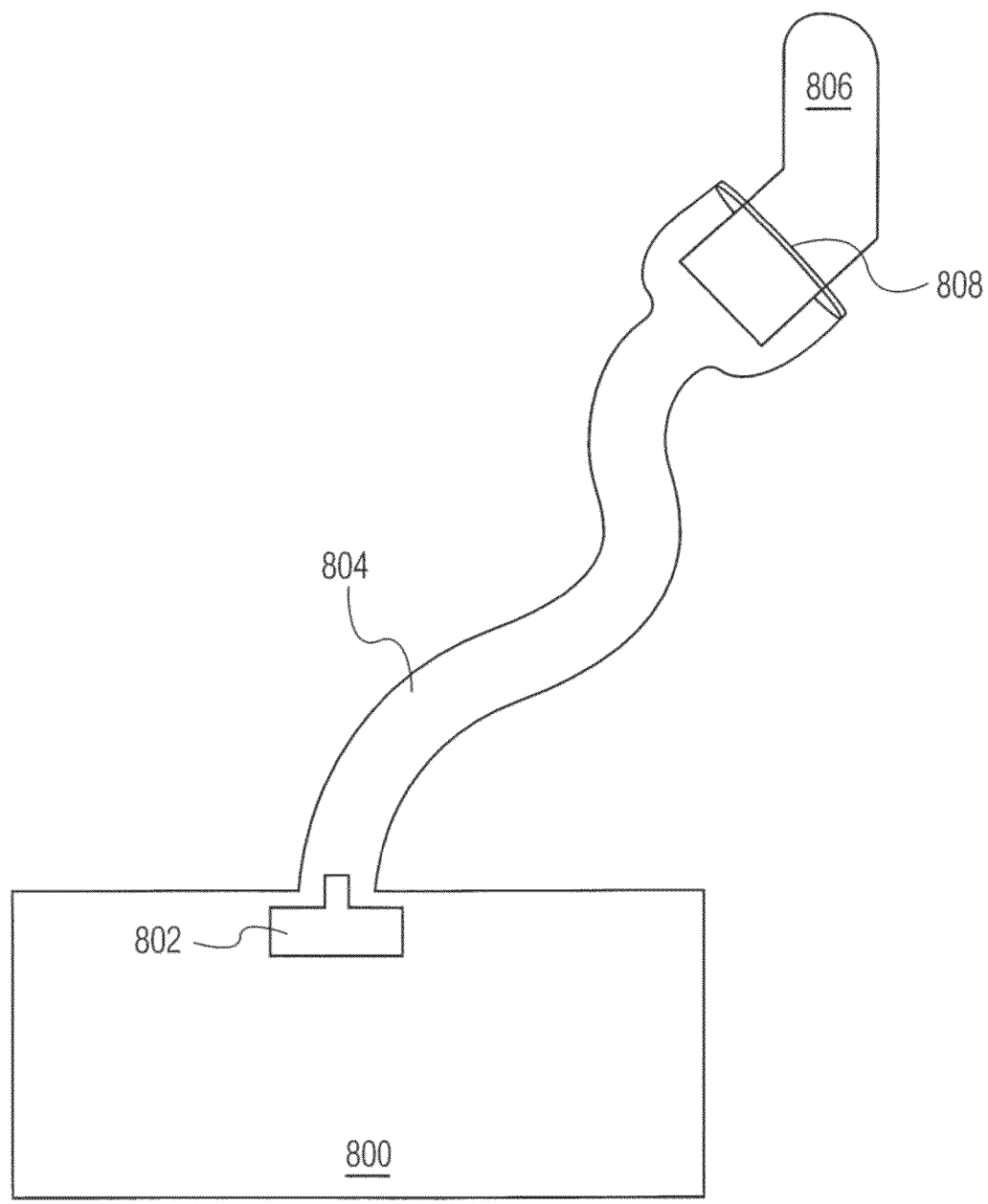
FIG. 13 is a front view of a cardiac monitoring and treatment device which is coupled to a cellular telephone apparatus which may be angulated by a remote operator in order to optimize audio and video communications.
Figure 14A:
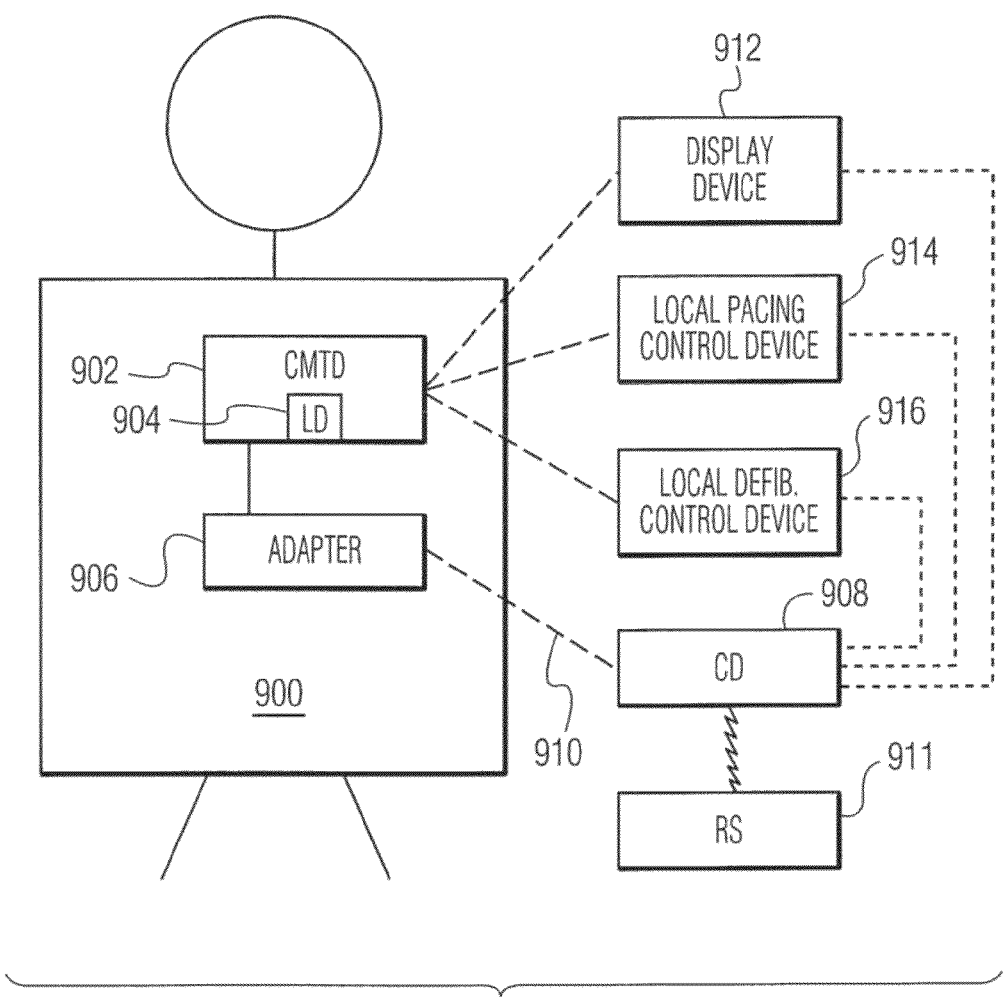
FIG. 14A shows a block diagram of the invention in which both the adaptor and the cardiac monitoring and treatment device is inside a body of a person.
Figure 14B:
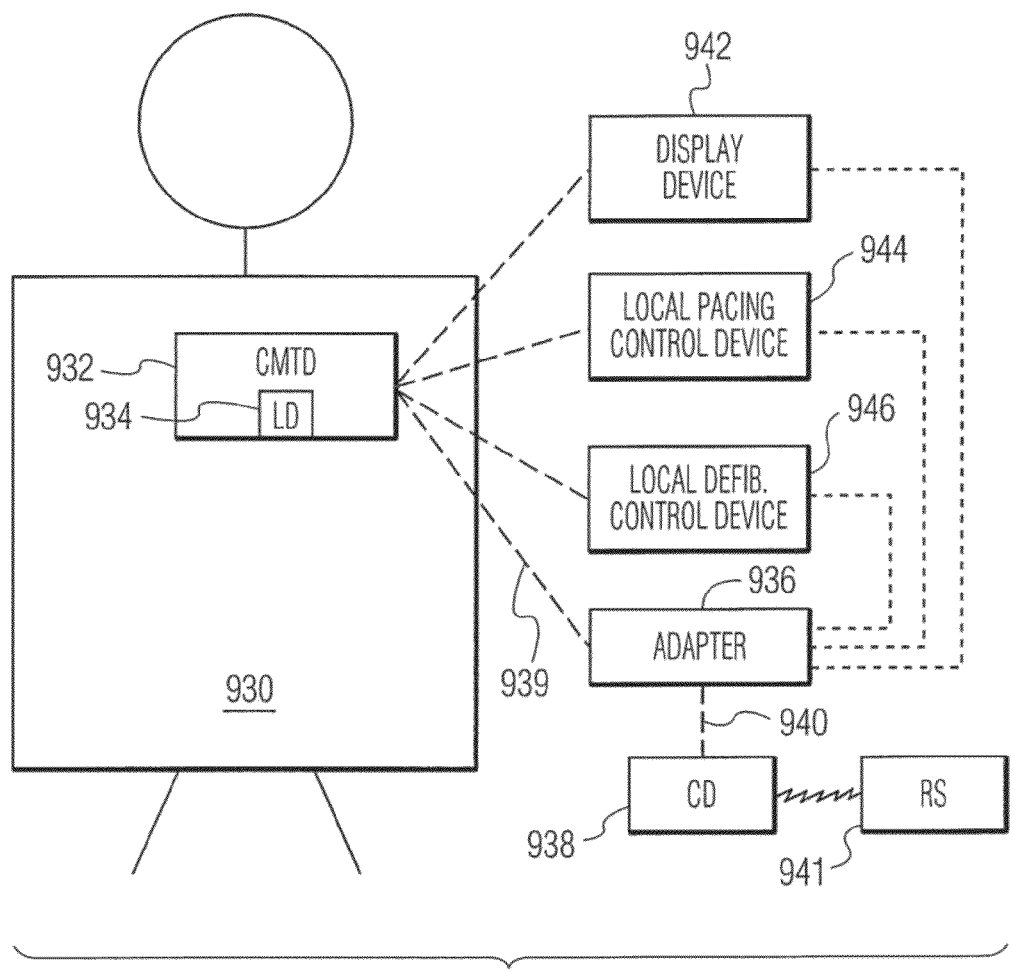
FIG. 14B shows a block diagram of the invention in which the cardiac monitoring and treatment device is inside a body of a person.
Figure 14C:
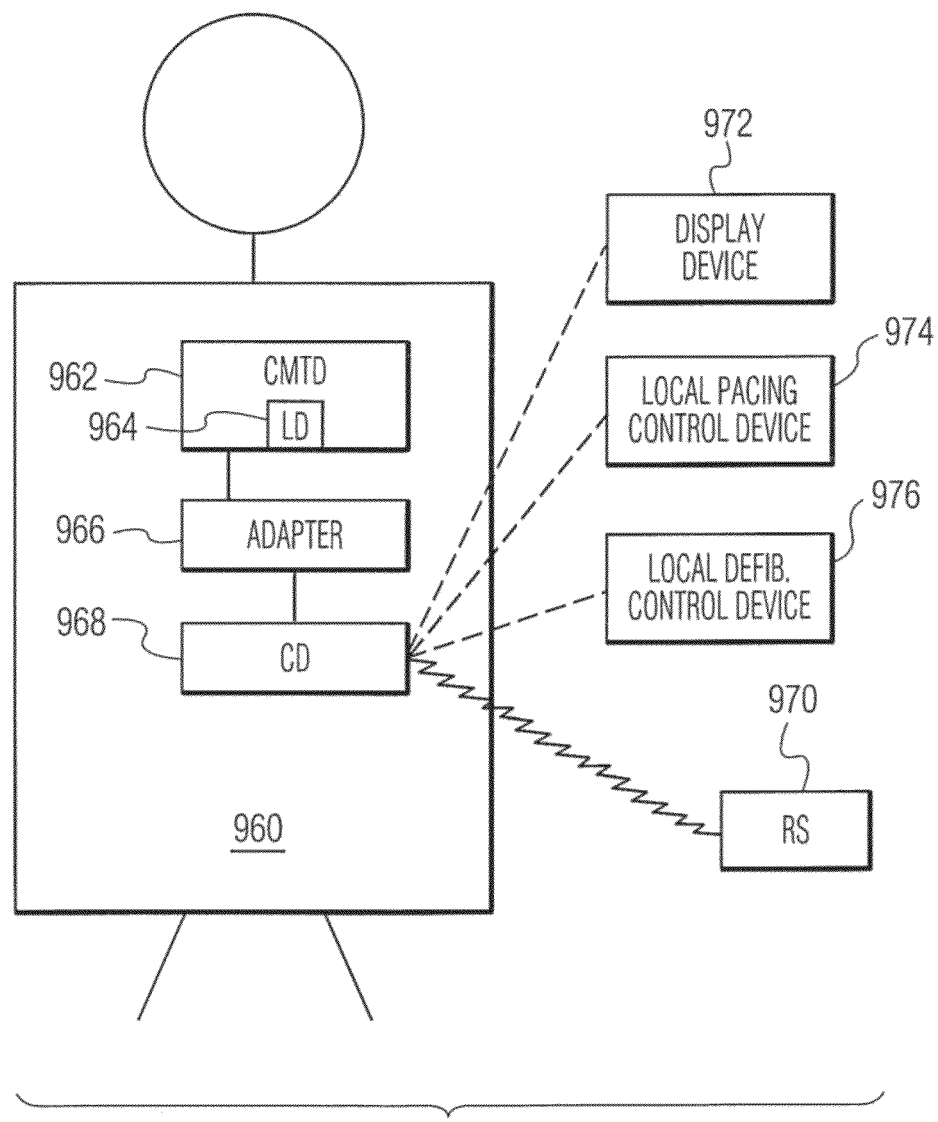
FIG. 14C shows a block diagram of the invention in which each of the communication device, the adapter, and the cardiac monitoring and treatment device are inside a body of a person.

FIG. 13 shows one embodiment of the invention containing apparatus for securing a CD 806 at the end of a maneuverable boom 804. The boom is part of either the mAED or the cdcAED 800. The purpose of the arrangement would be to let the MP maneuver the CD so that audio and, if present, video communication is optimized. The angular relationships between the CD and the enabler, or between the CD and the victim, may change as the management of the emergency situation progresses, and this feature would be useful in such a circumstance.

In the figure, holding apparatus 808 may be an elastic strap which helps fix 806 to a receptacle within 804. Many other arrangements for securing 806 to 804 will be obvious to those skilled in the art.

The apparatus shown in FIG. 13 would also be useful in cases where the relationship geometric relationship among CD, enabler and victim does not change; Allowing the MP to do the optimizing of CD position and angulation saves valuable time, i.e. by taking the task away from the enabler.

Embodiments of the invention in which the boom is either extensible or not extensible are possible.

Embodiments of the invention are possible in which:

a) only the enabler orients and/or extends the boom;

b) only the MP orients and/or extends the boom; and c) either the MP or the enabler can orient and/or extend the boom, are possible.

In embodiments of the invention in which the MP may orient and/or extend the boom, apparatus 802 allows the MP to do so. Such apparatus may allow the MP to control the angulation and/or rotation of the boom at one or more points along the shaft, to rotate or tilt the CD at the end of the shaft, to extend or retract the shaft, or combinations of these motions.

Embodiments of the invention in which one or more of the audio or video interfaces is part of the mAED rather than part of the CD are possible. An obvious example would be to use a larger video display screen or louder audio apparatus that may be part of the mAED. However, examples in which the microphone and/or the video camera are part of the mAED are also possible. Embodiments in which one or more of these components is part of the AP are also possible.

Example

Versions of the System with at Least One Implantable Component

FIGS. 14A, 14B and 14C show embodiments of the invention in which the CMTD is implanted inside the body. Since the CMTDs in each of these three figures could be pacemakers or defibrillator-pacemakers, a logic device—which controls the automatic pacing and sensing function of each respective device—is shown within each.

Referring to FIG. 14A, CMTD 902 containing logic device 904 is implanted inside of person 900. In the embodiment shown by FIG. 14A, the AP 906 is inside the body, and is linked to 902 by a hard-wired connection. Signals 910 link AP 906 and CD 908. The signals may be any short range wireless signal, e.g. radiofrequency, as is known in the art. The CD communicates with a remote station 911, using any of the means described hereinabove. Thus a remotely located medical professional can control the implanted device, i.e. by a) receiving signals from intracardiac and/or intrathoracic electrodes (not shown) sent from 902 to 906 to 908 to the RS 911; and b) sending control signals from the RS 911 to 908 to 906 to 902.

In one embodiment of the invention, the CD is a cellular telephone in the pocket of person 900, or elsewhere in the vicinity of 900. Other communication devices are possible for the CD.

The CD may also be part of a pacemaker/defibrillator programmer. In such a circumstance, the programmer would also contain:

a) display device 912 for displaying intracardiac and/or intrathoracic electrical activity to a local MP; and b) at least one of (i) local pacing control device(s) 914 and (ii) local defibrillator control device(s) 916, each of which lets a local MP assess the current and prior heart rhythm, assess the functioning of CMTD, and change its operating parameters. These local control devices would allow the MP to change the operating parameters:

for long term use (e.g. programming an ICD's parameters for VT detection), and/or for current use (e.g. dealing with an episode of VT in progress at the time of local MP use).

The display device may also be part of a touch sensitive screen, which would allow a local MP to input commands, in a manner known in the art.

Embodiments of the invention are possible in which one, two or three of 912, 914 and 916:

a) communicate directly with the CMTD (shown in the figure by long dashed lines);

b) communicate with the CMTD via the AP (not shown in the figure) by exchanging signals directly with the AP;

c) communicate with the CMTD via the CD (shown in the figure by short dashed lines), along the routes 908 to 906 to 904, and 904 to 906 to 908.

Referring to FIG. 14B, CMTD 932 containing logic device 934 is implanted inside of person 930. In this embodiment, the AP 936 which is outside the body, exchanges signals 939 with CMTD 932 by a wireless connection. Signals 940 link AP 936 and CD 938. Each of signals 939 and 940 may be any short range wireless signal, e.g. radiofrequency, as is known in the art; The 936-938 connection may also be a hard-wired one. The CD communicates with a remote station 941, using any of the means described hereinabove. Thus a remotely located medical professional can control the implanted device, i.e. by a) receiving signals from intracardiac and/or intrathoracic electrodes (not shown) sent from 932 to 936 to 938 to the RS 941; and b) sending control signals from RS 941 to 938 to 936 to 932.

In one embodiment of the invention, the CD and the adapter are physically linked—as shown for the cRCD of FIG. 5A, and may constitute a communication device carried by person 930, or be in the vicinity of 930.

The adapter may also be part of a pacemaker/defibrillator programmer. In such a circumstance, the programmer would also contain a) display device 942 for displaying intracardiac and/or intrathoracic electrical activity to a local MP; and b) at least one of (i) local pacing control device(s) 944 and (ii) local defibrillator control device(s) 946, each of which lets a local MP assess the current and prior heart rhythm, assess the functioning of CMTD, and change its operating parameters. These local control devices would allow the MP to change the operating parameters:

for long term use (e.g. programming an ICD's parameters for VT detection), and/or for current use (e.g. dealing with an episode of VT in progress at the time of local MP use).

The display device may also be part of a touch sensitive screen, which would allow a local MP to input commands, in a manner known in the art.

Embodiments of the invention are possible in which one, two or three of 942, 944 and 946:

a) communicate directly with the CMTD (shown in the figure by long dashed lines);

b) communicate with the CMTD via the AP by directly exchanging signals with the AP (shown in the figure by short dashed lines).

Referring to FIG. 14C, CMTD 962 containing logic device 964 is implanted inside of person 960. In the embodiment shown by FIG. 14C, the AP 966 is inside the body, and is linked to 962 by a hard-wired connection; CD 968 is also inside the body, and is linked to AP 966 by a hardwired connection. The CD communicates with remote station 970, using any of the wireless means described hereinabove. Thus a remotely located medical professional can control the implanted device, i.e. by a) receiving signals from intracardiac and/or intrathoracic electrodes (not shown) sent from 962 to 966 to 968 to 970; and b) sending control signals from the 970 to 968 to 966 to 962.

In one embodiment of the invention, one or more of the adapter connections (to 962 and/or 968) may be wireless.

A pacemaker/defibrillator programmer may be used in conjunction with the implanted hardware. In such a circumstance, the programmer would also contain:

a) display device 972 for displaying intracardiac and/or intrathoracic electrical activity to a local MP; and b) at least one of (i) local pacing control device(s) 974 and (ii) local defibrillator control device(s) 976, each of which lets a local MP assess the current and prior heart rhythm, assess the functioning of CMTD, and change its operating parameters. These local control devices would allow the MP to change the operating parameters:

for long term use (e.g. programming an ICDs parameters for VT detection), and/or for current use (e.g. dealing with an episode of VT in progress at the time of local MP use).

The display device may also be part of a touch sensitive screen, which would allow a local MP to input commands, in a manner known in the art.

Embodiments of the invention are possible in which one, two or three of 972, 974 and 976:

a) communicate directly with the CMTD (not shown in the figure);

b) communicate with the CMTD via the AP (not shown in the figure) by exchanging signals directly with the AP;

c) communicate with the CMTD via the CD (shown in the figure by short dashed lines).

The adapter apparatus described hereinabove concerns communication between a single medical device and a communications device. The apparatus described hereinbelow concerns the communication among a plurality of medical devices and at least one adapter. Each adapter function described hereinabove is may be a feature of an adapter which communicates with a plurality of medical devices.

In the following, a single medical device is referred to as "MDEV", and a particular one as, for example MDEV-1, MDEV-2, and an nth device as MDEV-N. Letter subscripts for the medical devices in the figure at times utilize other letters to distinguish among different pluralities of MDEVs in different figures.

A treatment device is intended to indicate (i) a device which provides medical therapy, (ii) a device which provides signals representing a physiologic state of a person, or (iii) both (i) and (ii).

Figure 15A:
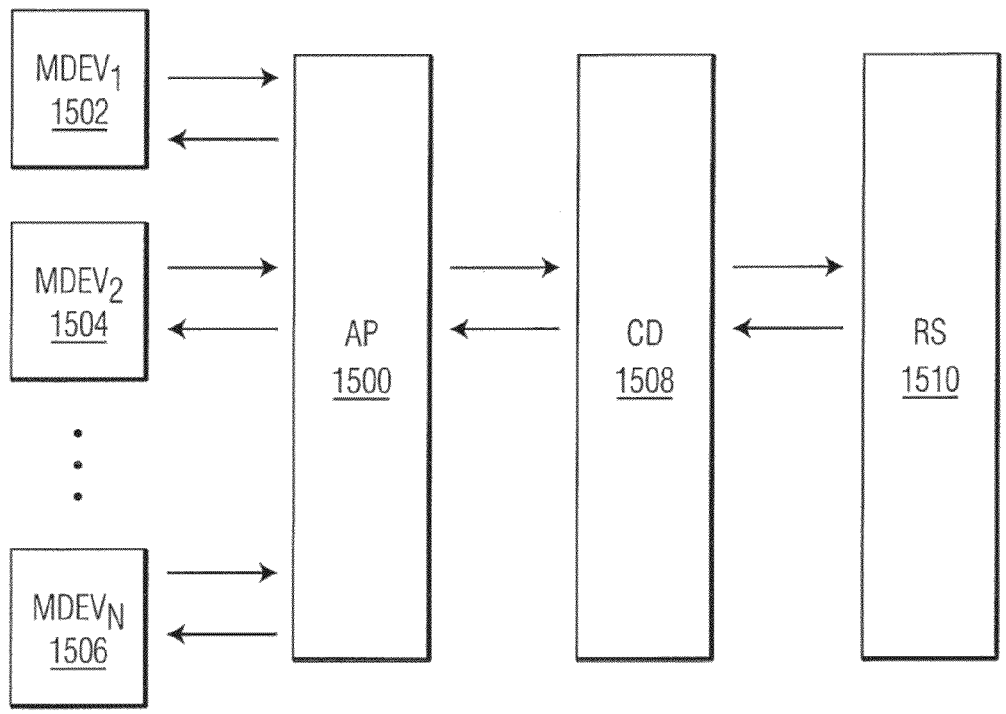
FIG. 15A shows a block diagram of an adapter which communicates with a plurality of medical devices and with one communications device.

FIG. 15A shows a block diagram of an adapter 1500 which communicates with a plurality of medical devices 1502, 1504 and 1506 and with one communications device ("CD") 1508. The CD communicates with a remote station 1510. The notation in the figure in which three dots extend from MDEV-2 to MDEV-N is intended to indicate a plurality of such medical device. Each of the entities in FIG. 15A is capable of two way communication. Embodiments in which one or more medical devices communicates in one way (either to or from the adapter) are possible. Embodiments of the adapter in which one way communication with another entity occurs are possible. Either the CD or the RS may be a source of control of one or more of the medical devices, or may obtain information for such control from one or more of the medical devices. The treatment agent ("TA") which exerts such control may be a human, a microprocessor, a computational device or a combination of these.

Figure 15B:
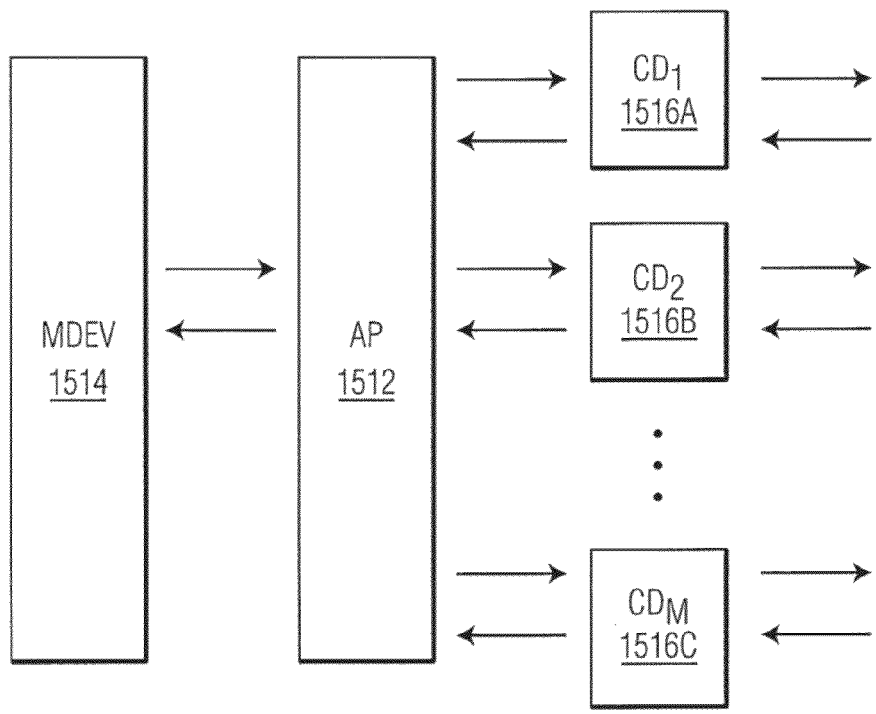
FIG. 15B shows a block diagram of an adapter which communicates with a plurality of communications devices and with one medical device.

FIG. 15B shows a block diagram of an adapter 1512 which communicates with a plurality of communications devices 1516A-C and with one medical device 1514.

Figure 15C:
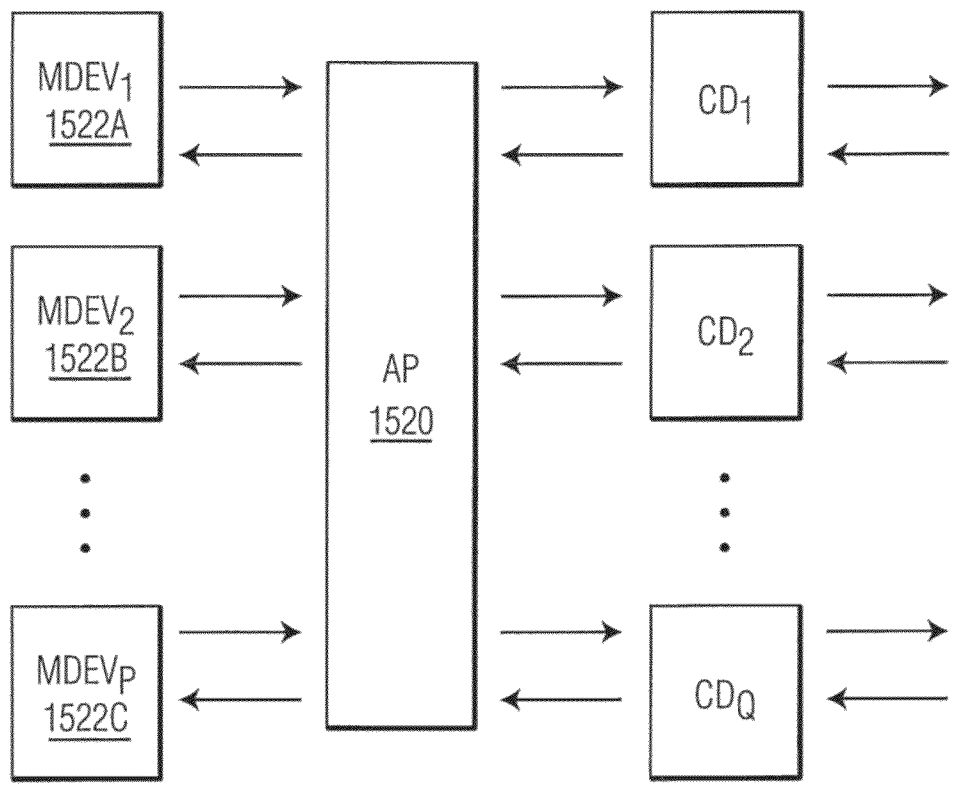
FIG. 15C shows a block diagram of an adapter which communicates with a plurality of medical devices and with a plurality of communications devices.

FIG. 15C shows a block diagram of an adapter 1520 which communicates with a plurality of medical devices 1522A-C and with a plurality of communications devices CD-1 to CD-Q.

Figure 16A:
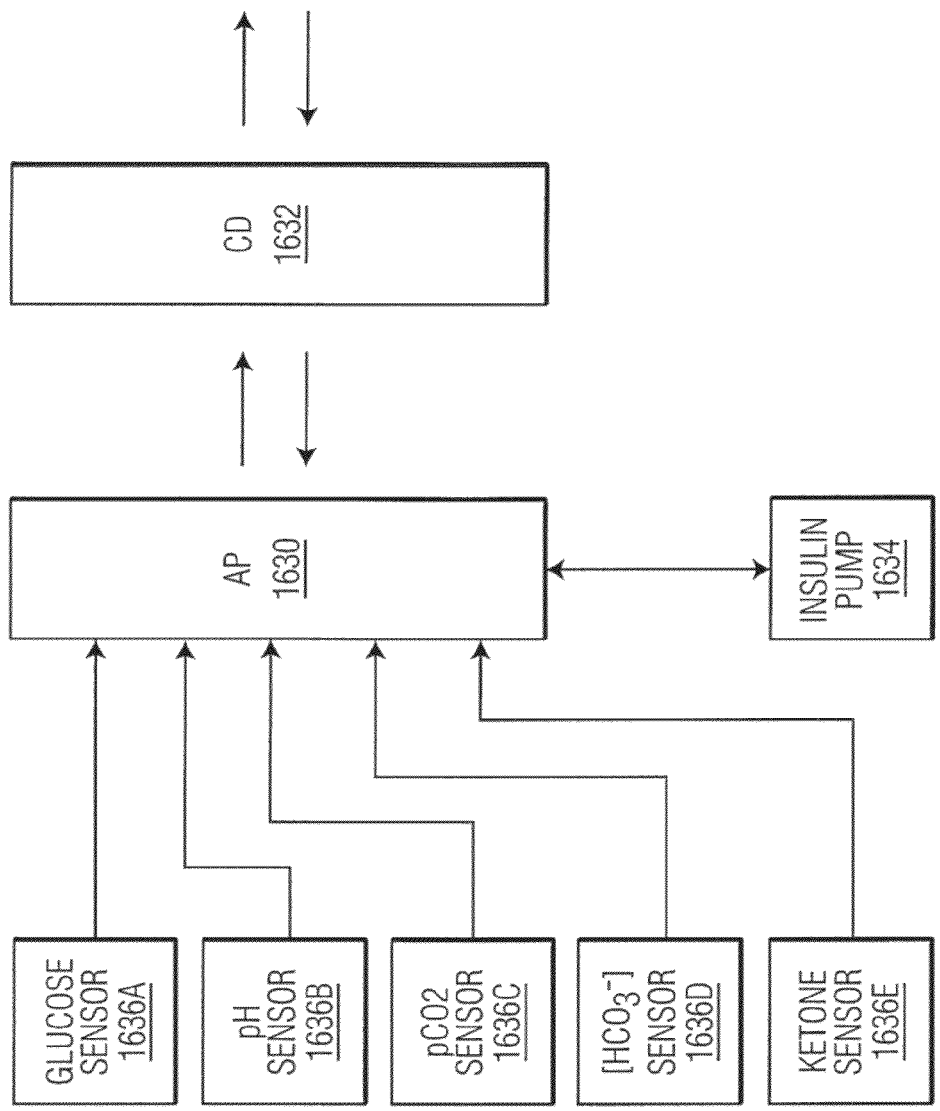
FIG. 16A shows a block diagram of an adapter which communicates with diabetes management devices and a communications device.

FIG. 16A shows a block diagram of an adapter 1630 which communicates with diabetes management devices and a communications device 1632. The diabetes management devices include an insulin pump 1634 and a variety of sensors 1636A-E. Systems with a smaller or larger number of sensors are possible. In a preferred embodiment, the insulin pump receives physiologic information from the sensors and a microprocessor, microcontroller or other computational device within the pump apparatus 1634 uses this information for decision making. Furthermore, an outside agent—either the patient, a computational device, or another medical professional may access, via the adapter and the CD, either (a) the sensor information, (b) the insulin pump, or (c) both.

Pump access is two way, allowing outside control and allowing the pump to communicate status information and confirmation signals. Embodiments of the system include those in which (a) 1634 is controlled entirely by an outside TA, (b) 1634 control is autonomous, relying only on sensor information from 1636A-E, and (c) control may be shared by each of the TA and the computational apparatus within 1634.

Figure 16B:
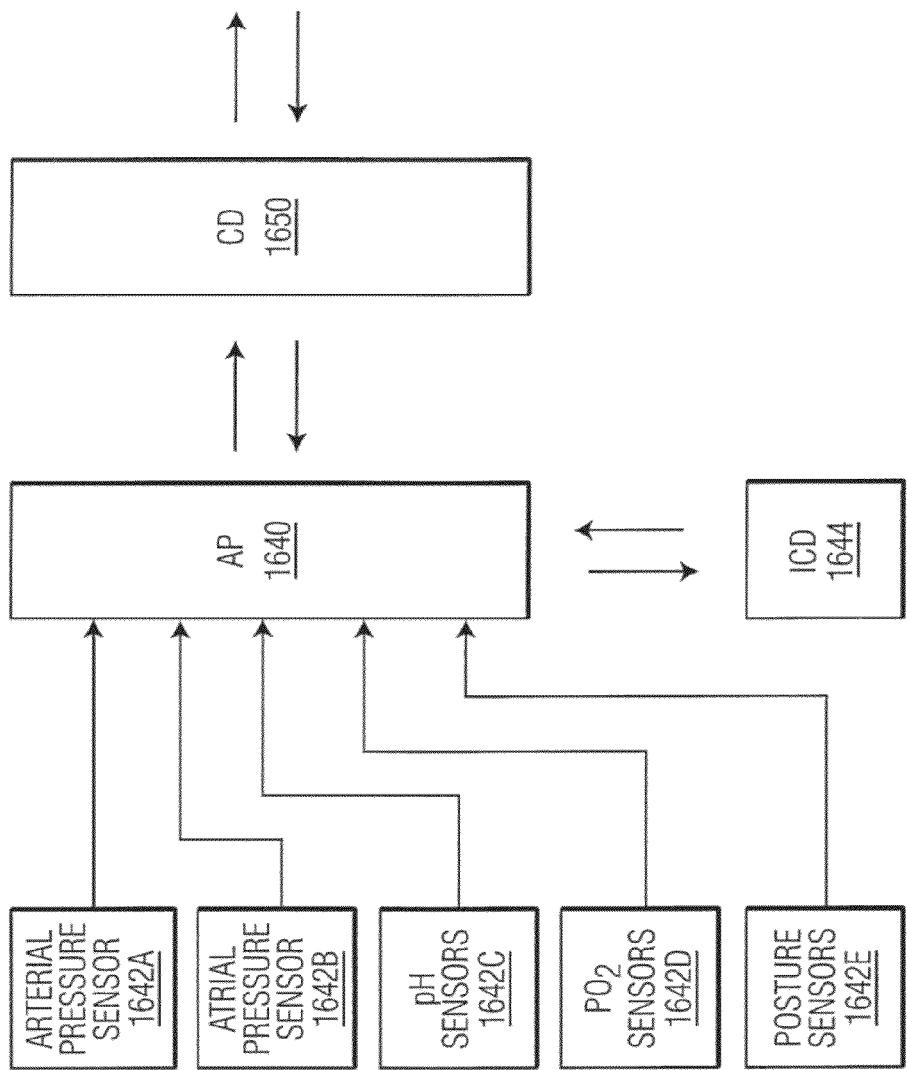
FIG. 16B shows a block diagram of an adapter which communicates with an implantable defibrillator ("ICD"), a plurality of sensor devices for providing cardiac information and a communications device.

FIG. 16B shows a block diagram of an adapter 1640 which communicates with an implantable defibrillator ("ICD") 1644, a plurality of sensor devices 1642A-E for providing cardiac information and a communications device 1650.

Systems with a smaller or larger number of sensors are possible. In a preferred embodiment, the ICD receives physiologic information from the sensors and a microprocessor, microcontroller or other computational device within the ICD apparatus 1644 uses this information for decision making. Furthermore, an outside agent—either the patient, a computational device, or another medical professional may access, via the adapter and the CD, either (a) the sensor information, (b) the ICD, or (c) both. ICD access is two way, allowing outside control and allowing the ICD to communicate status information, information from ICD leads and confirmation signals. Embodiments of the system include those in which (a) 1644 is controlled entirely by an outside TA, (b) 1644 control is autonomous, relying only on sensor information from 1642A-E, and (c) control may be shared by each of the TA and the computational apparatus within 1644.

Figure 17A:
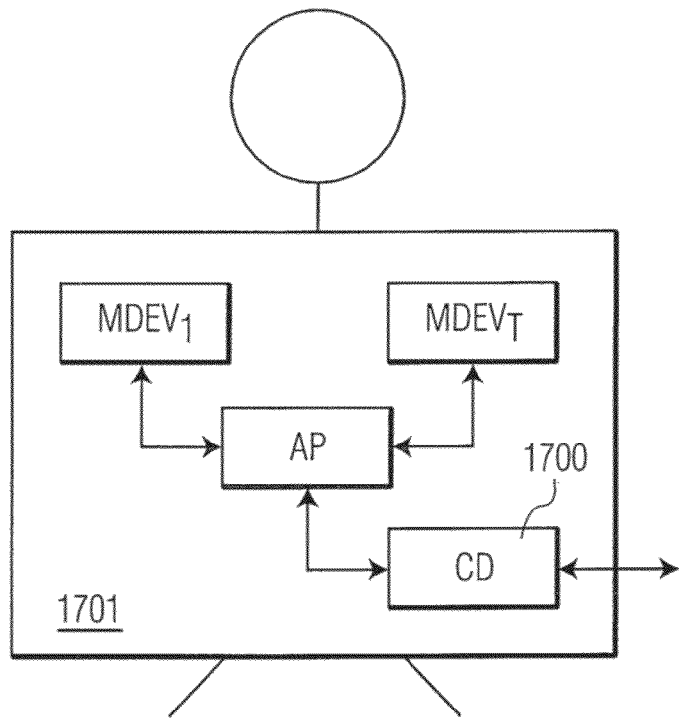
FIG. 17A shows a block diagram in which all of the components of a system comprising a plurality of medical devices, an adapter and a communications devices are implanted in a person.

FIG. 17A shows a block diagram in which all of the components of a system comprising a plurality of medical devices, an adapter and a communications devices are implanted in a person 1701. The two way arrows indicate bidirectional communication. The CD 1700 communicates with an outside TA. The two devices shown, MDEV-1 and MDEV-T are intended to indicate two or more implanted medical devices. This notational convention is utilized in conjunction with the figures hereinabove and hereinbelow, as indicated hereinabove.

Figure 17B:
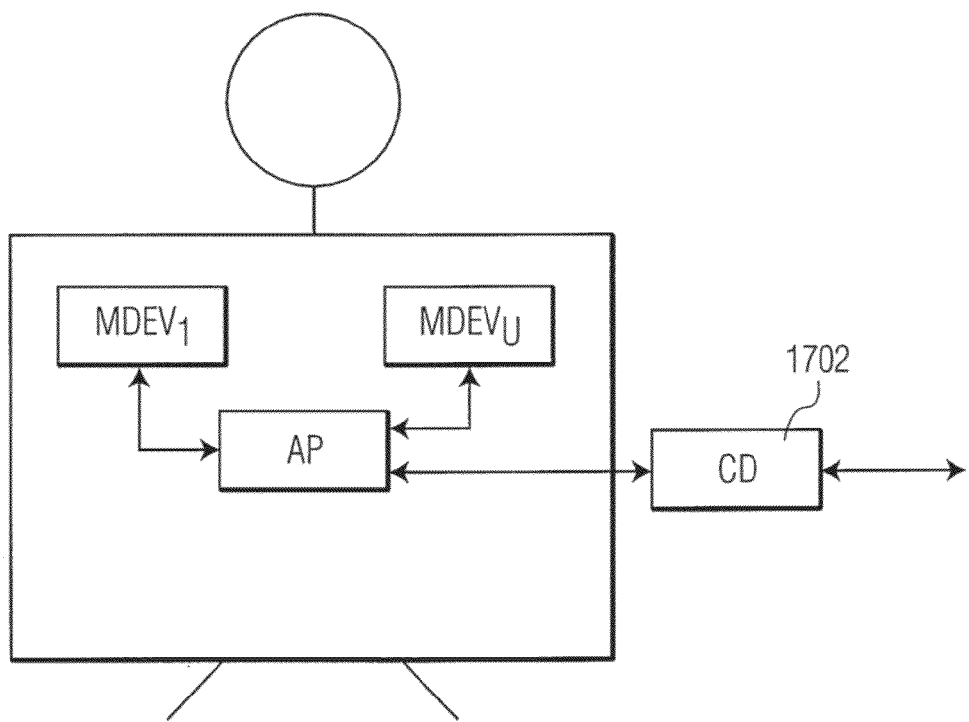
FIG. 17B shows a block diagram in which a plurality of medical devices and an adapter are implanted in a person, and in which the adapter communicates with an external communications device.

FIG. 17B shows a block diagram in which a plurality of medical devices and an adapter are implanted in a person, and in which the adapter communicates with an external communications device. The CD 1702 communicates with an outside TA.

Figure 17C:
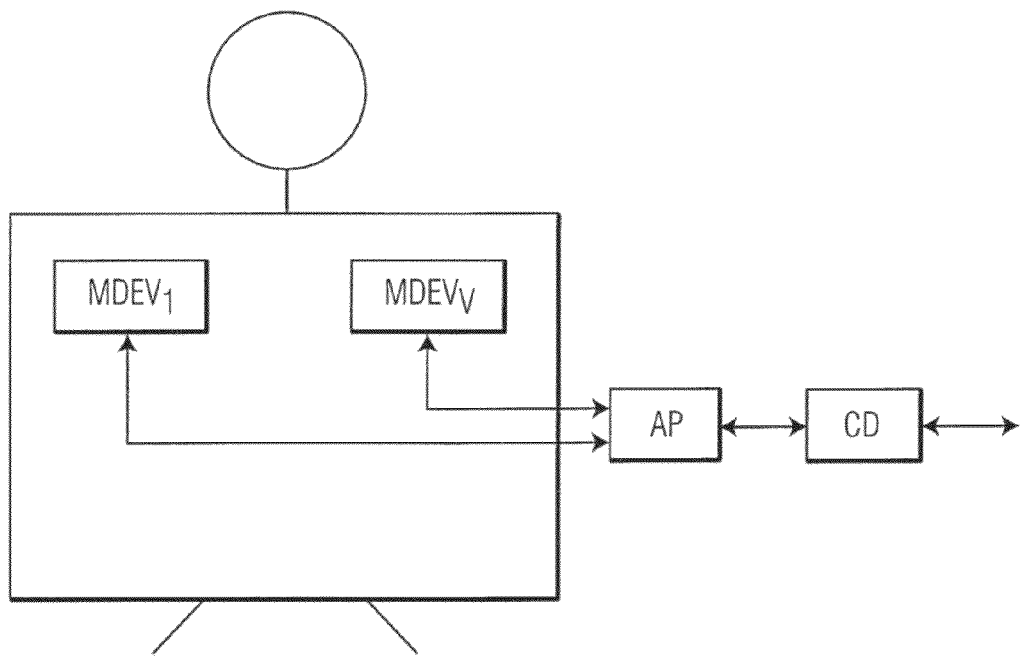
FIG. 17C shows a block diagram in which a plurality of medical devices are implanted in a person, which communicate with an adapter, external to the person, which communicates with an external communications device.

FIG. 17C shows a block diagram in which a plurality of medical devices are implanted in a person, which communicate with an adapter, external to the person, which communicates with an external communications device.

Figure 17D:
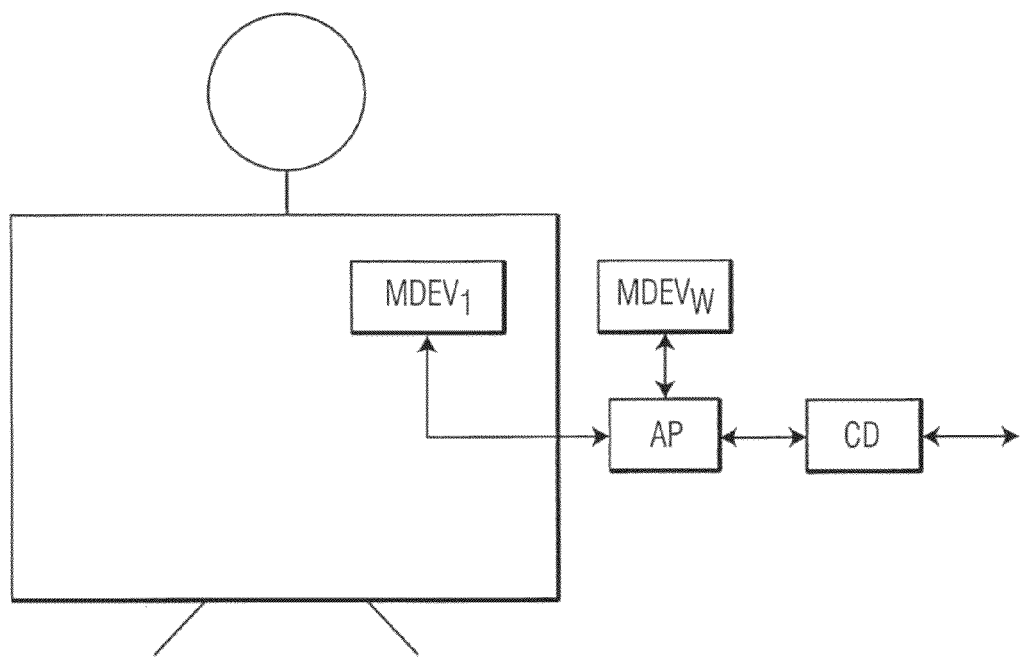
FIG. 17D shows a block diagram in which some of a plurality of medical devices are implanted in a person, and some of which are external to the person, all of which communicate with an adapter external to the person, which communicates with an external communications device.

FIG. 17D shows a block diagram in which some of a plurality of medical devices are implanted in a person (indicated by MDEV-1), and some are external to the person (indicated by MDEV-W), all of which communicate with an adapter external to the person, which communicates with an external communications device.

Figure 17E:
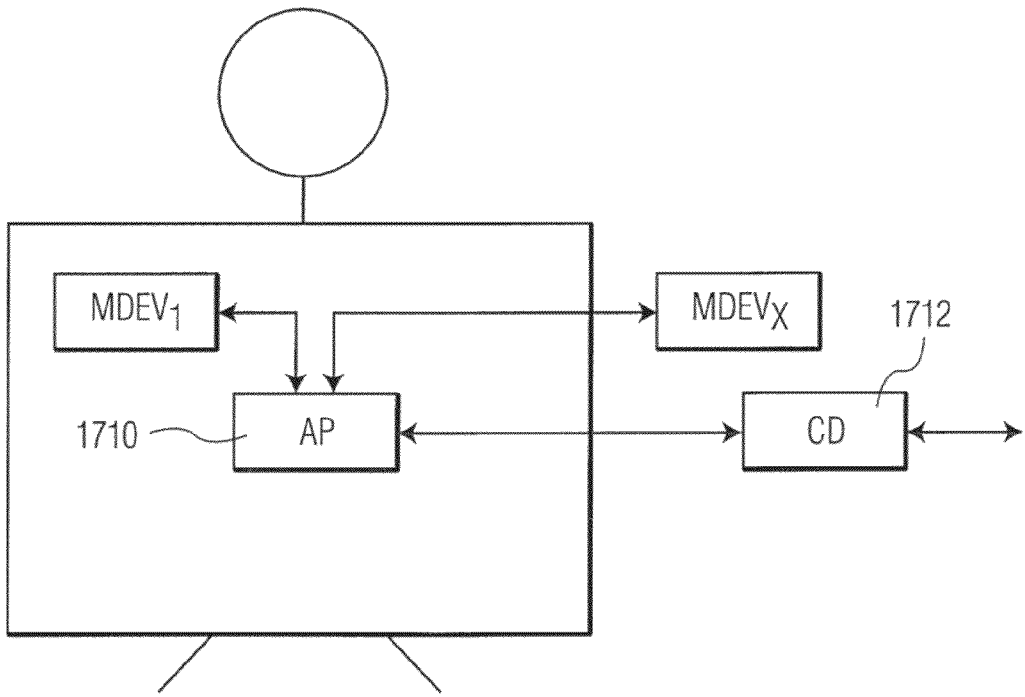
FIG. 17E shows a block diagram in which some of a plurality of medical devices are implanted in a person, and some of which are external to the person, all of which communicate with an internally situated adapter, which communicates with an external communications device.

FIG. 17E shows a block diagram in which some of a plurality of medical devices are implanted in a person (MDEV-1), and some of which are external to the person (MDEV-X), all of which communicate with an internally situated adapter 1710, which communicates with an external communications device 1712.

Figure 17F:
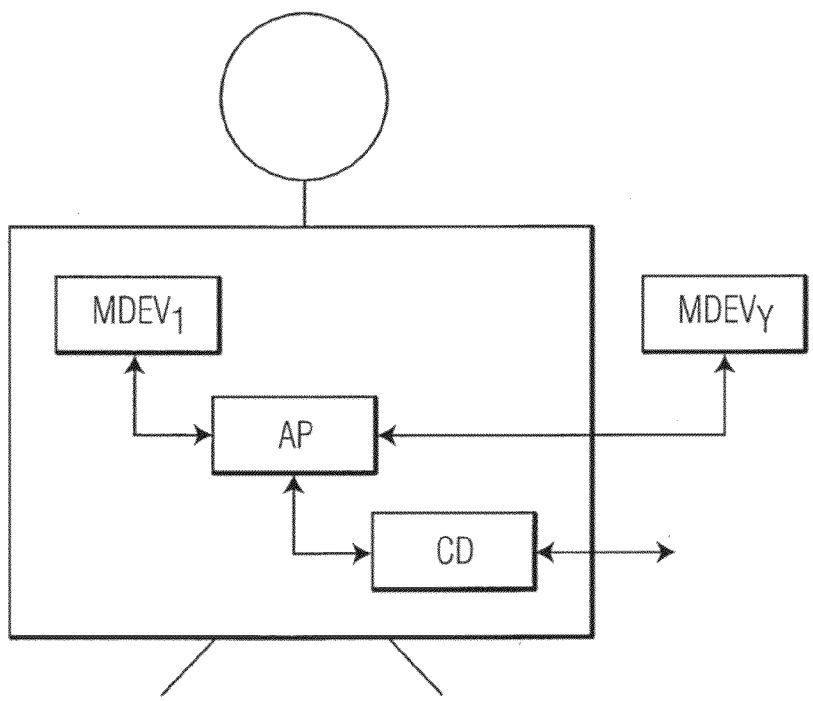
FIG. 17F shows a block diagram in which some of a plurality of medical devices are implanted in a person, and some of which are external to the person, all of which communicate with an internally situated adapter, which communicates with an internal communications device.

FIG. 17F shows a block diagram in which some of a plurality of medical devices are implanted in a person, and some of which are external to the person, all of which communicate with an internally situated adapter, which communicates with an internal communications device.

Figure 17G:
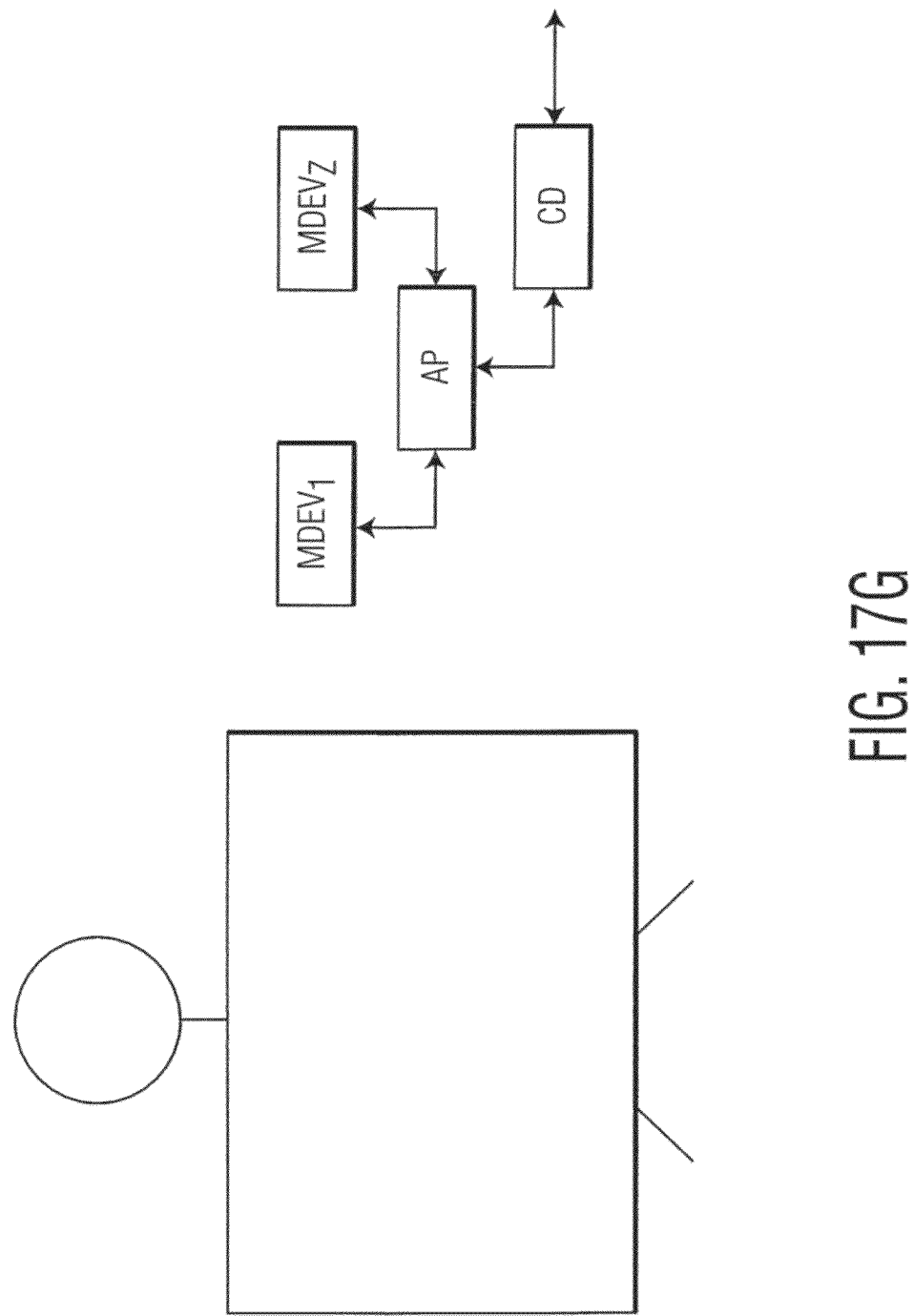
FIG. 17G shows a block diagram in which all of the components of a system comprising a plurality of medical devices, an adapter and a communications devices are all external to the body of a person.

FIG. 17G shows a block diagram in which all of the components of a system comprising a plurality of medical devices, an adapter and a communications devices are all external to the body of a person.

Figure 18A:
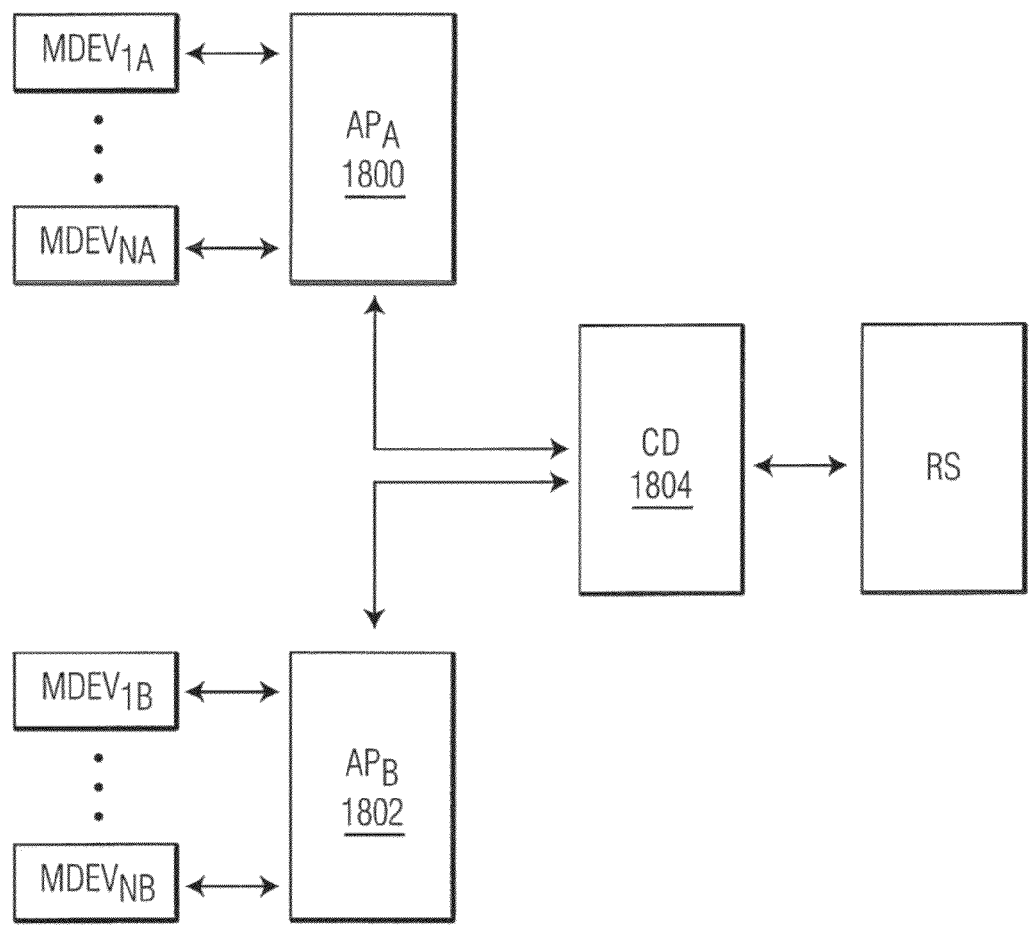
FIG. 18A shows a block diagram of a system which includes two adapters.

FIG. 18A shows a block diagram of a system which includes two adapters. One adapter 1800 communicates with a first plurality of medical devices MDEV-1A to MDEV-NA. The second adapter communicates with a second plurality of medical devices MDEV-1B to MDEV-NB. Each adapter communicates with CD 1804. Such a configuration may obtain when the first plurality of devices are implanted in a body, and the second plurality are external to the body. Another situation in which such a configuration may occur would be when a first plurality are made by one manufacturer and the second plurality is made by another manufacturer.

Figure 18B:
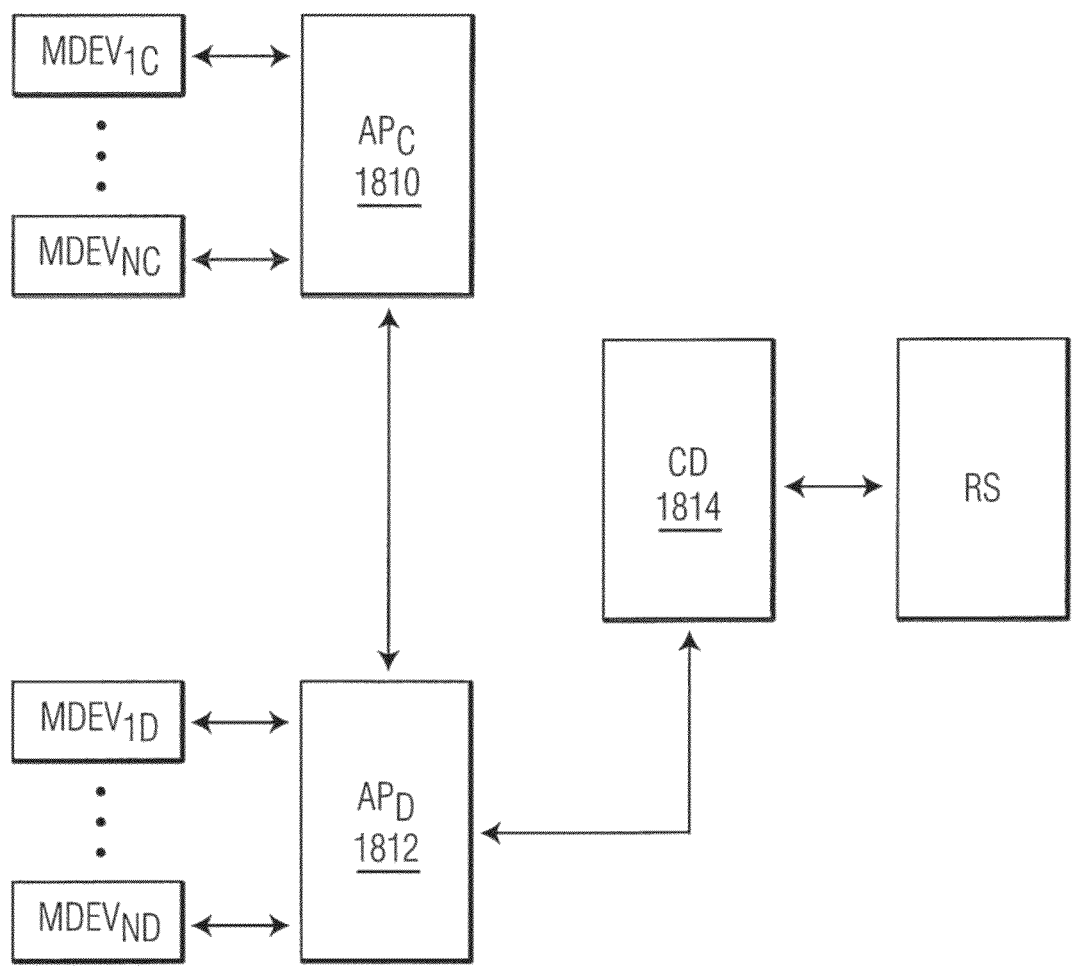
FIG. 18B shows a block diagram of another system which includes two adapters.

FIG. 18B shows a block diagram of another system which includes two adapters. The configuration shown (and considerations) related to this figure are similar to those of FIG. 18A, except that in the case of FIG. 18B, on 1812 communicates directly with the CD 1814. 1810 communicates with 1814 through adapter 1812.

Figure 18C:
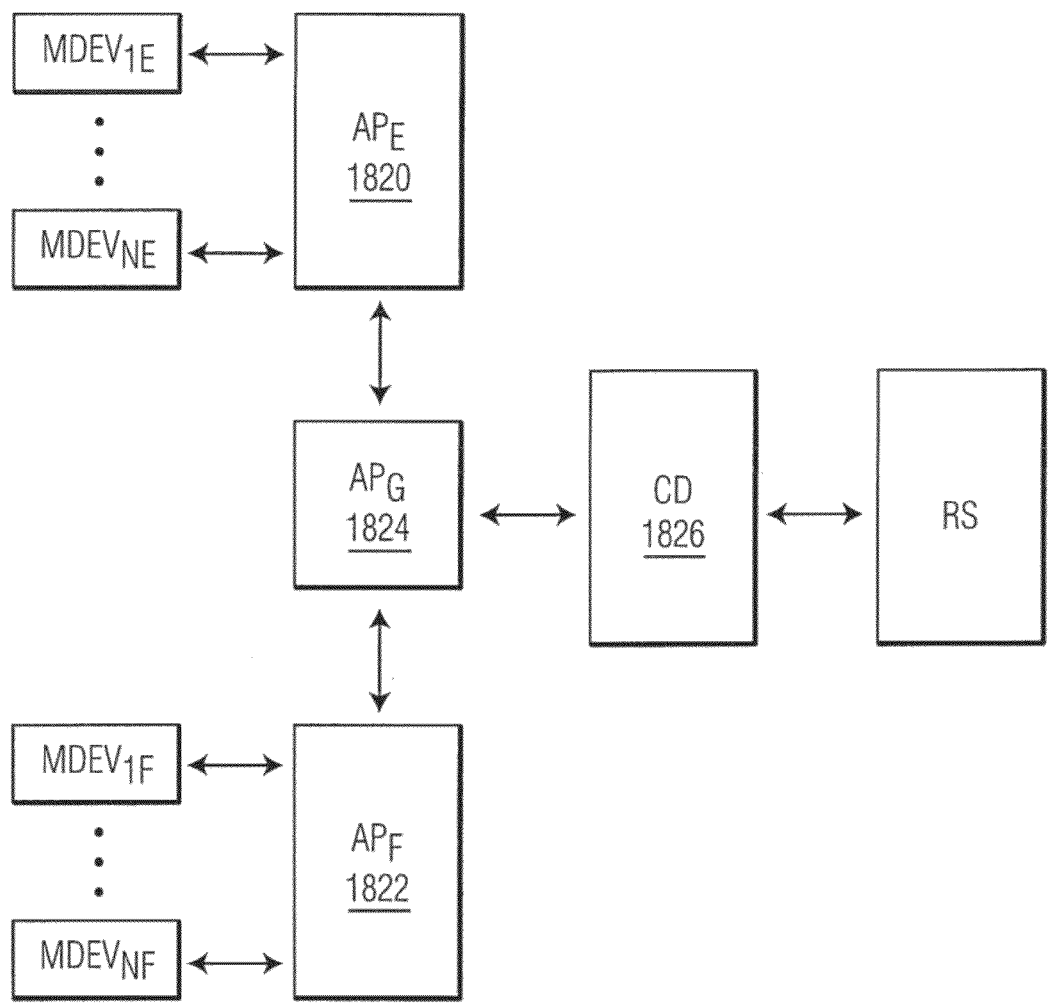
FIG. 18C shows a block diagram of a system which includes three adapters.

FIG. 18C shows a block diagram of a system which includes three adapters. In this configuration adapter 1820 communicates with a first plurality of MDEVs, adapter 1822 communicates with a second plurality of MDEVs, and both 1820 and 1822 communicate through third adapter 1824 with CD 1826.

Figure 18D:
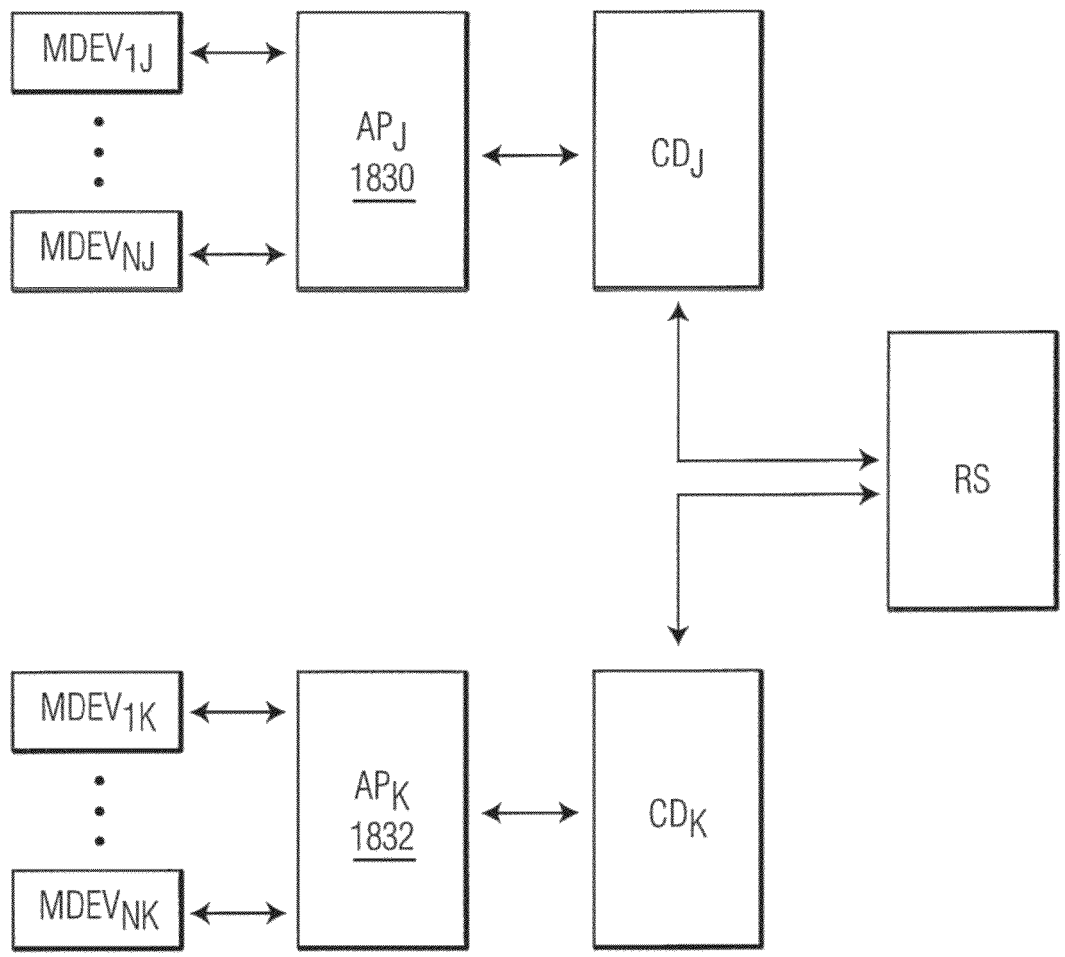
FIG. 18D shows a block diagram of yet another system which includes two adapters.

FIG. 18D shows a block diagram of yet another system which includes two adapters 1830 and 1832, each of which communicates with (i) a different plurality of MDEVs, and (ii) a different CD.

Figure 19A:
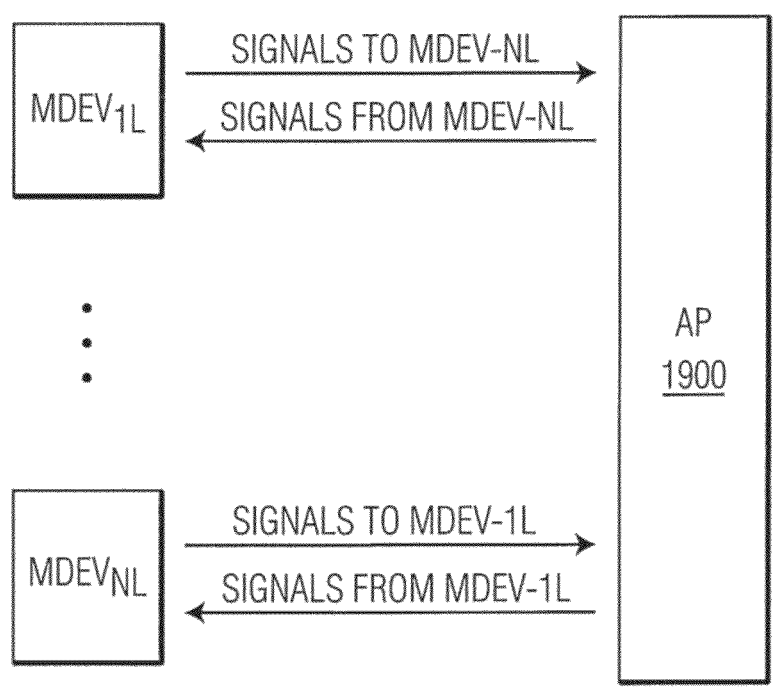
FIG. 19A shows a block diagram of the communication signals exchanged between an adapter and a plurality of medical devices.

FIG. 19A shows a block diagram of the communication signals exchanged between an adapter 1900 and a plurality of medical devices MDEV-1L to MDEV-NL. The adapter receives incoming signals from each of the medical devices, and provides outgoing signals to each of the MDEVs. Configurations in which one or more MDEVs receive but do not send such signals are possible (e.g. the insulin pump in one embodiment of a diabetes management system), and configurations in which one or more MDEVs send but do not receive signals are possible (e.g. sensors). In the configuration shown in FIG. 19A, the adapter's function is to facilitate communication among medical devices, without necessarily providing access to the devices to an outside agent.

Figure 19B:
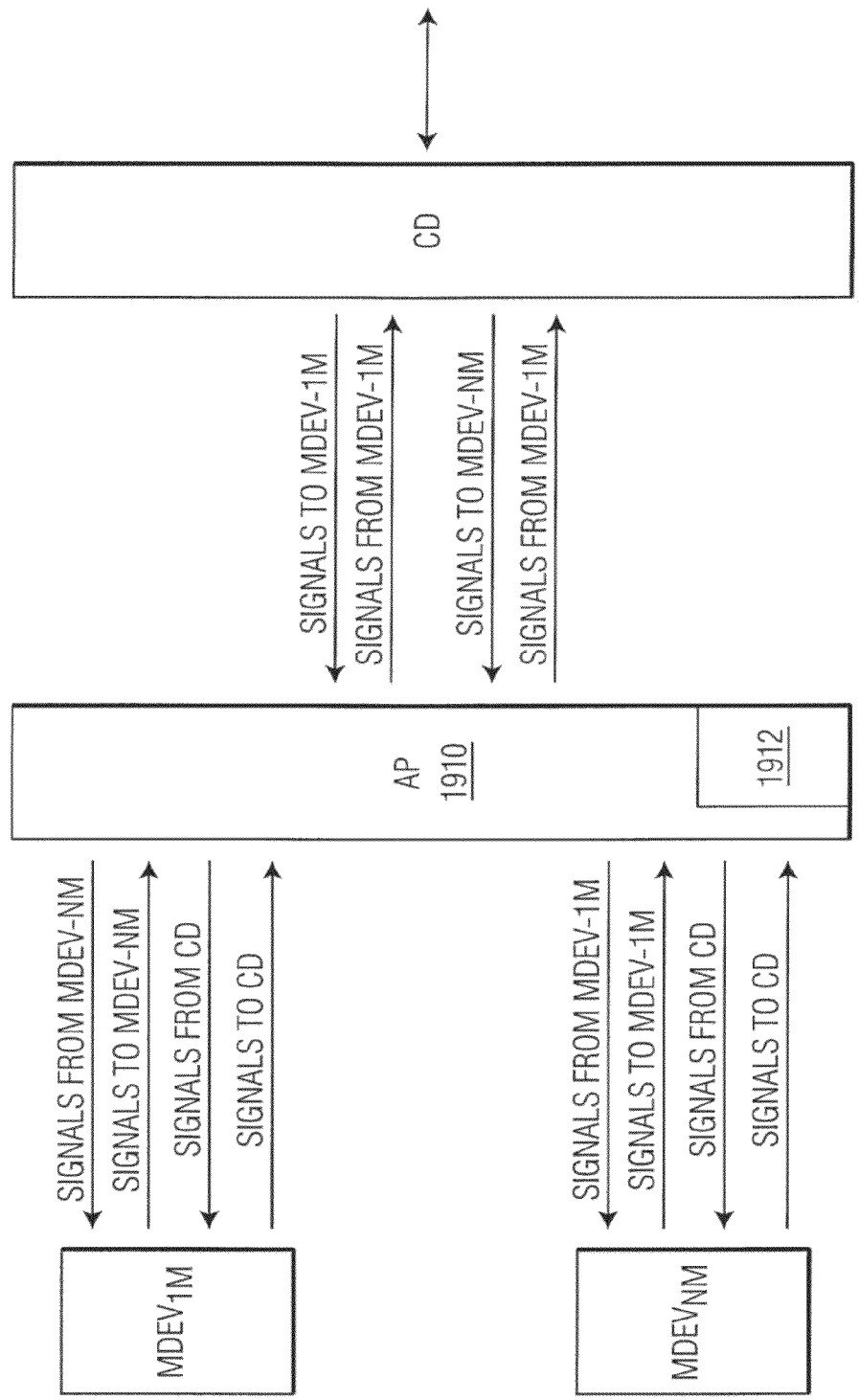
FIG. 19B shows a block diagram of the communication signals exchanged between an adapter and (i) a plurality of medical devices, (ii) a communications device.

FIG. 19B shows a block diagram of the communication signals exchanged between (i) an adapter 1910, (ii) a plurality of medical devices MDEV-1M to MDEV-NM (Such notation indicates the first through the nth device in this group of devices each considered to be one of a group of devices also labelled "M". Similar use of a dual label notation and its interpretation appears hereinabove and hereinbelow.), and (iii) a communications device, for a system in which each medical device is capable of two way communication with the CD through the adapter. Thus each medical device Each medical device:
    (a) receives signals from
        (i) each other medical device, via the adapter, and
        (ii) the CD, and
    (b) sends signals to
        (i) each other medical device, via the adapter, and
        (ii) the CD.
The adapter
    (a) receives signals for each medical device from the CD, and
    (b) sends signals to the CD from each medical device.
Some MDEVs in this grouping may feature one-way communication.

1910 also comprises a memory for storing identification information of a TA who wishes to communicate with one or more of the MDEVs. To protect against unauthorized communication, in a preferred embodiment of the invention, the memory will contain identification information of allowed users. In the event of a non-match of incoming identification information, options include:
- signals from the CD can not reach one or more of the MDEVs;
- signals from one or more of the MDEVs can not reach the CD; and
- a confirmation or non-confirmation signal may be sent to the TA which has either successfully been identified or has not.

FIG. 20 shows a block diagram of an adapter system which includes a permission device. Permission device 2002 is connected to adapter 2000, which is connected to each of two medical devices 2004 and 2006. The permission device allows the user to control one or more of the MDEVs. For example, 2004 could be a glucose sensor, and 2006 could be an insulin pump which uses glucose information from the sensor to determine a dose. The permission device allows the patient to override a decision of 2006 regarding insulin dosage. Furthermore, in a system in which an outside treatment agent (e.g. the patient's physician or another caregiver) can also control the pump, the patient also would have the opportunity to override such an outside decision about insulin management.

FIG. 21 shows a block diagram of an adapter system which includes a medical records apparatus 2100. 2100 may archive the information obtained from any of the MDEVs, archive incoming CD treatment commands, and/or archive the communication between any of the MDEVs.

Figure 22:
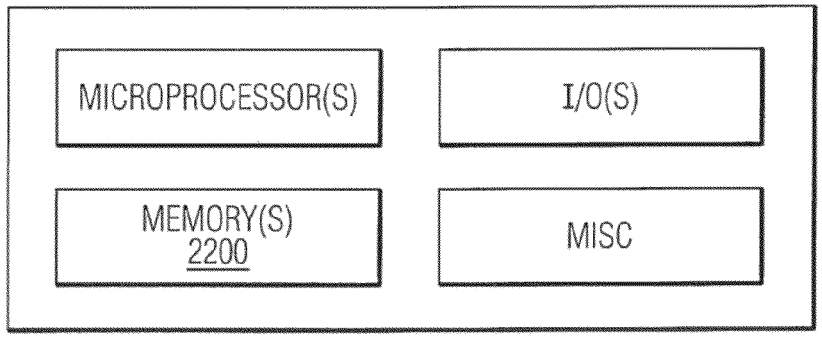
FIG. 22 shows a block diagram of apparatus within an adapter.

FIG. 22 shows a block diagram of apparatus within an adapter. Memory 2200 allows for the storage of communication protocols, of device identification and communication specifications, url and other addresses, and events such as those referred to in conjunction with FIG. 21. Furthermore, the memory may store either or both of (i) alphanumeric information identifying allowed users and/or passwords (ii) biologic identifying information concerning allowed users, (iii) information about different levels of access for different users (i.e. some TAs may be allowed to communicate with some MDEVs but not others, some TAs may be allowed to receive information from a MDEV but not program it).

Microprocessor(s) are known in the art; there may be one or a plurality. Logic/computational events may alternatively or in conjunction be microcontroller based, may be based on a custom integrated circuit or another computational device, all know in the art. Memory may reside in standalone memory units or in the aforementioned microcircuits. I/O devices, also known in the art are the subject of further discussion hereinbelow.

FIGS. 23A through 26 show a variety of adapter configurations involving different numbers and types of communication ports (labeled I/O devices), and different numbers and placements of data management devices. These figures are not intended to provide an exhaustive catalog of possible configurations, but merely to indicate the breadth of design options. The data management devices will include one or more processors or microcontrollers and may include one or more memory devices.

Figure 23A:
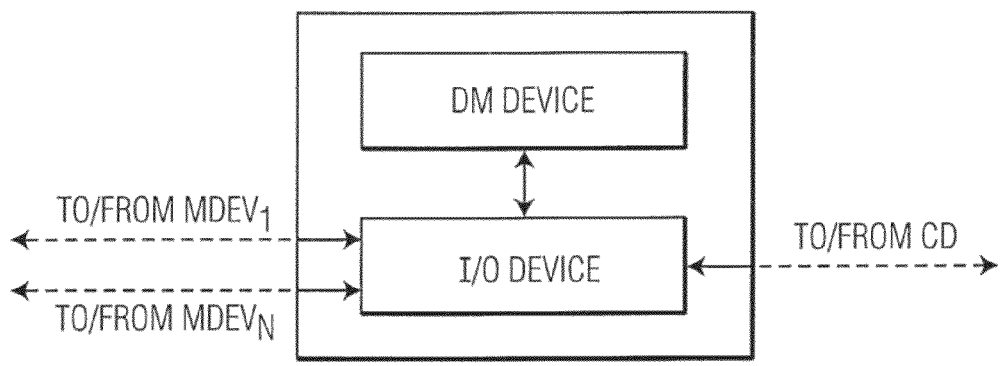
FIG. 23A shows a block diagram of apparatus within an adapter, and ingoing and outgoing signals.

FIG. 23A shows a block diagram of an adapter with a single data management ("DM") device and a single I/O device, which handles all incoming and outgoing signals.

Figure 23B:
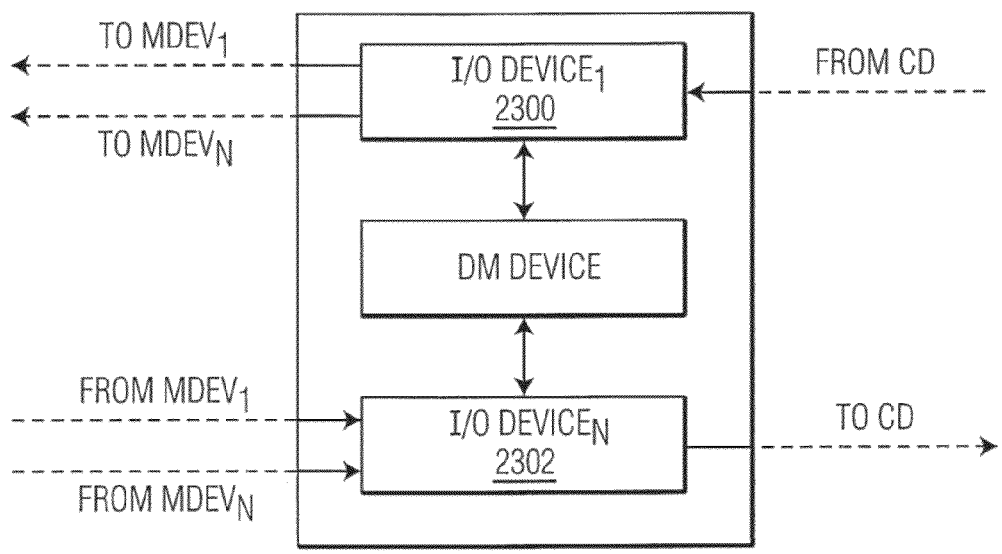
FIG. 23B shows another block diagram of apparatus within an adapter, and ingoing and outgoing signals.

FIG. 23B shows a block diagram of an adapter with one DM and with I/O device 2300 for signals from a CD to the MDEVs, and I/O device 2302 for outgoing signals.

Figure 23C:
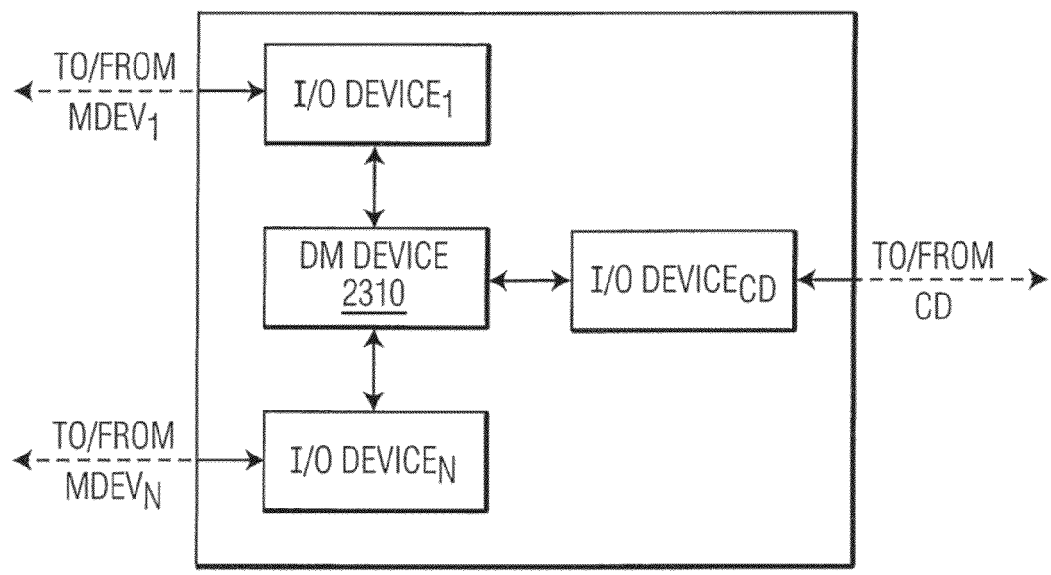
FIG. 23C shows another block diagram of apparatus within an adapter, and ingoing and outgoing signals.

FIG. 23C shows a block diagram of an adapter with one I/O device for each device (MDEVs and CD) with which the adapter communicates. A single DM 2310 communicates with each of the I/O devices. For example could translate a signal protocol for signals coming to and from a CD to MDEV-1, could translate a signal protocol for signals coming to and from a CD to MDEV-N (or any other of MDEV-2 through MDEV-[N minus 1]), or for signals coming from any MDEV to any other MDEV.

Figure 23D:
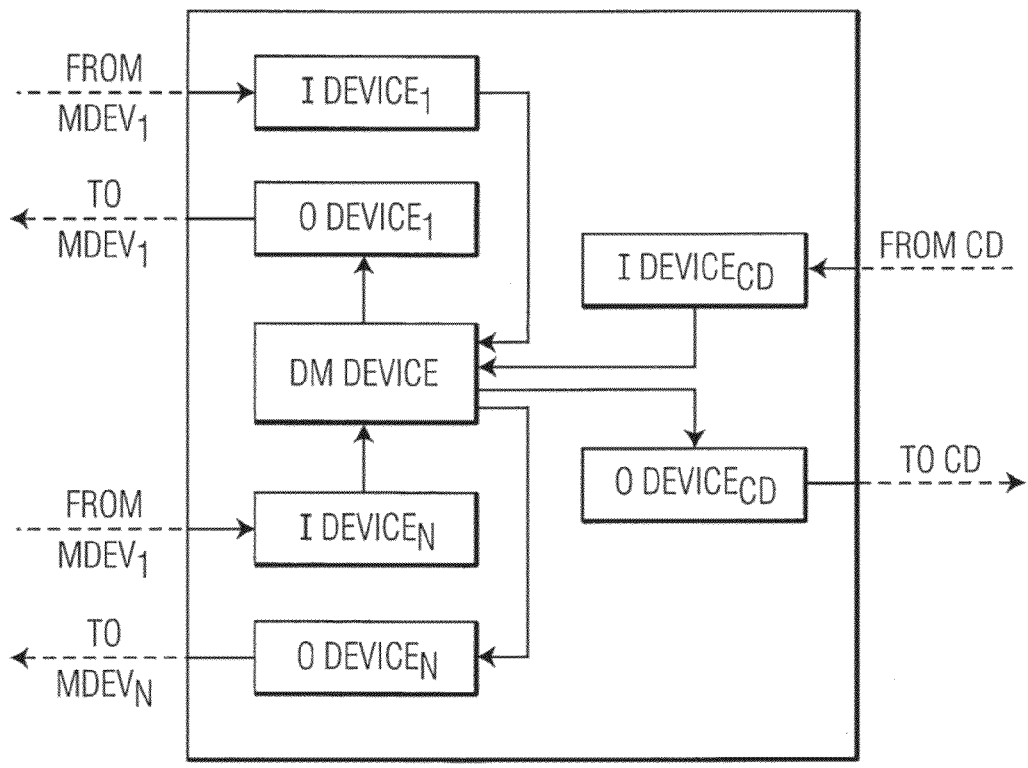
FIG. 23D shows yet another block diagram of apparatus within an adapter, and ingoing and outgoing signals.

FIG. 23D shows a block diagram of apparatus in which the input function and the output function of the I/O devices are separate; the configuration of the FIG. 23D device is otherwise similar to that of the FIG. 23C device.

Figure 24A:
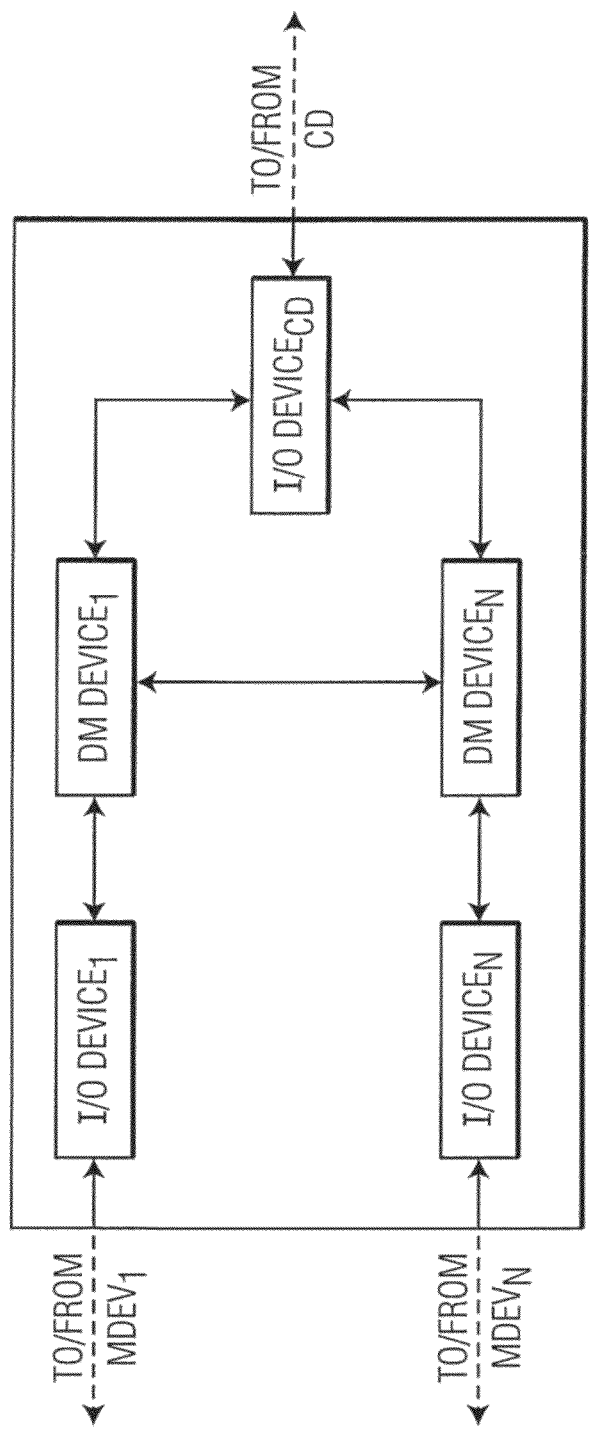
FIG. 24A shows yet another block diagram of apparatus within an adapter, and ingoing and outgoing signals.

FIG. 24A a block diagram of apparatus an adapter with one I/O device for each communicating entity and one DM device for each MDEV. The DM devices communicate with each other.

Figure 24B:
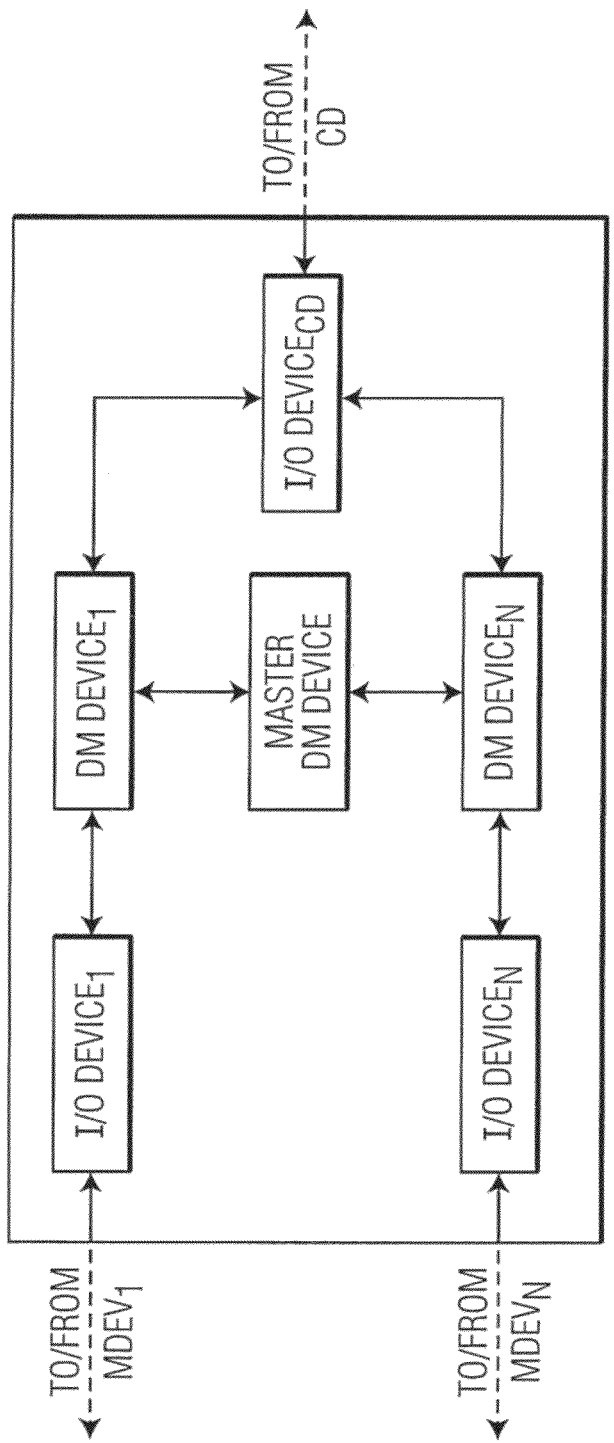
FIG. 24B shows another block diagram of apparatus within an adapter, and ingoing and outgoing signals.

The apparatus configuration of FIG. 24B is similar to that of FIG. 24A except that the DM devices, rather than communicating with each other, communicate through a master DM device.

Figure 25A:
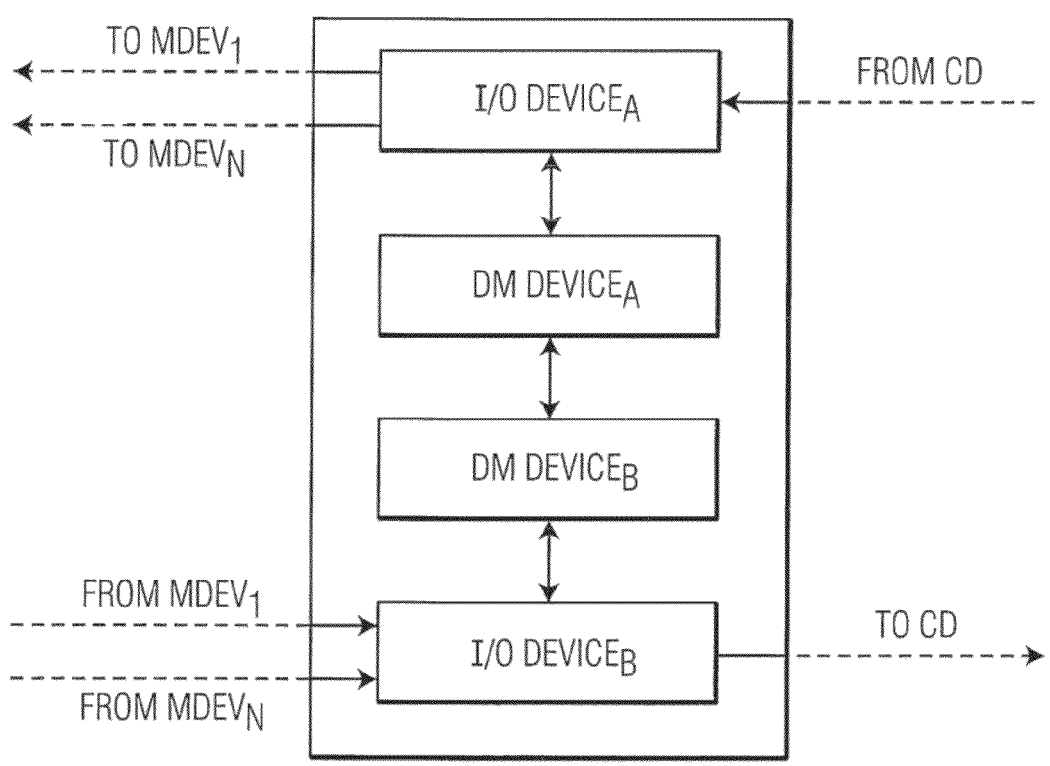
FIG. 25A shows another block diagram of apparatus within an adapter, and ingoing and outgoing signals.

FIG. 25A shows an adapter block diagram with a configuration similar to that of the adapter of FIG. 23B, except that each of the two I/O devices is associated with a respective DM device.

Figure 25B:
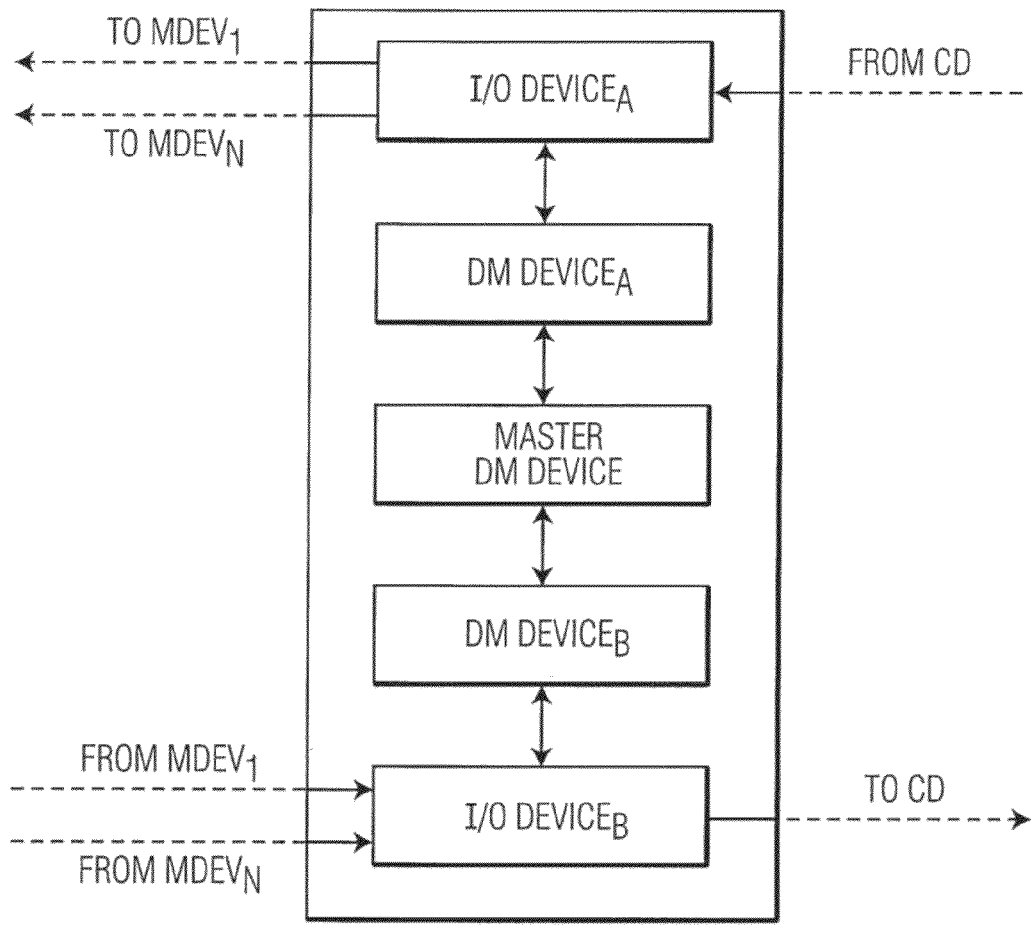
FIG. 25B shows still another block diagram of apparatus within an adapter, and ingoing and outgoing signals.

The apparatus configuration of FIG. 25B is similar to that of FIG. 25A except that the DM devices, rather than communicating with each other, communicate through a master DM device.

Figure 26:
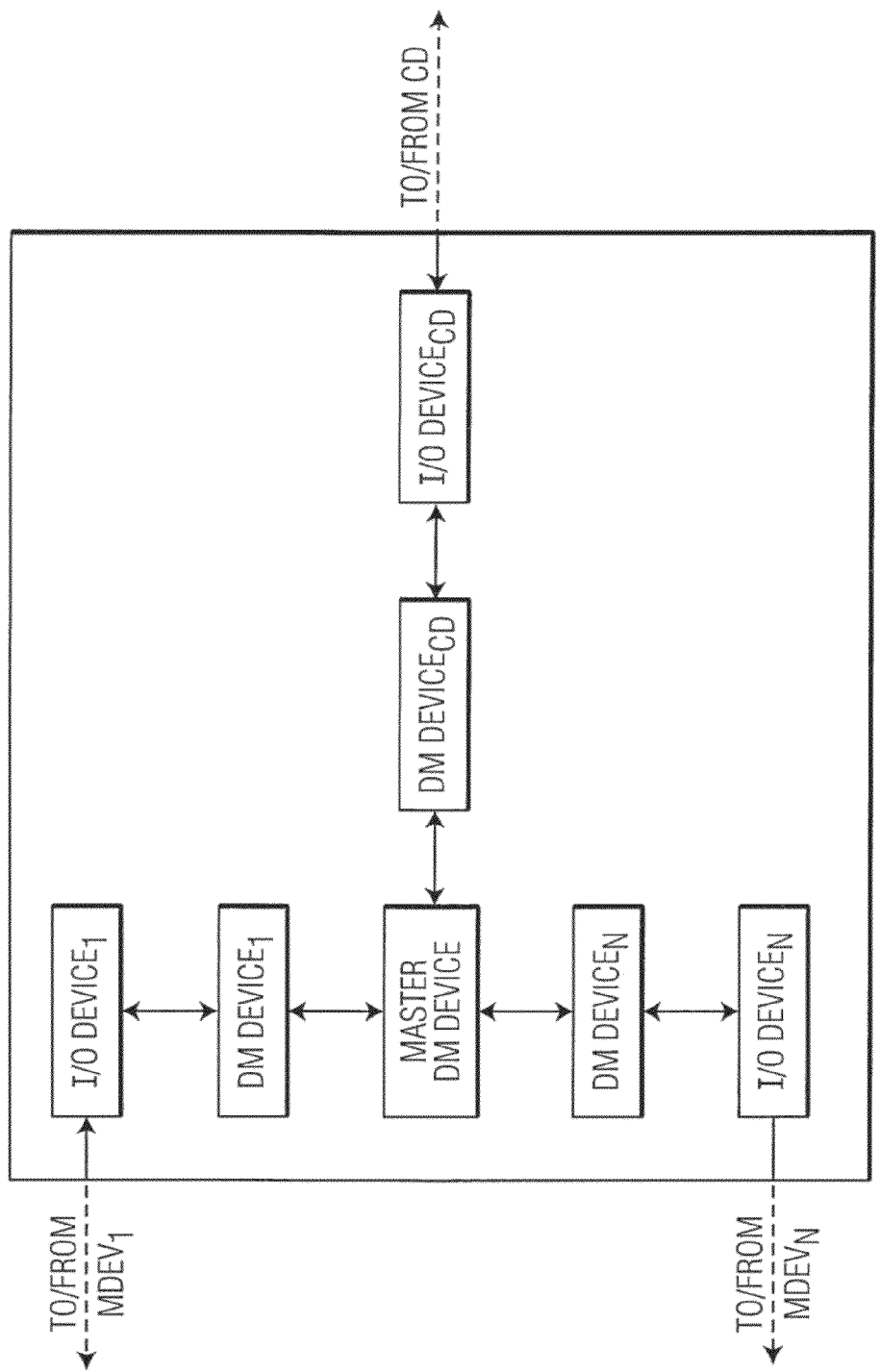
FIG. 26 shows still another block diagram of apparatus within an adapter, and ingoing and outgoing signals.

The apparatus configuration of FIG. 26 is similar to that of FIG. 24B except that the CD I/O device communicates through a respective DM device with the master DM device, rather than communicating with each MDEV DM device directly.

There is thus described apparatus and methodology which will allow a cell phone or other portable communications device to serve as the communications end of a remotely controlled medical monitoring and treatment device, such as a defibrillator, thereby facilitating the adaptation of minimally modified AEDs, manually controlled defibrillators and implanted pacemakers and defibrillators to serve as a sub-unit of Remotely Controlled Defibrillators. Many other modifications based on similar principles will be obvious to those skilled in the art.

What is claimed is:

1. An electronic adapter device configured to allow at least one of a plurality of medical treatment devices, which are configured to treat a person, to communicate with at least one other medical treatment device of the plurality, said adapter device including:
  (a) at least one communications port configured to communicate with each of said plurality of medical treatment devices for inputting and outputting medical information signals;
  (b) a data processing device, comprising at least one processor and connected to said communications port, wherein, in response to the receipt of a first information signal via said communications port from one of said plurality of treatment devices, said data processing device is configured to produce a second information signal for transmission via said communications port to another one of said plurality of treatment devices;
    wherein said data processing device is configured to change a data format of said first information signal outputted by said one medical treatment device to a data format of said second information signal compatible with said other one of said medical treatment devices; and wherein information is transmitted from one of said medical treatment devices via said adapter to said other one of said medical treatment devices; and whereby said adapter is configured to allow said medical treatment devices to communicate with each other.

2. The apparatus defined in claim 1, wherein said data format is a signal format.

3. The apparatus defined in claim 1, wherein said data format is an information format.

4. The apparatus defined in claim 1, wherein said treatment device is operative to provide medical therapy.

5. The apparatus defined in claim 1, wherein said treatment device is operative to sense a value of a physiologic parameter of a body of said person.

6. The apparatus defined in claim 1, wherein said first and said second information signals represent information for controlling a delivery of therapy by said treatment device.

7. The apparatus defined in claim 1, wherein said first and said second information signals represent at least one value of a physiologic parameter sensed by said treatment device.

8. The apparatus defined in claim 1, wherein said first and said second information signals represent information indicating the performance of said treatment device.

9. The apparatus defined in claim 1, further comprising a computer memory device, coupled to at least one of said processors, wherein said at least one processor is further operative to retrieve information stored in said memory.

10. The apparatus defined in claim 9, wherein said memory device is configured for storage of at least one of (i) a communication format, and (ii) a communications protocol.

11. The apparatus defined in claim 9, wherein said memory device is configured for storage of at least one of (i) allowed treatment device serial numbers, and (ii) allowed treatment device model numbers, wherein said adapter is configured to communicate with treatment devices represented by at least one of said model numbers and said serial numbers.

12. The apparatus defined in claim 1, wherein said at least one communications port comprises at least one communications device for each treatment device.

13. The apparatus defined in claim 1, wherein said adapter is adapted for communication with a first communications device ("C/D");
wherein, in response to the receipt of a third information signal via said communications port from one of said plurality of treatment devices, said data processing device is configured to produce a fourth information signal for transmission via said communications port to said first C/D;
wherein said data processing device is configured to change a data format of said third information signal outputted by said one medical treatment device to a data format compatible with said first C/D;
wherein information is transmitted from one of said medical treatment devices via said adapter to said first C/D; and
whereby said adapter is configured to allow said medical treatment devices to communicate with each other and with said first C/D.

14. The system defined in claim 13, further comprising said first C/D;
wherein said first C/D further comprises:
a receiving device configured to communicate with said at least one communications port of said adapter;
a first C/D processor, coupled to said receiving device; and
a C/D display device, coupled to said first C/D processor, for displaying treatment device information for a treating person;
wherein said first C/D processor is operative to cause said display device to display a representation of the information specified by said fourth information signal;
whereby said treatment person utilizes said C/D to communicate with at least one of said plurality of medical treatment devices.

15. The system defined in claim 13, further comprising said first C/D;
wherein said first C/D further comprises:
a first transmitting and receiving "T/R" device configured to communicate with said at least one communications port of said adapter;
a third C/D processor, coupled to said first T/R device, configured to receive and analyze information represented by said fourth information signal and to generate control information for control of one of said treatment devices;
wherein said control information causes said first T/R device to generate a seventh information signal for transmission to said adapter;
wherein in response to the receipt of said seventh information signal via said communications port from said first C/D, said data processing device is configured to produce an eighth information signal for transmission via said communications port to one of said plurality of treatment devices;
wherein said data processing device is configured to change a data format of said seventh information signal outputted by said first C/D to a data format compatible with one of said plurality of treatment devices; and
wherein information is transmitted from said first C/D via said adapter to one of said treatment devices; and
whereby said adapter is configured to allow said medical treatment devices to communicate with each other and with said first C/D, and
whereby said third processor controls one of said treatment devices via said adapter.

16. The system defined in claim 13, further comprising a third C/D,
wherein said third C/D comprises a second T/R device for:
(a) receiving the information represented by said fourth information signal, and
(b) transmitting said information to a remote communications device, located remotely from said third C/D
wherein the information represented by said fourth information signal is transmitted sequentially from said adapter to said third C/D, and thereafter to said remote C/D;
whereby said remote C/D communicates with at least one of said plurality of treatment devices, for receipt of information from said treatment device.

17. The system defined in claim 16, wherein said second T/R device is operative to:
(a) receive control information from said remotely located communications device, for control of at least one of said treatment devices, and
(b) transmit a ninth information signal to said adapter representing said control information;
wherein said control information is transmitted sequentially from said remote C/D to said third C/D, to said adapter, and thereafter to said at least one treatment device;

whereby said remote C/D communicates with at least one of said plurality of treatment devices for transmission of control information from the remote C/D.

18. The apparatus defined in claim 1, wherein said adapter is adapted for communication with a second communications device ("C/D");
    wherein, in response to the receipt of a fifth information signal via said communications port from a second C/D, said data processing device is configured to produce a sixth information signal for transmission via said communications port to one of said plurality of treatment devices;
        wherein said data processing device is configured to change a data format of said fifth information signal outputted by said second C/D to a data format compatible with one of said plurality of treatment devices;
        wherein information is transmitted from said second C/D via said adapter to one of said treatment devices; and
        whereby said adapter is configured to allow said medical treatment devices to communicate with each other and with said second C/D.

19. The system defined in claim 18, further comprising said second C/D;
    wherein said second C/D further comprises:
        a transmitting device configured to communicate with said at least one communications port of said adapter;
        a second C/D processor, coupled to said second transmitting device; and
        a C/D input device, coupled to said second C/D processor, configured to input treatment instructions by a treating person;
    wherein said second C/D processor is operative to cause said transmitting device to produce said fifth information signal representing said treatment instructions, for transmission to said at least one communications port;
    whereby said treatment person utilizes said second C/D to communicate with at least one of said plurality of medical treatment devices.

20. The system defined in claim 1, wherein at least one of said medical treatment devices is selected from the group consisting of:
    (i) a defibrillator,
    (ii) a pacemaker,
    (iii) a left ventricular assist device,
    (iv) a right ventricular assist device,
    (v) a mechanical heart,
    (vi) a brain stimulating device,
    (vii) a nerve stimulating device,
    (viii) a spinal cord stimulating device,
    (ix) a muscle stimulating device,
    (x) a stomach stimulating device,
    (xi) an intestine stimulating device,
    (xii) a bladder stimulating device,
    (xiii) a carotid body stimulating device,
    (xiv) an insulin pump,
    (xv) a drug delivery device,
    (xvi) a pH sensor,
    (xvii) a $pCO_2$ sensor,
    (xviii) an oxygen sensor,
    (xix) an oxygen saturation sensor,
    (xx) a glucose sensor,
    (xxi) a fructose sensor,
    (xxii) a ketone sensor,
    (xxiii) a lactate sensor,
    (xxiv) a cardiac output sensor,
    (xxv) a sensor of tissue electrical activity,
    (xxvi) a pressure sensor,
    (xxvii) an arterial pressure sensor,
    (xxviii) a venous pressure sensor,
    (xxix) a left atrial pressure sensor,
    (xxx) a right atrial pressure sensor,
    (xxxi) a thoracic impedance sensor,
    (xxxii) a $QT_C$ sensor,
    (xxxiii) a temperature sensor,
    (xxxiv) a skin resistance sensor,
    (xxxv) a thoracic impedance sensor,
    (xxxvi) a body weight sensor
    (xxxvii) a sound sensor,
    (xxxviii) a camera,
    (xxxix) an accelerometer, and
    (xl) a global positioning device.

21. Medical treatment apparatus configured to allow a plurality of medical treatment devices, which are configured to treat a person, to communicate with a treatment agent, said apparatus comprising, in combination:
    (A) an electronic adapter device configured to allow a plurality of medical treatment devices, which are configured to treat a person, to communicate with a first transmitting/receiving (T/R) device which, in turn, is adapted to communicate with a treatment agent, for controlling the treatment of the person, said adapter device including:
        (1) at least one communications port configured to communicate with each of said plurality of medical treatment devices and with said first T/R device configured to input and output medical information signals;
        (2) a data processing device, comprising at least one processor and connected to said communications port,
            (a) wherein, in response to the receipt of a first information signal via said communications port from a first one of said plurality of treatment devices, said data processing device is configured to produce a second information signal for transmission via said communications port to said first T/R device;
            wherein said data processing device is configured to change a data format of said first information signal outputted by one of said plurality of treatment devices to a data format of said second information signal compatible with said first T/R device; and
            (b) wherein, in response to the receipt of a third information signal via said communications port from said first T/R device, said data processing device is configured to produce a fourth information signal for transmission via said communications port to a second one of said medical treatment devices;
            wherein said data processing device is configured to change a data format of said third information signal outputted by said first T/R device to a data format of said fourth information signal compatible with said second one of said medical treatment devices; and
    (B) a first T/R device comprising a first transmitting and receiving means configured to:
        (1) receive said second information signal from said adapter communications port for transmission to said treatment agent; and
        (2) transmit said third information signal received from said treatment agent to said adapter communications port;
            wherein said adapter is adapted to cause information outputted by one of said medical treatment devices and carried by said first information signal to be carried by said second information signal compatible with said first T/R device;

wherein said adapter is adapted to cause information outputted by said first T/R device and carried by said third information signal to be carried by said fourth information signal compatible with said second treatment device, wherein information represented by said first information signal is transmitted from one of said medical treatment devices via said adapter to said first T/R device for evaluation by said treatment agent;

wherein information from said treatment agent represented by said third information signal is transmitted via said adapter from said first T/R device to said second one of said medical treatment devices;

whereby said adapter is configured to allow (i) each of said medical treatment devices and (ii) said treatment agent to communicate.

22. The apparatus defined in claim 21, wherein said data format is a signal format.

23. The apparatus defined in claim 21, wherein said data format is an information format.

24. The apparatus defined in claim 21, wherein at least one treatment device is operative to provide medical therapy.

25. The apparatus defined in claim 21, wherein said treatment device is operative to sense a value of a physiologic parameter of a body of said person.

26. The apparatus defined in claim 21, wherein said first T/R device further comprises
　(a) a display device, for displaying a representation of said second information signal;
　(b) an input device, configured to input a treatment command for providing control information for one of said treatment devices;
　(c) a first processor, coupled to each of said first T/R device, said display device and said input device, configured to
　　(i) cause said display device to display a representation of said second information signal;
　　(ii) produce said third information signal, in response to said inputted treatment command;
　whereby said treatment agent utilizes said first T/R device to communicate with said plurality of medical treatment devices.

27. The apparatus defined in claim 21, wherein
　(a) said first transmitting and receiving means is further configured to communicate with a second T/R device, situated remotely from said first T/R device, and
　(b) said first T/R device is coupled to a second processor adapted to cause said first transmitting and receiving means to communicate with said second T/R device;
　whereby said treatment agent utilizes said second T/R device to communicate with said plurality of medical treatment devices.

28. The apparatus defined in claim 27, further comprising said second T/R device.

29. The apparatus define in claim 21, wherein said first T/R device further comprises a supplementary processor, coupled to said transmitting and receiving means, configured to receive and analyze information represented by said second information signal and to generate information represented by said third information signal for control of said second treatment device.

30. The apparatus defined in claim 21, wherein at least one of said medical treatment devices is selected from the group consisting of:
　(i) a defibrillator,
　(ii) a pacemaker,
　(iii) a left ventricular assist device,
　(iv) a right ventricular assist device,
　(v) a mechanical heart,
　(vi) a brain stimulating device,
　(vii) a nerve stimulating device,
　(viii) a spinal cord stimulating device,
　(ix) a muscle stimulating device,
　(x) a stomach stimulating device,
　(xi) an intestine stimulating device,
　(xii) a bladder stimulating device,
　(xiii) a carotid body stimulating device,
　(xiv) an insulin pump,
　(xv) a drug delivery device,
　(xvi) a pH sensor,
　(xvii) a $pCO_2$ sensor,
　(xviii) an oxygen sensor,
　(xix) an oxygen saturation sensor,
　(xx) a glucose sensor,
　(xxi) a fructose sensor,
　(xxii) a ketone sensor,
　(xxiii) a lactate sensor,
　(xxiv) a cardiac output sensor,
　(xxv) a sensor of tissue electrical activity,
　(xxvi) a pressure sensor,
　(xxvii) an arterial pressure sensor,
　(xxviii) a venous pressure sensor,
　(xxix) a left atrial pressure sensor,
　(xxx) a right atrial pressure sensor,
　(xxxi) a thoracic impedance sensor,
　(xxxii) a $QT_C$ sensor,
　(xxxiii) a temperature sensor,
　(xxxiv) a skin resistance sensor,
　(xxxv) a thoracic impedance sensor,
　(xxxvi) a body weight sensor
　(xxxvii) a sound sensor,
　(xxxviii) a camera,
　(xxxix) an accelerometer, and
　(xl) a global positioning device.

31. Medical treatment apparatus configured to allow at least one medical treatment device which is configured to treat a person, to securely communicate with a treatment agent, said apparatus comprising an electronic adapter device configured to allow at least one medical treatment device which is configured to treat a person, to securely communicate with a first transmitting/receiving (T/R) device which, in turn, is adapted to communicate with a treatment agent, for controlling the treatment of the person, said adapter device including:
　(A) at least one communications port, configured to communicate with said at least one medical treatment device and with said first T/R device, configured to receive and output medical information signals and to receive incoming identification information;
　(B) a data processing device including:
　　(a) a data memory configured to store allowed identification information representing identification information of at least one treatment agent who is allowed to communicate with said medical treatment device; and
　　(b) a processor, connected to said communications port and to said memory, configured to compare said incoming identification information with said allowed identification information to determine if said at least one treatment agent is authorized to communicate with one or more of said medical treatment devices, said processor being:
　　　(1) responsive to the receipt of a first information signal via said communications port from said first T/R device, for producing a second information signal for transmission via said communications port to at least one of said treatment devices only if said incoming identification information matches said allowed identification information; and (2) responsive to the receipt of at least one third information signal via said communications port from said at least one medical treatment device, for producing at least one fourth information signal for transmission via said communications port to said first T/R device;

wherein said communications port is configured to change a data format of said first information signal received from said first T/R device to a data format of said second information signal compatible with at least one of said treatment devices; and wherein said communications port is configured to change a data format of said third information signal received from said at least one medical treatment device to a data format of said fourth information signal compatible with said first T/R device;

wherein said adapter device is operative:
- (i) to cause information received from said first T/R device and carried by said first information signal to be carried by said second information signal and forwarded to said at least one medical treatment device, only if said incoming identification information matches said stored identification information;
- (ii) to cause information outputted by said at least one medical treatment device and carried by said third information signal to be carried by said fourth information signal and forwarded to said first T/R device;
- (iii) to forward information from said treatment agent and represented by said first information signal and received from said first T/R device to said at least one medical treatment device only if said incoming identification information matches said stored identification information;
- (iv) to forward information from said at least one medical treatment device and represented by said third information signal to said first T/R device for transmission to and evaluation by said treatment agent;

whereby said adaptor device is configured to allow said treatment agent to send information to said at least one medical treatment device only if said treatment agent identification information matches identification information stored in said adapter.

32. The apparatus defined in claim 31, wherein said identification information is alphanumeric.

33. The apparatus defined in claim 31, wherein said treatment agent is a human treatment agent, and wherein said identification information represents information specifying a unique biologic feature of said treatment agent.

34. The apparatus defined in claim 31, further comprising said first T/R device.

35. The apparatus defined in claim 31, wherein said data format is a signal format.

36. The apparatus defined in claim 31, wherein said data format is an information format.

37. The apparatus defined in claim 31, wherein at least one treatment device is operative to provide medical therapy.

38. The apparatus defined in claim 31, wherein said treatment device is operative to sense a value of a physiologic parameter of a body of said person.

39. The apparatus defined in claim 31, wherein at least one of said medical treatment devices is selected from the group consisting of:
- (i) a defibrillator,
- (ii) a pacemaker,
- (iii) a left ventricular assist device,
- (iv) a right ventricular assist device,
- (v) a mechanical heart,
- (vi) a brain stimulating device,
- (vii) a nerve stimulating device,
- (viii) a spinal cord stimulating device,
- (ix) a muscle stimulating device,
- (x) a stomach stimulating device,
- (xi) an intestine stimulating device,
- (xii) a bladder stimulating device,
- (xiii) a carotid body stimulating device,
- (xiv) an insulin pump,
- (xv) a drug delivery device,
- (xvi) a pH sensor,
- (xvii) a $pCO_2$ sensor,
- (xviii) an oxygen sensor,
- (xix) an oxygen saturation sensor,
- (xx) a glucose sensor,
- (xxi) a fructose sensor,
- (xxii) a ketone sensor,
- (xxiii) a lactate sensor,
- (xxiv) a cardiac output sensor,
- (xxv) a sensor of tissue electrical activity,
- (xxvi) a pressure sensor,
- (xxvii) an arterial pressure sensor,
- (xxviii) a venous pressure sensor,
- (xxix) a left atrial pressure sensor,
- (xxx) a right atrial pressure sensor,
- (xxxi) a thoracic impedance sensor,
- (xxxii) a $QT_C$ sensor,
- (xxxiii) a temperature sensor,
- (xxxiv) a skin resistance sensor,
- (xxxv) a thoracic impedance sensor,
- (xxxvi) a body weight sensor;
- (xxxvii) a sound sensor,
- (xxxviii) a camera,
- (xxxix) an accelerometer, and
- (xl) a global positioning device.

* * * * *